(12) United States Patent
Whitten

(10) Patent No.: US 8,524,763 B2
(45) Date of Patent: Sep. 3, 2013

(54) INHIBITORS OF STORE OPERATED CALCIUM RELEASE

(75) Inventor: Jeffrey P. Whitten, Santee, CA (US)

(73) Assignee: Calcimedica, Inc., La Jolla, CA (US)

( * ) Notice: Subject to any disclaimer, the term of this patent is extended or adjusted under 35 U.S.C. 154(b) by 635 days.

(21) Appl. No.: 12/564,819

(22) Filed: Sep. 22, 2009

(65) Prior Publication Data

US 2010/0152241 A1   Jun. 17, 2010

Related U.S. Application Data

(60) Provisional application No. 61/099,055, filed on Sep. 22, 2008.

(51) Int. Cl.
| | |
|---|---|
| *A61K 31/381* | (2006.01) |
| *A61K 31/4025* | (2006.01) |
| *A61K 31/4535* | (2006.01) |
| *C07D 333/02* | (2006.01) |
| *C07D 333/46* | (2006.01) |

(52) U.S. Cl.
USPC ............... 514/447; 514/438; 514/443; 549/1; 549/29; 549/41; 549/43; 549/83

(58) Field of Classification Search
USPC ............ 514/326, 422, 447, 438, 443; 549/1, 549/29, 41, 43, 83
See application file for complete search history.

(56) References Cited

U.S. PATENT DOCUMENTS

| | | | |
|---|---|---|---|
| 4,658,040 A | 4/1987 | Baird et al. | |
| 6,323,227 B1 | 11/2001 | Klein et al. | |
| 6,861,419 B2 | 3/2005 | Drewe et al. | |
| 6,919,359 B2 | 7/2005 | Piotrowski et al. | |
| 7,410,945 B2 * | 8/2008 | Woodruff et al. ............. | 514/1.1 |
| 7,906,553 B2 | 3/2011 | Velicelebi et al. | |
| 2004/0142980 A1 | 7/2004 | Finzel et al. | |
| 2006/0199845 A1 | 9/2006 | Sun et al. | |
| 2007/0249050 A1 | 10/2007 | Chen et al. | |
| 2007/0249051 A1 | 10/2007 | Bohnert et al. | |
| 2007/0249609 A1 | 10/2007 | Chen et al. | |
| 2007/0249661 A1 | 10/2007 | Chen et al. | |
| 2007/0254363 A1 | 11/2007 | Chen et al. | |
| 2007/0254912 A1 | 11/2007 | Chen et al. | |
| 2007/0254925 A1 | 11/2007 | Vo et al. | |
| 2007/0254926 A1 | 11/2007 | Jiang et al. | |
| 2009/0137659 A1 | 5/2009 | Velicelebi et al. | |
| 2010/0305200 A1 | 12/2010 | Velicelebi et al. | |
| 2011/0136816 A1 | 6/2011 | Velicelebi et al. | |
| 2011/0212970 A1 | 9/2011 | Velicelebi et al. | |

FOREIGN PATENT DOCUMENTS

| | | | |
|---|---|---|---|
| DE | 201306 | * | 7/1983 |
| DE | 216237 | * | 12/1984 |
| DE | 235873 | | 5/1986 |
| DE | 240890 | | 11/1986 |
| EP | 0202538 A1 | | 11/1986 |
| EP | 1754483 A1 | | 2/2007 |
| WO | WO 94/12505 | | 6/1994 |
| WO | WO 98/54116 | | 12/1998 |
| WO | WO-02/30976 A1 | | 4/2002 |
| WO | WO 02/48131 | | 6/2002 |
| WO | WO 03/013517 | | 2/2003 |
| WO | WO03/101979 A1 | | 12/2003 |
| WO | WO-2004/041813 A1 | | 5/2004 |
| WO | WO 2005/009954 | | 2/2005 |
| WO | WO 2005/033102 | | 4/2005 |
| WO | WO2006/007864 A1 | | 1/2006 |
| WO | WO-2006/012642 A2 | | 2/2006 |
| WO | WO 2006/081389 | | 8/2006 |
| WO | WO 2006/081391 | | 8/2006 |
| WO | WO 2006/083477 | | 8/2006 |
| WO | WO 2006/089177 | | 8/2006 |
| WO | WO2006/093518 A2 | | 9/2006 |
| WO | WO-2006/124887 A1 | | 11/2006 |
| WO | WO 2007/017264 | | 2/2007 |
| WO | WO-2007/083689 A1 | | 7/2007 |
| WO | WO 2007/087429 | | 8/2007 |
| WO | WO 2007/112093 | | 10/2007 |
| WO | WO 2008/063504 | | 5/2008 |
| WO | WO 2008/122038 | | 10/2008 |
| WO | WO2009/035818 A1 | | 3/2009 |
| WO | WO2009/076454 A2 | | 6/2009 |

OTHER PUBLICATIONS

Noack, "Synthesis and characterisation of N,N-disubstituted 2-amino-5-acylthiophenes and 2-amino-5-acylthiazoles", Tetrahedron, 2002, 58(11), 2137-2146.*
PCT/US2008/073392 International Search Report dated Feb. 11, 2009.
ScienceIP search report dated Feb. 19, 2007.
ScienceIP search report dated Feb. 20, 2007.
Henry, "Calcium antagonists as antiatherogenic agents", Ann N Y Acad Sci. 522:411-9, 1988.
Schepetkin et al., "High-throughput screening for small-molecule activators of neutrophils: identification of novel N-formyl peptide receptor agonists," Mol Pharmacol. 71(4):1061-74, 2007.
Sweeney et al., "Small-molecule inhibitors of store-operated calcium entry," ChemMedChem. 4(5):706-18, 2009.
Yonetoku et al., "Novel potent and selective $Ca^{2+}$release-activated $Ca^{2+}$(CRAC) channel inhibitors. Part 3: synthesis and CRAC channel inhibitory activity of 4'-[(trifluoromethyl)pyrazol-1-yl]carboxanilides," Bioorg Med Chem. 16(21):9457-66, 2008.
Yonetoku et al., "Novel potent and selective calcium-release-activated calcium (CRAC) channel inhibitors. Part 1: synthesis and inhibitory activity of 5-(1-methyl-3-trifluoromethyl-1H-pyrazol-5-yl-2-thiophenecarboxamides," Bioorg Med Chem. 14(14):4750-60, 2006.

(Continued)

*Primary Examiner* — Sreeni Padmanabhan
*Assistant Examiner* — Sahar Javanmard
(74) *Attorney, Agent, or Firm* — Wilson, Sonsini, Goodrich & Rosati

(57) ABSTRACT

Described herein are compounds and pharmaceutical compositions containing such compounds, which modulate the activity of store-operated calcium (SOC) channels. Also described herein are methods of using such SOC channel modulators, alone and in combination with other compounds, for treating diseases, disorders or conditions that would benefit from inhibition of SOC channel activity.

13 Claims, 2 Drawing Sheets

(56) References Cited

OTHER PUBLICATIONS

Yonetoku et al., "Novel potent and selective calcium-release-activated calcium (CRAC) channel inhibitors. Part 2: Synthesis and inhibitory activity of aryl-3-trifluoromethylpyrazoles," Bioorg Med Chem. 14(15):5370-83, 2006.

PCT/US2009/055090 International Search Report dated Apr. 7, 2010.

Leistner et al., "Synthesis," 1987, pp. 466-470, vol. 5.

Perrissin, M. et al., "Synthesis and Pharmacology of 2-amino-3-ethoxycarbony.-4-phenithiophene derivatives," European Journal of Medicinal Chemistry, Jan. 1, 1980, pp. 563-565, vol. 15, No. 6, Editions Scientifique Elsevier, Paris, FR.

Examiner's First Report on Application No. 2009288245 by CalciMedica, Inc., Aug. 22, 2011, Australian Government, IP Australia, by Lorna Barr, Patent Examination A, C2-Chemical.

Extended European Search Report for Application No. EP 09 81 2055.3, European Patent Office, Oct. 17, 2011, The Hague, by Examiner Tim Lange.

Feske, "Calcium Signalling in Lymphocyte Activation and Disease," Nat. Rev. Immunol., 7(9):690-702 (2007).

Mizutani, et al. "Efficient method for high-throughput virtual screening based on flexible docking: discovery of novel acetylcholinesterase inhibitors" Journal of Medicinal Chemistry 47(20) pp. 4818-4828 (2004).

Ohora, Masatsugu "Roles of ER calcium sensors STIM1 and STIM2 in T cell development and function" Faseb Summer Research Conferences, URL:https://secure.faseb.org/faseb/meetings/Summrconf/programs/11643.pdf Jun. 23, 2007.

Oh-Hora, Masatsugu Dual functions for the endoplasmic reticulum calcium sensors STIM1 and STIM2 in T cell activation and tolerance: Nature Immunology, Nature Publishing Group GB vol. 9(4) 432-443 (2008).

Vippagunta, et al., "Crystalline solids," Advanced Drug Delivery Reviews, 48, 2001, 18.

Waisser, et al. "I-Aryl-5-benzylsulfanyltetrazoles, a new group of antimycobacterial compounds against potentially pathogenic strains" Folia Microbiologica 50(3) pp. 195-197 (2005).

EP 08781606.2 Search Report dated Jan. 27, 2011.

PCT/US2009/055247 International Search Report dated Mar. 10, 2011.

PCT/US2009/055090 International Preliminary Report on Patentability dated Mar. 10, 2011.

PCT/US2009/057883 International Search Report dated Mar. 31, 2011.

PCT/US2009/057905 International Search Report dated Mar. 31, 2011.

Canadian Application No. 2734500 Office Action dated Jun. 4, 2012.

Non-final Rejection for U.S. Appl. No. 12/564,819 dated May 18, 2012.

RU 2011108969 Office Action dated Apr. 12, 2012.

TW 098128758 Office Action dated Jun. 1, 2012.

\* cited by examiner

Typical $I_{CRAC}$ traces in response to the voltage stimulus immediately after break-in, before $I_{CRAC}$ is activated and at 5 min after $I_{CRAC}$ is fully activated by depletion of intracellular calcium stores.

INHIBITORS OF STORE OPERATED CALCIUM RELEASE

CROSS-REFERENCE

This application claims the benefit of U.S. provisional application Ser. No. 61/099,055, filed Sep. 22, 2008, which is incorporated by reference in its entirety.

FIELD OF THE INVENTION

Described herein are compounds, pharmaceutical compositions and medicaments that include such compounds, and methods of using such compounds to modulate store operated calcium (SOC) channel activity.

BACKGROUND OF THE INVENTION

Calcium plays a vital role in cell function and survival. For example, calcium is a key element in the transduction of signals into and within cells. Cellular responses to growth factors, neurotransmitters, hormones and a variety of other signal molecules are initiated through calcium-dependent processes.

Virtually all cell types depend in some manner upon the generation of cytoplasmic $Ca^{2+}$ signals to regulate cell function, or to trigger specific responses. Cytosolic $Ca^{2+}$ signals control a wide array of cellular functions ranging from short-term responses such as contraction and secretion to longer-term regulation of cell growth and proliferation. Usually, these signals involve some combination of release of $Ca^{2+}$ from intracellular stores, such as the endoplasmic reticulum (ER), and influx of $Ca^{2+}$ across the plasma membrane. In one example, cell activation begins with an agonist binding to a surface membrane receptor, which is coupled to phospholipase C (PLC) through a G-protein mechanism. PLC activation leads to the production of inositol 1,4,5-triphosphate ($IP_3$), which in turn activates the $IP_3$ receptor causing release of $Ca^{2+}$ from the ER. The fall in ER $Ca^{2+}$ then signals to activate plasma membrane store-operated calcium (SOC) channels.

Store-operated calcium (SOC) influx is a process in cellular physiology that controls such diverse functions such as, but not limited to, refilling of intracellular $Ca^{2+}$ stores (Putney et al. *Cell*, 75, 199-201, 1993), activation of enzymatic activity (Fagan et al., *J. Biol. Chem.* 275:26530-26537, 2000), gene transcription (Lewis, *Annu. Rev. Immunol.* 19:497-521, 2001), cell proliferation (Nunez et al., *J. Physiol.* 571.1, 57-73, 2006), and release of cytokines (Winslow et al., *Curr. Opin. Immunol.* 15:299-307, 2003). In some nonexcitable cells, e.g., blood cells, immune cells, hematopoietic cells, T lymphocytes and mast cells, SOC influx occurs through calcium release-activated calcium (CRAC) channels, a type of SOC channel.

The calcium influx mechanism has been referred to as store-operated calcium entry (SOCE). Stromal interaction molecule (STIM) proteins are an essential component of SOC channel function, serving as the sensors for detecting the depletion of calcium from intracellular stores and for activating SOC channels.

SUMMARY OF THE INVENTION

Described herein are compounds of Formula (I), compositions that include such compounds, and methods of use thereof, for modulating intracellular calcium. In another aspect, compounds of Formula (I) modulate intracellular calcium by inhibition of store operated calcium channel activity. In a further aspect, compounds of Formula (I) modulate intracellular calcium by preventing the activity of activated store operated calcium channel complexes. In one aspect, compounds of Formula (I) inhibit activation of store operated channels. In another aspect, compounds of Formula (I) inhibit activation of calcium-release activated calcium channels. In yet another aspect, compounds of Formula (I) modulate an activity of, modulate an interaction of, or modulate the level of, or distribution of, or bind to, or interact with at least one protein of the SOC channel complex. In one aspect, compounds of Formula (I) modulate an activity of, modulate an interaction of, or modulate the level of, or distribution of, or bind to, or interact with at least one protein of the CRAC channel complex. In one aspect, compounds of Formula (I) are selective inhibitors of CRAC channel activity.

In one aspect, described herein is a method of modulating intracellular calcium by inhibition of store operated calcium channel activity comprising administering a compound of Formula (I), or pharmaceutically acceptable salt, pharmaceutically acceptable solvate, or pharmaceutically acceptable prodrug thereof:

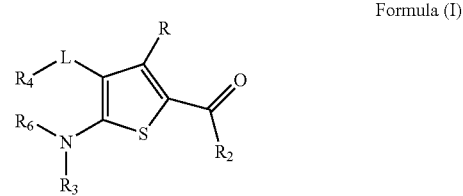

Formula (I)

wherein:
L is a bond, $C_1$-$C_6$alkyl, $C_1$-$C_6$alkenyl, $C_1$-$C_6$heteroalkyl, aryl, or heteroaryl; wherein $C_1$-$C_6$alkyl, $C_1$-$C_6$alkenyl, $C_1$-$C_6$heteroalkyl, aryl, or heteroaryl is optionally substituted with at least one $R_5$;

R is hydrogen, $CO_2R_1$, a carboxylic acid bioisostere, an optionally substituted heteroaryl, or an optionally substituted heterocycloalkyl;

$R_1$ is hydrogen, $C_1$-$C_6$alkyl, $C_1$-$C_6$cycloalkyl, $C_1$-$C_6$haloalkyl, phenyl or benzyl;

$R_2$ is cycloalkyl, aryl, arylalkyl, heteroaryl, heteroarylalkyl, heteroarylalkenyl, wherein cycloalkyl, aryl, arylalkyl, heteroaryl, heteroarylalkyl, heteroarylalkenyl is optionally substituted with at least one $R_5$;

$R_3$ and $R_6$ are each independently hydrogen $C_1$-$C_6$alkyl, —C(O)—$C_1$-$C_6$alkyl, —C(O)$NR_1$—$C_1$-$C_6$alkyl, wherein $C_1$-$C_6$alkyl is optionally substituted with at least one $R_5$; or $R_3$ and $R_6$ together with the nitrogen atom to which they are attached form a $C_2$-$C_8$heterocycloalkyl group optionally substituted with at least one $R_5$;

$R_4$ is aryl or heteroaryl; wherein aryl or heteroaryl is optionally substituted with at least one $R_5$;

each $R_5$ is independently selected from F, Cl, Br, I, —CN, alkyne, $C_1$-$C_6$ alkylalkyne, —$NO_2$, —OH, —$CF_3$, —$OCF_3$, —$OR_8$, $C_1$-$C_6$alkyl, $C_3$-$C_8$cycloalkyl, $C_1$-$C_6$heteroalkyl, $C_1$-$C_6$haloalkyl, tetrazolyl, $C_2$-$C_8$heterocycloalkyl, optionally substituted aryl, optionally substituted heteroaryl, —NHS(=O)$_2R_8$, —S(=O)$_2$N(R$_9$)$_2$, —N(R$_9$)S(=O)$_2$N(R$_9$)$_2$, —C(=O)CF$_3$, —C(=O)NHS(=O)$_2R_8$, —S(=O)$_2$NHC(=O)R$_8$, —N(R$_9$)$_2$, —N(R$_9$)C(=O)R$_8$, —N(R$_9$)C(=O)N(R$_9$)$_2$, —N(R$_9$)C(=O)OR$_8$, —CO$_2$R$_9$, —C(=O)R$_8$, —OC(=O)R$_8$, —OC(=O)N(R$_9$)$_2$, —CON(R$_9$)$_2$, —SR$_8$, —S(=O)R$_8$, and —S(=O)$_2R_8$;

each $R_8$ is independently selected from $C_1$-$C_6$alkyl, $C_1$-$C_6$haloalkyl, $C_3$-$C_8$cycloalkyl, phenyl, and benzyl; and each $R_9$ is independently selected from H, $C_1$-$C_6$alkyl, $C_1$-$C_6$haloalkyl, $C_3$-$C_8$cycloalkyl, phenyl, and benzyl.

Any combination of the groups described above for the various variables is contemplated herein.

In one aspect, described herein is a method of modulating store-operated calcium (SOC) channel activity comprising contacting the store-operated calcium (SOC) channel complex, or portion thereof, with a compound of Formula (I), or pharmaceutically acceptable salt, pharmaceutically acceptable solvate, or pharmaceutically acceptable prodrug thereof. In one embodiment, the contacting occurs in vitro. In another embodiment, the contacting occurs in vivo. In one embodiment, the compound of Formula (I) modulates an activity of, modulates an interaction of, or modulates the level of, or distributions of, or binds to, or interacts with at least one portion of the store operated calcium channel complex selected from stromal interaction molecules (STIM) family of proteins. In one embodiment, the compound of Formula (I) modulates an activity of, modulates an interaction of, or modulates the level of, or distributions of, or binds to, or interacts with at least one portion of STIM1 or STIM2. In one embodiment, modulating store operated calcium channel activity with a compound of Formula (I) inhibits store-operated calcium entry (SOCE). In another embodiment, the store operated calcium channel complex is calcium-release activated calcium (CRAC) channel complex. In one embodiment, modulating calcium release activated calcium (CRAC) activity with a compound of Formula (I) inhibits the electrophysiological current ($I_{CRAC}$) directly associated with activated CRAC channels.

In another aspect, described herein is a method of modulating calcium release activated calcium channel (CRAC) activity in a mammal comprising administering a compound of Formula (I), or pharmaceutically acceptable salt, pharmaceutically acceptable solvate, or pharmaceutically acceptable prodrug thereof. In one embodiment, the compound of Formula (I) modulates an activity of, modulates an interaction of, or modulates the level of, or distributions of, or binds to, or interacts with at least one component of the calcium release activated (CRAC) channel complex selected from stromal interaction molecules (STIM) family of proteins. In one embodiment, the compound of Formula (I) modulates an activity of, modulates an interaction of, or modulates the level of, or distributions of, or binds to, or interacts with STIM1 or STIM2. In one embodiment, modulating calcium release activated calcium (CRAC) channel activity with a compound of Formula (I) inhibits store-operated calcium entry (SOCE). In one embodiment, modulating calcium release activated calcium (CRAC) channel activity with a compound of Formula (I) inhibits the electrophysiological current ($I_{CRAC}$) directly associated with activated CRAC channels. In one embodiment, the compound of Formula (I) inhibits SOCE with an $IC_{50}$ below about 10 µM. In yet another embodiment, the compound of Formula (I) inhibits electrophysiological current (ICRAC) directly associated with activated CRAC channels at a concentration below about 10 µM.

Also described herein is a method of treating a disease, disorder or condition in a mammal that would benefit from inhibition of store operated calcium channel activity comprising administering to the mammal a compound of Formula (I), or pharmaceutically acceptable salt, pharmaceutically acceptable solvate, or pharmaceutically acceptable prodrug thereof. In one aspect, the compound of Formula (I) modulates the activity of, modulates an interaction of, or binds to, or interacts with a mammalian STIM1 protein, or a mammalian STIM2 protein. In one embodiment, the disease, disorder or condition in a mammal is selected from diseases/disorders involving inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, organ transplant rejection, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, psoriasis, multiple sclerosis, Sjogren's syndrome, cancer and other proliferative diseases, and autoimmune diseases or disorders. In yet another embodiment, the method further comprises administering to the mammal a second therapeutic agent. In one embodiment, the second therapeutic agent is selected from immunosuppressants, glucocorticoids, non-steroidal anti-inflammatory drugs, Cox-2-specific inhibitors, leflunomide, gold thioglucose, gold thiomalate, aurofin, sulfasalazine, hydroxychloroquinine, minocycline, anti-TNF-α agents, abatacept, anakinra, interferon-β, interferon-γ, interleukin-2, allergy vaccines, antihistamines, antileukotrienes, beta-agonists, theophylline, and anticholinergics. In another embodiment, the second therapeutic agent is selected from tacrolimus, cyclosporin, rapamicin, methotrexate, cyclophosphamide, azathioprine, mercaptopurine, mycophenolate, or FTY720, prednisone, cortisone acetate, prednisolone, methylprednisolone, dexamethasone, betamethasone, triamcinolone, beclometasone, fludrocortisone acetate, deoxycorticosterone acetate, aldosterone, aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502, JTE-522, L-745,337 and NS398, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, allergy vaccines, antihistamines, antileukotrienes, beta-agonists, theophylline, and anticholinergics.

Also described herein is a method of inhibiting store-operated calcium entry (SOCE) activation of nuclear factor of activated T cells (NFAT) in a mammal comprising administering a compound of Formula (I), or pharmaceutically acceptable salt, pharmaceutically acceptable solvate, or pharmaceutically acceptable prodrug thereof. In one embodiment, the compound of Formula (I) modulates an interaction of, or modulates the level of, or distributions of, or binds to, or interacts with a mammalian STIM1 protein, or a mammalian STIM2 protein.

Also provided herein is a method of decreasing cytokine expression by inhibiting the store-operated calcium entry activation of NFAT in a mammal comprising administering a compound of Formula (I), or pharmaceutically acceptable salt, pharmaceutically acceptable solvate, or pharmaceutically acceptable prodrug thereof. In one embodiment, the compound of Formula (I) modulates an interaction of, or modulates the level of, or distributions of, or binds to, or interacts with a mammalian STIM1 protein or a mammalian STIM2 protein. In one embodiment, the cytokine is selected from IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, IL-1 RA, granulocyte colony stimulating factor (G-CSF), granulocyte-macrophage colony stimulating factor (GM-CSF), oncostatin M, erythropoietin, leukemia inhibitory factor (LIF), interferons, gamma-interferon (γ-IFN), B7.1 (CD80), B7.2 (B70, CD86), TNF-α, TNF-β, LT-β, CD40 ligand, Fas ligand, CD27 ligand, CD30 ligand, 4-1BBL, Trail, and migration inhibitory factor (MIF).

In one aspect, described herein is the use of a compound of Formula (I), or pharmaceutically acceptable salt, pharmaceutically acceptable solvate, or pharmaceutically acceptable prodrug thereof, for the formulation of a medicament for the modulation of store operated calcium (SOC) channel activity in a subject or for the treatment of a disease, disorder or condition in a subject that would benefit from the modulation of store operated calcium (SOC) channel activity. In one embodiment, the compound of Formula (I) inhibits store operated calcium entry (SOCE). In another embodiment, the store operated calcium channel activity is calcium release activated calcium channel activity.

Also described is an article of manufacture, comprising packaging material, a compound of Formula (I), or composition, or pharmaceutically acceptable salt, pharmaceutically acceptable prodrug, or pharmaceutically acceptable solvate thereof, which is effective for inhibiting calcium release-activated calcium (CRAC) channel activity, or for the treatment, prevention or amelioration of one or more symptoms of a disease, disorder or condition that would benefit from the inhibition of calcium release-activated calcium (CRAC) channel activity, within the packaging material, and a label that indicates that the compound or composition, or pharmaceutically acceptable salt, pharmaceutically acceptable prodrug, or pharmaceutically acceptable solvate thereof, is used for the inhibition of calcium release-activated calcium (CRAC) channel activity, or for the treatment, prevention or amelioration of one or more symptoms of a disease, disorder or condition that would benefit from the inhibition of calcium release-activated calcium (CRAC) channel activity. In one embodiment, the compound of Formula (I) inhibits store operated calcium entry (SOCE).

In one aspect, described herein is a pharmaceutical composition comprising a pharmaceutically acceptable diluent, excipient or binder, and a compound of Formula (I), or pharmaceutically acceptable salt, pharmaceutically acceptable prodrug, or pharmaceutically acceptable solvate thereof.

In one embodiment, provided herein is a pharmaceutical composition, which includes an effective amount of a compound provided herein, and a pharmaceutically acceptable excipient. In a further embodiment, provided are compositions further including a second pharmaceutically active ingredient.

In certain embodiments, provided herein is a pharmaceutical composition containing: i) a physiologically acceptable carrier, diluent, and/or excipient; and ii) one or more compounds described herein.

In any of the aforementioned aspects are further embodiments that include single administrations of the effective amount of the compound of Formula (I), including further embodiments in which: (i) the compound of Formula (I) is administered once; (ii) the compound of Formula (I) is administered to the mammal multiple times over the span of one day; (iii) continually; or (iv) continuously.

In any of the aforementioned aspects are further embodiments that include multiple administrations of the effective amount of the compound of Formula (I), including further embodiments in which (i) the compound of Formula (I) is administered in a single dose; (ii) the time between multiple administrations is every 6 hours; (iii) the compound of Formula (I) is administered to the mammal every 8 hours. In further embodiments, the method comprises a drug holiday, wherein the administration of the compound of Formula (I) is temporarily suspended or the dose of the compound of Formula (I) being administered is temporarily reduced; at the end of the drug holiday, dosing of the compound of Formula (I) is resumed. In some embodiments, the length of the drug holiday varies from 2 days to 1 year.

In one embodiment, compounds of Formula (I) described herein are administered to a human. In some embodiments, compounds of Formula (I) described herein are orally administered.

Compounds provided herein are used for modulating intracellular calcium. In one embodiment, compounds provided herein modulate SOC channel activity. In one embodiment, compounds provided herein modulate CRAC channel activity. In another embodiment, compounds provided herein modulate STIM protein activity. In another embodiment, compounds provided herein modulate Orai protein activity. In another embodiment, compounds provided herein modulate the functional interactions of STIM proteins with Orai proteins. In another embodiment, compounds provided herein reduce the number of functional SOC channels. In another embodiment, compounds provided herein reduce the number of functional CRAC channels. In one embodiment, compounds described herein are SOC channel blockers. In one embodiment, compounds described herein are CRAC channel blockers.

In one embodiment, compounds of Formula (I) are inhibitors of SOCE. In one embodiment, compounds of Formula (I) are selective inhibitors of CRAC channel activity.

Other objects, features and advantages of the compounds, compositions, methods, and uses described herein will become apparent from the following detailed description. It should be understood, however, that the detailed description and the specific examples, while indicating specific embodiments, are given by way of illustration only.

DETAILED DESCRIPTION

Figure 1:
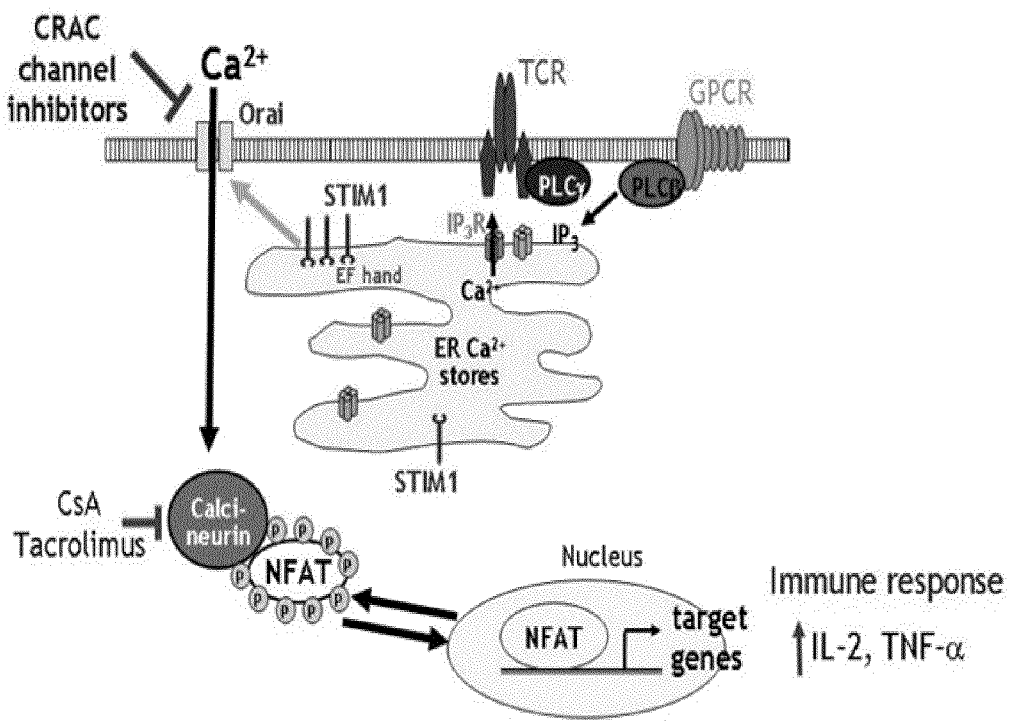
FIG. 1 outlines the $I_{CRAC}$ channel pathway

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endolasmic reticulum, the sarcoplasmic reticulum, mitochondria and endocytic organelles including endosomes and lysosomes.

Movement of calcium across cellular membranes is carried out by specialized proteins. For example, calcium from the extracellular space can enter the cell through various calcium channels and a sodium/calcium exchanger and is actively extruded from the cell by calcium pumps and sodium/calcium exchangers. Calcium can also be released from internal stores through inositol trisphosphate or ryanodine receptors and can be taken up by these organelles by means of calcium pumps.

Calcium can enter cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ can enter cells via $Na^+$—$Ca^{2+}$ exchangers operating in reverse mode.

Endocytosis provides another process by which cells take up calcium from the extracellular medium through endosomes. In addition, some cells, e.g., exocrine cells, can release calcium via exocytosis.

Cytosolic calcium concentration is tightly regulated with resting levels usually estimated at approximately 0.1 µM in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leak pathways in both the endoplasmic reticulum and plasma membrane. Disturbance of resting cytosolic calcium levels can affect transmission of calcium dependent signals and give rise to defects in a number of cellular processes. For example, cell proliferation involves a prolonged calcium signaling sequence. Other cellular processes that involve calcium signaling include, but are not limited to, secretion, transcription factor signaling, and fertilization, involve calcium signaling.

Cell-surface receptors that activate phospholipase C(PLC) create cytosolic $Ca^{2+}$ signals from intra- and extra-cellular sources. An initial transient rise of $[Ca^2]_i$ (intracellular calcium concentration) results from the release of $Ca^{2+}$ from the endoplasmic reticulum (ER), which is triggered by the PLC product, inositol-1,4,5-trisphosphate ($IP_3$), opening $IP_3$ receptors in the ER (Streb et al. Nature, 306, 67-69, 1983). A subsequent phase of sustained $Ca^{2+}$ entry across the plasma membrane then ensues, through specialized store operated calcium (SOC) channels (in the case of immune cells the SOC channels are calcium release-activated calcium (CRAC) channels) in the plasma membrane. Store-operated $Ca^{2+}$ entry (SOCE) is the process in which the emptying of $Ca^{2+}$ stores itself activates $Ca^{2+}$ channels in the plasma membrane to help refill the stores (Putney, Cell Calcium, 7, 1-12, 1986; Parekh et al., Physiol. Rev. 757-810; 2005). SOCE does more than simply provide $Ca^{2+}$ for refilling stores, but can itself generate sustained $Ca^{2+}$ signals that control such essential functions as gene expression, cell metabolism and exocytosis (Parekh and Putney, Physiol. Rev. 85, 757-810 (2005).

In lymphocytes and mast cells, activation of antigen or Fc receptors respectively causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programmes depending on stimulation conditions and cell type. In response to infections and during transplant rejection, NFAT partners with the transcription factor AP-1 (Fos-Jun) in the nucleus of "effector" T cells, thereby transactivating cytokine genes, genes that regulate T cell proliferation and other genes that orchestrate an active immune response (Rao et al., Annu Rev Immunol., 1997; 15:707-47). In contrast, in T cells recognizing self antigens, NFAT is activated in the absence of AP-1, and activates a transcriptional programme known as "anergy" that suppresses autoimmune responses (Macian et al., Transcriptional mechanisms underlying lymphocyte tolerance. Cell. 2002 Jun. 14; 109(6):719-31). In a subclass of T cells known as regulatory T cells which suppress autoimmunity mediated by self-reactive effector T cells, NFAT partners with the transcription factor FOXP3 to activate genes responsible for suppressor function (Wu et al., Cell, 2006 Jul. 28; 126(2):375-87; Rudensky AY, Gavin M, Zheng Y. Cell. 2006 Jul. 28; 126(2):253-256).

The endoplasmic reticulum (ER) carries out a variety processes. The ER has a role as both a $Ca^{2+}$ sink and an agonist-sensitive $Ca^{2+}$ store, and protein folding/processing takes place within its lumen. In the latter case, numerous $Ca^{2+}$-dependent chaperone proteins ensure that newly synthesized proteins are folded correctly and sent off to their appropriate destination. The ER is also involved in vesicle trafficking, release of stress signals, regulation of cholesterol metabolism, and apoptosis. Many of these processes require intraluminal $Ca^{2+}$, and protein misfolding, ER stress responses, and apoptosis can all be induced by depleting the ER of $Ca^{2+}$ for prolonged periods of time. Because it contains a finite amount of $Ca^{2+}$, it is clear that ER $Ca^{2+}$ content must fall after release of that $Ca^{2+}$ during stimulation. However, to preserve the functional integrity of the ER, it is vital that the $Ca^{2+}$ content does not fall too low, or is maintained at least at a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store operated calcium entry was provided by electrophysiological studies which established that the process of emptying the stores activated a $Ca^{2+}$ current in mast cells called $Ca^{2+}$ release-activated $Ca^{2+}$ current or $I_{CRAC}$. $I_{CRAC}$ is non-voltage activated, inwardly rectifying, and remarkably selective for $Ca^{2+}$. It is found in several cell types mainly of hemapoietic origin. $I_{CRAC}$ is not the only store-operated current, and it is now apparent that store-operated influx encompasses a family of $Ca^{2+}$-permeable channels, with different properties in different cell types. $I_{CRAC}$ was the first store-operated $Ca^{2+}$ current to be described and remains a popular model for studying store-operated influx.

Store-operated calcium channels can be activated by any procedure that empties the ER $Ca^{2+}$ stores; it does not seem to matter how the stores are emptied, the net effect is activation of store-operated $Ca^{2+}$ entry. Physiologically, store emptying is evoked by an increase in the levels of $IP_3$ or other $Ca^{2+}$-releasing signals followed by $Ca^{2+}$ release from the stores. But there are several other methods for emptying stores. These methods include the following:
1) elevation of $IP_3$ in the cytosol (following receptor stimulation or, dialyzing the cytosol with $IP_3$ itself or related congeners like the nonmetabolizable analog $Ins(2,4,5)P_3$);
2) application of the $Ca^{2+}$ ionophore ionomycin to permeabilize the ER membrane;

3) dialyzing the cytoplasm with high concentrations of the $Ca^{2+}$ chelators EGTA or BAPTA, which chelate $Ca^{2+}$ that leaks from the stores and hence prevent store refilling;
4) exposure to the sarcoplasmic/endoplasmic reticulum $Ca^{2+}$-ATPase (SERCA) inhibitors like thapsigargin, cyclopiazonic acid, and di-tert-butylhydroquinone;
5) sensitizing the $IP_3$ receptors to resting levels of $InsP_3$ with agents like thimerosal; and
6) loading membrane-permeable metal $Ca^{2+}$ chelators like N,N,N',N'-tetrakis(2-pyridylmethyl)ethylene diamine (TPEN) directly into the stores.

Through mass action, TPEN lowers free intraluminal $Ca^{2+}$ concentration without changing total store $Ca^{2+}$ such that the store depletion-dependent signal is generated.

These methods of emptying stores are not devoid of potential problems. The key feature of store-operated $Ca^{2+}$ entry is that it is the fall in $Ca^{2+}$ content within the stores and not the subsequent rise in cytoplasmic $Ca^{2+}$ concentration that activates the channels. However, ionomycin and SERCA pump blockers generally cause a rise in cytoplasmic $Ca^{2+}$ concentration as a consequence of store depletion, and such a rise in $Ca^{2+}$ could open $Ca^{2+}$-activated cation channels permeable to $Ca^{2+}$. One way to avoid such problems is to use agents under conditions where cytoplasmic $Ca^{2+}$ has been strongly buffered with high concentrations of $Ca^{2+}$ chelator such as EGTA or BAPTA.

Store-Operated Calcium Entry

Reduced calcium concentration in intracellular calcium stores such as the endoplasmic reticulum resulting from release of calcium therefrom provides a signal for influx of calcium from the extracellular medium into the cell. This influx of calcium, which produces a sustained "plateau" elevation of cytosolic calcium concentration, generally does not rely on voltage-gated plasma membrane channels and does not involve activation of calcium channels by calcium. This calcium influx mechanism is referred to as capacitative calcium entry (CCE), calcium release-activated, store-operated or depletion-operated calcium entry. Store-operated calcium entry can be recorded as an ionic current with distinctive properties. This current is referred to as $I_{SOC}$ (store-operated current) or $I_{CRAC}$ (calcium release-activated current).

Electrophysiological analysis of store-operated or calcium release-activated currents reveals distinct biophysical properties of these currents. For example, the current are activated by depletion of intracellular calcium stores (e.g., by non-physiological activators such as thapsigargin, CPA, ionomycin and BAPTA, and physiological activators such as $IP_3$) and can be selective for divalent cations, such as calcium, over monovalent ions in physiological solutions or conditions, can be influenced by changes in cytosolic calcium levels, and can show altered selectivity and conductivity in the presence of low extracellular concentrations of divalent cations. The current may also be blocked or enhanced by 2-APB (depending on concentration) and blocked by SKF96365 and $Gd^{3+}$ and generally are described as a calcium current that is not strictly voltage-gated.

Patch-clamp studies in mast cells and Jurkat leukaemic T cells have established the CRAC entry mechanism as an ion channel with distinctive biophysical characteristics, including a high selectivity for $Ca^{2+}$ paired with an exceedingly low conductance. Furthermore, the CRAC channel was shown to fulfill the rigorous criteria for being store-operated, which is the activation solely by the reduction of $Ca^{2+}$ in the ER rather than by cytosolic $Ca^{2+}$ or other messengers generated by PLC.

Regulation of Store-Operated Calcium Entry by Intracellular Calcium Stores

Store-operated calcium entry is regulated by the level of calcium within an intracellular calcium store. Intracellular calcium stores are characterized by sensitivity to agents, which are physiological or pharmacological, which activate release of calcium from the stores or inhibit uptake of calcium into the stores. Different cells have been studied in characterization of intracellular calcium stores, and stores have been characterized as sensitive to various agents, including, but not limited to, $IP_3$ and compounds that affect the $IP_3$ receptor, thapsigargin, ionomycin and/or cyclic ADP-ribose (cADPR).

Accumulation of calcium within endoplasmic reticulum and sarcoplasmic reticulum (SR; a specialized version of the endoplasmic reticulum in striated muscle) storage organelles is achieved through sarcoplasmic-endoplasmic reticulum calcium ATPases (SERCAs), commonly referred to as calcium pumps. During signaling (i.e., when endoplasmic reticulum channels are activated to provide for calcium release from the endoplasmic reticulum into the cytoplasm), endoplasmic reticulum calcium is replenished by the SERCA pump with cytoplasmic calcium that has entered the cell from the extracellular medium.

Calcium release channels associated with $IP_3$ and ryanodine receptors provide for controlled release of calcium from endoplasmic and sarcoplasmic reticulum into the cytoplasm resulting in transient increases in cytoplasmic calcium concentration. $IP_3$ receptor-mediated calcium release is triggered by $IP_3$ formed in the break down of plasma membrane phosphoinositides through the action of phospholipase C which is activated by binding of an agonist to a plasma membrane G protein-coupled receptor or tyrosine kinase. Ryanodine receptor-mediated calcium release is triggered by an increase in cytoplasmic calcium and is referred to as calcium-induced calcium release (CICR). The activity of ryanodine receptors (which have affinity for ryanodine and caffeine) may also be regulated by cyclic ADP-ribose.

Thus, the calcium levels in the stores, and in the cytoplasm, fluctuate. For example, ER free calcium can decrease from a range of about 60 to about 400 µM to about 1 to about 50 µM when HeLa cells are treated with histamine, an agonist of PLC-linked histamine receptors (Miyawaki et al. (1997) *Nature* 388:882-887). Store-operated calcium entry is activated as the free calcium concentration of the intracellular stores is reduced. Depletion of store calcium, as well as a concomitant increase in cytosolic calcium concentration, can thus regulate store-operated calcium entry into cells.

Cytoplasmic Calcium Buffering

Agonist activation of signaling processes in cells can involve dramatic increases in the calcium permeability of the endoplasmic reticulum, for example, through opening of $IP_3$ receptor channels, and the plasma membrane through store-operated calcium entry. These increases in calcium permeability are associated with an increase in cytosolic calcium concentration that can be separated into two components: a "spike" of calcium release from the endoplasmic reticulum during activation of the $IP_3$ receptor and a plateau phase which is a sustained elevation of calcium levels resulting from entry of calcium into the cytoplasm from the extracellular medium. Upon stimulation, the resting intracellular free calcium concentration of about 100 nM can rise globally to greater than 1 µM and higher in microdomains of the cell. The cell modulates these calcium signals with endogenous calcium buffers, including physiological buffering by organelles such as mitochondria, endoplasmic reticulum and Golgi. Mitochondrial uptake of calcium through a uniporter in the inner membrane is driven by the large negative mitochondrial membrane potential, and the accumulated calcium is released slowly through sodium-dependent and -independent exchangers, and, under some circumstances, the permeability transition pore (PTP). Thus, mitochondria can act as calcium buffers by taking up calcium during periods of cellular activation and can slowly releasing it later. Uptake of calcium into the endoplasmic reticulum is regulated by the sarcoplasmic and endoplasmic reticulum calcium ATPase (SERCA). Uptake of calcium into the Golgi is mediated by a P-type calcium transport ATPase (PMR1/ATP2C1). Additionally, there is evidence that a significant amount of the calcium released upon $IP_3$ receptor activation is extruded from the cell through the action of the plasma membrane calcium ATPase. For example, plasma membrane calcium ATPases provide the dominant mechanism for calcium clearance in human T cells and Jurkat cells, although sodium/calcium exchange also contributes to calcium clearance in human T cells. Within calcium-storing organelles, calcium ions can be bound to specialized calcium-buffering proteins, such as, for example, calsequestrins, calreticulins and calnexins. Additionally, there are calcium-buffering proteins in the cytosol that modulate calcium spikes and assist in redistribution of calcium ions. Thus, proteins and other molecules that participate in any of these and other mechanisms through which cytosolic calcium levels can be reduced are proteins that are involved in, participate in and/or provide for cytoplasmic calcium buffering. Thus, cytoplasmic calcium buffering allows forhelps regulate cytoplasmic $Ca^{2+}$ levels during periods of sustained calcium influx through SOC channels or bursts of $Ca^{2+}$ release. Large increases in cytoplasmic $Ca^{2+}$ levels or store refilling deactivate SOCE.

Downstream Calcium Entry-Mediated Events

In addition to intracellular changes in calcium stores, store-operated calcium entry affects a multitude of events that are consequent to or in addition to the store-operated changes. For example $Ca^{2+}$ influx results in the activation of a large number of calmodulin-dependent enzymes including the serine phosphatase calcineurin. Activation of calcineurin by an increase in intracellular calcium results in acute secretory processes such as mast cell degranulation. Activated mast cells release preformed granules containing histamine, heparin, TNFα and enzymes such as β-hexosaminidase. Some cellular events, such as B and T cell proliferation, require sustained calcineurin signaling, which requires a sustained increase in intracellular calcium. A number of transcription factors are regulated by calcineurin, including NFAT (nuclear factor of activated T cells), MEF2 and NFκB. NFAT transcription factors play important roles in many cell types, including immune cells. In immune cells NFAT mediates transcription of a large number of molecules, including cytokines, chemokines and cell surface receptors. Transcriptional elements for NFAT have been found within the promoters of cytokines such as IL-2, IL-3, IL-4, IL-5, IL-8, IL-13, as well as tumor necrosis factor alpha (TNFα), granulocyte colony-stimulating factor (G-CSF), and gamma-interferon (γ-IFN).

The activity of NFAT proteins is regulated by their phosphorylation level, which in turn is regulated by both calcineurin and NFAT kinases. Activation of calcineurin by an increase in intracellular calcium levels results in dephosphorylation of NFAT and entry into the nucleus. Rephosphorylation of NFAT masks the nuclear localization sequence of NFAT and prevents its entry into the nucleus. Because of its strong dependence on calcineurin-mediated dephosphorylation for localization and activity, NFAT is a sensitive indicator of free intracellular calcium levels.

Diseases, Disorders or Conditions

Clinical studies demonstrate that the CRAC channel is required for the activation of genes underlying the T cell response to antigen. Sustained calcium entry is needed for lymphocyte activation and adaptive immune response. Calcium entry into lymphocytes occurs primarily through the CRAC channels. Increased calcium leads to NFAT activation and expression of cytokines required for immune response Inhibiting the store operated calcium entry is an efficient way to prevent T cell activation.

Inhibition of CRAC channel activity with the compounds described herein, such as compounds of Formula (I), provide a means for providing immunosuppresive therapy as demonstrated by the elimination of store-operated calcium entry noted in patients with severe-combined immunodeficiency (SCID). T cells, fibroblasts, and in some cases B cells, from patients with T cell immunodeficiency or SCID having a principal defect in T cell activation show a strong defect in store-operated calcium entry. SCID patients lack adaptive immune response, but without any impairment or toxicity in major organs. The SCID patient phenotype indicates that inhibition of CRAC channels is an effective strategy for immunosuppression.

Diseases/Disorders Involving Inflammation and Diseases/Disorders Related to the Immune System In some embodiments, diseases, disorders or conditions that are treated or prevented using the compounds, compositions, and methods provided herein include diseases, conditions or disorders involving inflammation and/or that are related to the immune system. These diseases include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration. Store-operated calcium influx in particular is thought to play an important role in PMN activation. It has been shown that trauma increases PMN store-operated calcium influx and that prolonged elevations of cytosolic calcium concentration due to enhanced store-operated calcium influx may alter stimulus-response coupling to chemotaxins and contribute to PMN dysfunction after injury. Modulation of PMN cytosolic calcium concentration through store-operated calcium channels might therefore be useful in regulating PMN-mediated inflammation and spare cardiovascular function after injury, shock or sepsis.

Calcium plays a critical role in lymphocyte activation. Activation of lymphocytes, e.g., by antigen stimulation, results in rapid increases in intracellular free calcium concentrations and activation of transcription factors, including nuclear factor of activated T cells (NFAT), NF-κB, JNK1, MEF2 and CREB. NFAT is a key transcriptional regulator of the IL-2 (and other cytokine) genes. A sustained elevation of intracellular calcium level is required to keep NFAT in a transcriptionally active state, and is dependent on store-operated calcium entry. Reduction or blocking of store-operated calcium entry in lymphocytes blocks calcium-dependent lymphocyte activation. Thus, in some embodiments, modulation of intracellular calcium, and particularly store-operated calcium entry (e.g., reduction in, elimination of store-operated calcium entry), in lymphocytes is a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. For example, in some embodiments treatment of an autoimmune disease/disorder involves reducing, blocking or eliminating store-operated calcium entry in lymphocytes.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Cancer and Other Proliferative Diseases

In other embodiments, compounds of Formula (I), compositions thereof, and methods provided herein are used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. Store-operated calcium entry is thought to play an important role in cell proliferation in cancer cells.

Inhibition of SOCE is sufficient to prevent tumor cell proliferation. The pyrazole derivative BTP-2, a direct $I_{CRAC}$ blocker inhibits SOCE and proliferation in Jurkat cells and in colon cancer cells. It has been suggested that sustained SOCE requires mitochondrial $Ca^{2+}$ uptake and that prevention of mitochondrial $Ca^{2+}$ uptake leads to SOCE inhibition. Stimulation of Jurkat cells induces sustained SOCE and activation of the $Ca^{2+}$-dependent phosphatase calcineurin that dephosphorylates NFAT, promoting expression of interleukin-2 and proliferation. In other embodiments, compounds of Formula (I) inhibit SOCE and are used in the treatment of cancer or other proliferative diseases or conditions.

Liver Diseases and Disorders

In some embodiments, diseases, disorders or conditions that are treated or prevented using the compounds of Formula (I), compositions thereof, and methods provided herein include hepatic or liver diseases and disorders. These diseases, conditions or disorders include but are not limited to liver injury, for example, due to transplantation, hepatitis and cirrhosis.

Store-operated calcium entry has been implicated in chronic liver disease as well as transplantation injury after cold preservation-warm reoxygenation.

Kidney Diseases and Disorders

In some embodiments, diseases, conditions or disorders that are treated or prevented using the methods provided herein include kidney or renal diseases and disorders. Mesangial cell hyperplasia is often a key feature of such diseases and disorders. In other embodiments, such diseases and disorders are caused by immunological or other mechanisms of injury, including IgAN, membranoproliferative glomerulonephritis or lupus nephritis. Imbalances in the control of mesangial cell replication also appear to play a key role in the pathogenesis of progressive renal failure.

The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis can result. Data have indicated that regulators of mesangial cell growth, particularly growth factors, are thought to act by regulating store-operated calcium channels. In yet other embodiments, modulators of store-operated calcium influx aids in the treatment of glomerular diseases by inhibiting mesangial cell proliferation.

Store Operated Calcium Channels

Clinical studies demonstrate that the CRAC channel, a type of SOC channel, is required for the activation of genes underlying the T cell response to antigen (Partiseti et al., *J Biol. Chem.*, 269, 32327-32335, 1994; Feske et al., *Curr. Biol.* 15, 1235-1241, 2005). In some embodiments, SOCE contributes directly to the elevation of cytosolic $Ca^{2+}$ levels ($[Ca^{2+}]_i$), as in T lymphocytes where CRAC channels generate the sustained $Ca^{2+}$ signals needed to drive gene expression underlying T cell activation by antigen. Sustained calcium entry is needed for lymphocyte activation and adpative immune response. Calcium entry into lymphocytes occurs primarily through the CRAC channels. Increased calcium levels lead to NFAT activation and expression of cytokines required for immune response.

The CRAC channel has a distinctive biophysical fingerprint, quantifiable store-dependence, and essential function in T cells. Studies have shown that CRAC channels are formed from two component proteins, which interact to form CRAC channels. The CRAC channel is assembled by two functional components, STIM1 and Orai1. STIM1 (stromal interaction molecule 1) was identified as the mammalian ER $Ca^{2+}$ sensor. Orai1/CRACM1 was identified as a component of the mammalian CRAC channel.

STIM1 is the sensor of $Ca^{2+}$ within ER $Ca^{2+}$ stores, moving in response to store depletion into ER puncta close to the plasma membrane. Orai1 is a pore forming CRAC channel subunit in the plasma membrane. The two membrane proteins STIM1 and Orai1 have each been shown to be essential for the activation of CRAC channels.

Expression of both STIM1 and Orai1 in human embryonic kidney 293 cells (HEK293 cells) reconstitute functional CRAC channels. Expression of Orai1 alone strongly reduces store-operated $Ca^{2+}$ entry in HEK293 cells and the $Ca^{2+}$ release-activated $Ca^{2+}$ current ($I_{CRAC}$) in rat basophilic leukemia cells. However, expressed along with the store-sensing STIM1 protein, Orai1 causes a massive increase in SOCE, enhancing the rate of $Ca^{2+}$ entry by up to 103-fold. This entry is entirely store dependent since the same coexpression causes no measurable store-independent $Ca^{2+}$ entry. The entry is completely blocked by the store operated channel blocker, 2-aminoethoxydiphenylborate. STIM proteins are known to mediate $Ca^{2+}$ store-sensing and endoplasmic reticulum-plasma membrane coupling with no intrinsic channel properties. Orai1 contributes the plasma membrane channel component responsible for $Ca^{2+}$ entry. The suppression of CRAC channel function by Orai1 overexpression reflects a required stoichiometry between STIM1 and Orai1.

Stromal Interacting Molecule (STIM) Proteins

In an RNAi screen in *Drosophila* S2 cells using thapsigargin-activated $Ca^{2+}$ entry as a marker for store-operated channels, one gene gave a substantially reduced $Ca^{2+}$ entry, and that gene coded coding for the protein stromal interaction molecule (Stim) (Roos, J. et al. *J. Cell Biol.* 169, 435-445, 2005). There are two homologues of Stim in mammalian cells, STIM1 and STIM2, both of which appear to be distributed ubiquitously (Williams et al., *Biochem J.* 2001 Aug. 1; 357(Pt 3):673-85). STIM1 is the ER $Ca^{2+}$ sensor for store-operated $Ca^{2+}$ entry. STIM1 is a 77 kDa type I membrane protein with multiple predicted protein interaction or signaling domains and is located predominantly in the ER, but also to a limited extent in the plasma membrane.

Knockdown of STIM1 by RNAi substantially reduced $I_{CRAC}$ in Jurkat T cells, and store-operated $Ca^{2+}$ entry in HEK293 epithelial cells and SH-SY5Y neuroblastoma cells. However, knockdown of the closely related STIM2 had no effect. These results indicate an essential role of STIM (Drosophila) and STIM1 (mammals) in the mechanism of activation of store-operated channels. It is unlikely that STIM1 is the store-operated channel itself. It has no channel-like sequence, and overexpression of the protein only modestly enhances $Ca^{2+}$ entry. STIM1 is located both on the plasma membrane and intracellular membranes, like the ER. The protein sequence suggests that it spans the membrane once, with its $NH_2$ terminus oriented toward the lumen of the ER or the extracellular space. The $NH_2$ terminus contains an EF-hand domain, and functions as the $Ca^{2+}$ sensor in the ER. The protein also contains protein-protein interaction domains, notably coiled-coiled domains in the cytoplasm and a sterile motif (SAM) in the ER (or extracellular space), both near the predicted transmembrane domain. STIM1 can oligomerize and thus the protein in the ER and plasma membrane could interact bridging the two.

Total internal reflection fluorescence (TIRF) and confocal microscopy reveal that STIM1 is distributed throughout the ER when $Ca^{2+}$ stores are full, but redistributes into discrete puncta near the plasma membrane on store depletion. Although the redistribution of STIM1 into junctional ER regions is slow, it does precede the opening of CRAC channels by several and is therefore rapid enough to be an essential step in the activation of CRAC channels.

It has been suggested that store depletion causes the insertion of STIM1 into the plasma membrane where it may control store operated calcium entry through the CRAC channels.

Evidence for STIM1 as the $Ca^{2+}$ sensor for SOCE is that mutation of predicted $Ca^{2+}$-binding residues of the EF hand structural motif, expected to reduce its affinity for $Ca^{2+}$ and hence mimic the store-depleted state, causes STIM1 to redistribute spontaneously into puncta and trigger constitutive $Ca^{2+}$ influx through SOCs even when stores are full.

Orai Proteins

Orai1 (also known as CRACM1) is a widely expressed, 33 kDa plasma membrane protein with 4 transmembrane domains and a lack of significant sequence homology to other ion channels.

Studies of T cells from human patients with a severe combined immunodeficiency (SCID) syndrome, in which T cell receptor engagement or store depletion failed to activate $Ca^{2+}$ entry, was shown to be due to a single point mutation in Orai1.

Other mammalian Orai homologues exist, e.g. Orai2 and Orai3, however their function is not clearly defined. Orai2 and Orai3 can exhibit SOC channel activity when overexpressed with STIM1 in HEK cells.

Evidence that Orai1 contributes to the CRAC channel pore was obtained by Orai1 mutagenesis studies. Selectivity of the CRAC channel for $Ca^{2+}$ ions was shown by mutations at either Glu 106 or Glu 190, which weaken the ability of $Ca^{2+}$ binding in order block permeation of monovalent cations (similar to mechanisms described for voltage-gated $Ca^{2+}$ channels).

Neutralizing the charge on a pair of aspartates in the I-II loop (Asp 110 and Asp 112) reduces block by $Gd^{3+}$ and block of outward current by extracellular $Ca^{2+}$, indicating that these negatively charged sites may promote accumulation of polyvalent cations near the mouth of the pore.

Currents observed through overexpression of Orai1 closely resemble $I_{CRAC}$, and the fact that Orai1 can form multimers, makes it likely that the native CRAC channel is either a multimer of Orai1 alone or in combination with the closely related subunits Orai2 and/or Orai3.

Functional Store Operated Calcium Channels

The characterization of SOC channels has been largely obtained by one type of SOC channel, the CRAC channel. CRAC channel activity is triggered by the loss of $Ca^{2+}$ from the ER lumen, which is coupled to the opening of CRAC channels in the plasma membrane through the actions of STIM1 and Orai1. Depletion of $Ca^{2+}$ is sensed by STIM1, causing it to accumulate in junctional ER adjacent to the plasma membrane. In a TIRF-based $Ca^{2+}$-imaging study to map the locations of open CRAC channels, $[Ca^{2+}]_i$ elevations were seen to co-localize with STIM1 puncta, showing directly that CRAC channels open only in extreme proximity to these sites.

In cells co-expressing both STIM1 and Orai1, store depletion causes Orai1 itself to move from a dispersed distribution to accumulate in the plasma membrane directly opposite STIM1, enabling STIM1 to activate the channel (Luik, et al., *J. Cell Biol.* 174, 815-825 (2006); Xu, P. et al. *Biochem. Biophys. Res. Commun.* 350, 969-976 (2006)). Thus, CRAC channels are formed by apposed clusters of STIM1 in the ER and Orai1 in the plasma membrane, separated by a narrow gap of cytosol. The junctional gap between the ER and plasma membrane where Orai1/STIM1 clusters form (about 10-25 nm) may be small enough to permit protein-protein interactions between STIM1 and Orai1. This is supported by the fact that overexpressed STIM1 and Orai1 can be co-immunoprecipitated (Yeromin, A. V. et al. *Nature* 443, 226-229 (2006); Vig, M. et al. *Curr. Biol.* 16, 2073-2079 (2006)).

Thus, STIM1 and Orai1 interact either directly or as members of a multiprotein complex. Support for this was observed when the expression of the cytosolic portion of STIM1 by itself was sufficient to activate CRAC channels in one study, and the effects of deleting the ERM/coiled-coil and other C-terminal domains suggest roles in STIM1 clustering and SOC channel activation. On the luminal side of STIM1, the isolated EF-SAM region forms dimers and higher-order multimers on removal of $Ca^{2+}$ in vitro, indicating that STIM1 oligomerization may be an early step in store operated calcium activation.

Compounds of Formula (I) described herein modulate intracellular calcium, such as, inhibition or reduction of SOCE and/or $I_{CRAC}$. In some embodiments, the modulation by compounds of Formula (I) result from a variety of effects, such as, but not limited to, binding to a protein, interaction with a protein, or modulation of interactions, activities, levels or any physical, structural or other property of a protein involved in modulating intracellular calcium (e.g. a STIM protein and/or Orai protein).

For example, methods for assessing binding or interaction of a test agent with a protein involved in modulating intracellular calcium include NMR, mass spectroscopy, fluorescence spectroscopy, scintillation proximity assays, surface plasmon resonance assays and others. Examples of methods for assessing modulation of interactions, activities, levels or any physical, structural or other property of a protein involved in modulating intracellular calcium include, but are not limited to, FRET assays to assess effects on protein interactions, NMR, X-ray crystallography and circular dichroism to assess effects on protein interactions and on physical and structural properties of a protein, and activity assays suitable for assessing a particular activity of a protein.

Monitoring or Assessing Effects on Intracellular Calcium

In some embodiments, monitoring or assessing the effect of a compound of Formula (I) on intracellular calcium in any of the screening/identification methods described herein, a direct or indirect evaluation or measurement of cellular (including cytosolic and intracellular organelle or compartment) calcium and/or movement of ions into, within or out of a cell, organelle, calcium store or portions thereof (e.g., a membrane) are conducted. A variety of methods are described herein for evaluating calcium levels and ion movements or flux. The particular method used and the conditions employed depend on whether a particular aspect of intracellular calcium is being monitored or assessed. For example, in some embodiments described herein, reagents and conditions are known, and are used, for specifically evaluating store-operated calcium entry, resting cytosolic calcium levels, calcium buffering and calcium levels and uptake by or release from intracellular organelles and calcium stores. In other embodiments, the effect of a compound of Formula (I) on intracellular calcium is monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Methods of Modulating Intracellular Calcium

In some embodiments, modulation of intracellular calcium is any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In some embodiments, intracellular calcium modulation involves alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium involves an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE), in an immune system cell (e.g., a lymphocyte, white blood cell, T cell, B cell), a fibroblast (or a cell derived from a fibroblast), or an epidermal, dermal or skin cell (e.g., a keratinocyte). In some embodiments, the step of modulating one or more proteins involved in modulating intracellular calcium (e.g. a STIM protein and/or Orai protein) involves, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then in other embodiments, modulating involves reducing the level of, expression of, an activity or function of, or a molecular interaction of a protein, e.g. a STIM protein and/or Orai protein.

Treatment Methods

Presented herein is a method of modulating store-operated calcium (SOC) channel activity comprising contacting the store-operated calcium (SOC) channel complex, or portion thereof, with a compound of Formula (I) or pharmaceutically acceptable salt, pharmaceutically acceptable solvate, or pharmaceutically acceptable prodrug thereof.

In one embodiment is a method of modulating store-operated calcium channel activity comprising contacting the store-operated calcium (SOC) channel complex, or portion thereof, with a compound of Formula (I) wherein the contacting occurs in vitro.

In another embodiment is a method of modulating store-operated calcium channel activity comprising contacting the store-operated calcium (SOC) channel complex, or portion thereof, with a compound of Formula (I) wherein the contacting occurs in vivo.

In yet another embodiment is a method of modulating store-operated calcium channel activity comprising contacting the store-operated calcium (SOC) channel complex, or portion thereof, with a compound of Formula (I) wherein the compound of Formula (I) modulates an activity of, modulates an interaction of, or modulates the level of, or distributions of, or binds to, or interacts with at least one portion of the store operated calcium channel complex selected from stromal interaction molecules (STIM) family of proteins.

In a further embodiment is a method of modulating store-operated calcium channel activity comprising contacting the store-operated calcium (SOC) channel complex, or portion thereof, with a compound of Formula (I) wherein the compound of Formula (I) modulates an activity of, modulates an interaction of, or modulates the level of, or distributions of, or binds to, or interacts with at least one portion of STIM1 or STIM2.

In another embodiment is a method of modulating store-operated calcium channel activity comprising contacting the store-operated calcium (SOC) channel complex, or portion thereof, with a compound of Formula (I) wherein modulating store operated calcium channel activity with a compound of Formula (I) inhibits store-operated calcium entry (SOCE).

In yet another embodiment is a method of modulating store-operated calcium channel activity comprising contacting the store-operated calcium (SOC) channel complex, or portion thereof, with a compound of Formula (I) wherein the store operated calcium channel complex is calcium-release activated calcium (CRAC) channel complex.

In a further embodiment is a method of modulating store-operated calcium channel activity comprising contacting the store-operated calcium (SOC) channel complex, or portion thereof, with a compound of Formula (I) wherein modulating calcium release activated calcium (CRAC) activity with a compound of Formula (I) inhibits the electrophysiological current ($I_{CRAC}$) directly associated with activated CRAC channels.

Also presented herein is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof.

In one embodiment is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof wherein the compound of Formula (I) modulates an activity of, modulates an interaction of, or modulates the level of, or distributions of, or binds to, or interacts with at least one component of the calcium release activated (CRAC) channel complex selected from stromal interaction molecules (STIM) family of proteins.

In another embodiment is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof wherein the compound of Formula (I) modulates an activity of, modulates an interaction of, or modulates the level of, or distributions of, or binds to, or interacts with STIM1 or STIM2.

In yet another embodiment is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof wherein modulating calcium release activated calcium (CRAC) channel activity with a compound of Formula (I) inhibits store-operated calcium entry (SOCE).

In a further embodiment is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof wherein modulating calcium release activated calcium (CRAC) channel activity with a compound of Formula (I) inhibits the electrophysiological current ($I_{CRAC}$) directly associated with activated CRAC channels.

In yet a further embodiment is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof wherein the compound of Formula (I) inhibits SOCE with an $IC_{50}$ below 10 µM.

In another embodiment is a method of modulating calcium release activated calcium channel (CRAC) activity in a mammal comprising administering a compound of Formula (I) or pharmaceutically acceptable salt, pharmaceutically acceptable solvate, or pharmaceutically acceptable prodrug thereof wherein the compound of Formula (I) inhibits electrophysiological current ($I_{CRAC}$) directly associated with activated CRAC channels at a concentration below 10 µM.

In one aspect is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof.

In one embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the compound of v modulates the activity of, modulates an interaction of, or binds to, or interacts with a mammalian STIM1 protein, or a mammalian STIM2 protein.

In another embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the disease, disorder or condition in a mammal is selected from diseases/disorders involving inflammation, glomerulonephritis, uveitis, hepatic diseases or disorders, renal diseases or disorders, chronic obstructive pulmonary disease, rheumatoid arthritis, psoriasis, inflammatory bowel disease, vasculitis, dermatitis, osteoarthritis, inflammatory muscle disease, allergic rhinitis, vaginitis, interstitial cystitis, scleroderma, osteoporosis, eczema, organ transplant rejection, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, multiple sclerosis, Sjogren's syndrome, and autoimmune diseases or disorders.

In yet another embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the disease, disorder or condition is rheumatoid arthritis.

In a further embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the disease, disorder or condition is psoriasis.

In one embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the disease, disorder or condition is inflammatory bowel disease.

In a further embodiment the inflammatory bowel disease is ulcerative colitis.

In a further embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the disease, disorder or condition is organ transplant rejection.

In a further embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof wherein the disease, disorder or condition is multiple sclerosis.

In yet a further embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof further comprising administering to the mammal a second therapeutic agent.

In another embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof, wherein the second therapeutic agent is selected from immunosuppressants, glucocorticoids, non-steroidal anti-inflammatory drugs, Cox-2-specific inhibitors, leflunomide, gold thioglucose, gold thiomalate, aurofin, sulfasalazine, hydroxychloroquinine, minocycline, anti-TNF-α agents, abatacept, anakinra, interferon-β, interferon-γ, interleukin-2, allergy vaccines, antihistamines, antileukotrienes, beta-agonists, theophylline, and anticholinergics.

In yet another embodiment is a method of treating a disease, disorder or condition in a mammal that would benefit from inhibition of store operated calcium channel activity comprising administering to the mammal a compound of Formula (I) or pharmaceutically acceptable salt, pharmaceutically acceptable solvate, or pharmaceutically acceptable prodrug thereof, wherein the second therapeutic agent is selected from tacrolimus, cyclosporin, rapamicin, methotrexate, cyclophosphamide, azathioprine, mercaptopurine, mycophenolate, or FTY720, prednisone, cortisone acetate, prednisolone, methylprednisolone, dexamethasone, betamethasone, triamcinolone, beclometasone, fludrocortisone acetate, deoxycorticosterone acetate, aldosterone, aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502, JTE-522, L-745,337 and NS398, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, allergy vaccines, antihistamines, antileukotrienes, beta-agonists, theophylline, and anticholinergics.

Also described herein is a method of inhibiting store-operated calcium entry (SOCE) activation of nuclear factor of activated T cells (NFAT) in a mammal comprising administering a compound of Formula (I) or pharmaceutically acceptable salt, pharmaceutically acceptable solvate, or pharmaceutically acceptable prodrug thereof.

In one embodiment is a method of inhibiting store-operated calcium entry (SOCE) activation of nuclear factor of activated T cells (NFAT) in a mammal comprising administering a compound of Formula (I) or pharmaceutically acceptable salt, pharmaceutically acceptable solvate, or pharmaceutically acceptable prodrug thereof, wherein the compound of Formula (I) modulates an interaction of, or modulates the level of, or distributions of, or binds to, or interacts with a mammalian STIM1 protein, or a mammalian STIM2 protein.

In another aspect is a method of decreasing cytokine expression by inhibiting the store-operated calcium entry activation of NFAT in a mammal comprising administering a compound of Formula (I) or pharmaceutically acceptable salt, pharmaceutically acceptable solvate, or pharmaceutically acceptable prodrug thereof.

In another embodiment is a method of decreasing cytokine expression by inhibiting the store-operated calcium entry activation of NFAT in a mammal comprising administering a compound of Formula (I) or pharmaceutically acceptable salt, pharmaceutically acceptable solvate, or pharmaceutically acceptable prodrug thereof wherein the compound of Formula (I) modulates an interaction of, or modulates the level of, or distributions of, or binds to, or interacts with a mammalian STIM1 protein or a mammalian STIM2 protein.

In yet another embodiment is a method of decreasing cytokine expression by inhibiting the store-operated calcium entry activation of NFAT in a mammal comprising administering a compound of Formula (I) or pharmaceutically acceptable salt, pharmaceutically acceptable solvate, or pharmaceutically acceptable prodrug thereof wherein the cytokine is selected from IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, IL-1 RA, granulocyte colony stimulating factor (G-CSF), granulocyte-macrophage colony stimulating factor (GM-CSF), oncostatin M, erythropoietin, leukemia inhibitory factor (LIF), interferons, gamma-interferon (γ-IFN), B7.1 (CD80), B7.2 (B70, CD86), TNF-α, TNF-β, LT-β, CD40 ligand, Fas ligand, CD27 ligand, CD30 ligand, 4-1BBL, Trail, and migration inhibitory factor (MIF).

Compounds

Compounds described herein modulate intracellular calcium and are used in the treatment of diseases, disorders or conditions where modulation of intracellular calcium has a beneficial effect. In one embodiment, compounds described herein inhibit store operated calcium entry. In one embodiment, compounds of Formula (I) interrupt the assembly of SOCE units. In another embodiment, compounds of Formula (I) alter the functional interactions of proteins that form store operated calcium channel complexes. In one embodiment, compounds of Formula (I) alter the functional interactions of STIM1 with Orai1. In other embodiments, compounds of Formula (I) are SOC channel pore blockers. In other embodiments, compounds of Formula (I) are CRAC channel pore blockers.

In one aspect, compounds of Formula (I) inhibit the electrophysiological current ($I_{SOC}$) directly associated with activated SOC channels. In one aspect, compounds of Formula (I) inhibit the electrophysiological current ($I_{CRAC}$) directly associated with activated CRAC channels.

In other embodiments, the diseases, conditions or disorders that benefit from modulation of intracellular calcium include, but are not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, and disorders of the immune system), cancer or other proliferative disease, kidney disease and liver disease. In one embodiment, compounds described herein are used as immunosuppresants to prevent transplant graft rejections, allogeneic or xenogeneic transplantation rejection (organ, bone marrow, stem cells, other cells and tissues), graft-versus-host disease. In other embodiments, transplant graft rejections result from tissue or organ transplants. In further embodiments, graft-versus-host disease results from bone marrow or stem cell transplantation.

Compounds described herein modulate an activity of, modulate an interaction of, or binds to, or interacts with at least one portion of a protein in the store operated calcium channel complex. In one embodiment, compounds described herein modulate an activity of, modulate an interaction of, or binds to, or interacts with at least one portion of a protein in the calcium release activated calcium channel complex. In one embodiment, compounds described herein reduce the level of functional store operated calcium channel complexes. In one embodiment, compounds described herein reduce the level of activated store operated calcium channel complexes. In one embodiment, store operated calcium channel complexes are calcium release activated calcium channel complexes.

Compounds described herein for treatment of a disease or disorder, when administered to a subject having a disease or disorder effectively reduces, ameliorates or eliminates a symptom or manifestation of the disease, condition or disorder. In other embodiments, compounds described herein also are administered to a subject predisposed to a disease, condition or disorder that does not yet manifest a symptom of the disease, condition or disorder, prevents or delays development of the symptoms. In further embodiments, the agent has such effects alone or in combination with other agents, or functions to enhance a therapeutic effect of another agent.

In some embodiments, the compounds described herein, pharmaceutically acceptable salts, pharmaceutically acceptable prodrugs, or pharmaceutically acceptable solvates thereof, modulate intracellular calcium, and are used to treat patients where modulation of intracellular calcium provides benefit.

In one aspect, described herein is a compound of Formula (I), or pharmaceutically acceptable salt, pharmaceutically acceptable solvate, or pharmaceutically acceptable prodrug thereof:

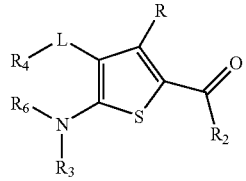

Formula (I)

wherein:
L is a bond, $C_1$-$C_6$alkyl, $C_1$-$C_6$alkenyl, $C_1$-$C_6$heteroalkyl, aryl, or heteroaryl; wherein $C_1$-$C_6$alkyl, $C_1$-$C_6$alkenyl, $C_1$-$C_6$heteroalkyl, aryl, or heteroaryl is optionally substituted with at least one $R_5$;
R is hydrogen, $CO_2R_1$, a carboxylic acid bioisostere, an optionally substituted heteroaryl, or an optionally substituted heterocycloalkyl;
$R_1$ is hydrogen, $C_1$-$C_6$alkyl, $C_1$-$C_6$cycloalkyl, $C_1$-$C_6$haloalkyl, phenyl or benzyl;
$R_2$ is cycloalkyl, aryl, arylalkyl, heteroaryl, heteroarylalkyl, heteroarylalkenyl, wherein cycloalkyl, aryl, arylalkyl, heteroaryl, heteroarylalkyl, heteroarylalkenyl is optionally substituted with at least one $R_5$;
$R_3$ and $R_6$ are each independently hydrogen $C_1$-$C_6$alkyl, —C(O)—$C_1$-$C_6$alkyl, —C(O)NR$_1$—$C_1$-$C_6$alkyl, wherein $C_1$-$C_6$alkyl is optionally substituted with at least one $R_5$; or
$R_3$ and $R_6$ together with the nitrogen atom to which they are attached form a $C_2$-$C_8$heterocycloalkyl group optionally substituted with at least one $R_5$;
$R_4$ is aryl or heteroaryl; wherein aryl or heteroaryl is optionally substituted with at least one $R_5$;
each $R_5$ is independently selected from F, Cl, Br, I, —CN, alkyne, $C_1$-$C_6$ alkylalkyne, —$NO_2$, —OH, —$CF_3$, —$OCF_3$, —$OR_8$, $C_1$-$C_6$alkyl, $C_3$-$C_8$cycloalkyl, $C_1$-$C_6$heteroalkyl, $C_1$-$C_6$haloalkyl, tetrazolyl, $C_2$-$C_8$heterocycloalkyl, optionally substituted aryl, optionally substituted heteroaryl, —NHS(=O)$_2$$R_8$, —S(=O)$_2$N($R_9$)$_2$, —N($R_9$)S(=O)$_2$N($R_9$)$_2$, —C(=O)$CF_3$, —C(=O)NHS(=O)$_2$$R_8$, —S(=O)$_2$NHC(=O)$R_8$, —N($R_9$)$_2$, —N($R_9$)C(=O)$R_8$, —N($R_9$)C(=O)N($R_9$)$_2$, —N($R_9$)C(=O)O$R_8$, —CO$_2$$R_9$, —C(=O)$R_8$, —OC(=O)$R_8$, —OC(=O)N($R_9$)$_2$, —CON($R_9$)$_2$, —S$R_8$, —S(=O)$R_8$, and —S(=O)$_2$$R_8$;

each $R_8$ is independently selected from $C_1$-$C_6$alkyl, $C_1$-$C_6$haloalkyl, $C_3$-$C_8$cycloalkyl, phenyl, and benzyl; and each $R_9$ is independently selected from H, $C_1$-$C_6$alkyl, $C_1$-$C_6$haloalkyl, $C_3$-$C_8$cycloalkyl, phenyl, and benzyl.

In one embodiment is a compound of Formula (I) wherein L is a bond. In another embodiment, L is phenyl. In a further embodiment, L is —$CH_2CH_2$—. In yet another embodiment L is —$CH_2$—.

In one embodiment is a compound of Formula (I) wherein R is hydrogen.

In another embodiment is a compound of Formula (I) wherein R is $CO_2R_1$. In one embodiment is a compound of Formula (I) wherein $R_1$ is hydrogen. In another embodiment, $R_1$ is $C_1$-$C_6$alkyl. In a further embodiment, $R_1$ is $CH_3$. In yet a further embodiment, $R_1$ is $CH_2CH_3$. In a further embodiment, R is a carboxylic acid bioisostere.

In yet another embodiment is a compound of Formula (I) wherein $R_1$ is hydrogen.

In a further embodiment is a compound of Formula (I) wherein $R_3$ is hydrogen.

In yet a further embodiment is a compound of Formula (I) wherein $R_3$ is $C_1$-$C_6$alkyl.

In one embodiment is a compound of Formula (I) wherein $R_3$ is $CH_3$.

In another embodiment is a compound of Formula (I) wherein $R_3$ is $CH_2CH_3$. In a further embodiment, $R_3$ is substituted with at least one halogen. In one embodiment, $R_3$ is —C(O)—$C_1$-$C_6$alkyl. In another embodiment, $R_3$ is —C(O)$CH_3$. In another embodiment, $R_3$ is —C(O)$CH_2CH_3$.

In yet another embodiment is a compound of Formula (I) wherein $R_6$ is hydrogen.

In a further embodiment is a compound of Formula (I) wherein $R_6$ is $C_1$-$C_6$alkyl.

In yet a further embodiment is a compound of Formula (I) wherein $R_6$ is $CH_3$.

In one embodiment is a compound of Formula (I) wherein $R_6$ is $CH_2CH_3$. In a further embodiment, $R_6$ is substituted with at least one halogen. In one embodiment, $R_6$ is —C(O)—$C_1$-$C_6$alkyl. In another embodiment, $R_6$ is —C(O)$CH_3$. In another embodiment, $R_6$ is —C(O)$CH_2CH_3$. In a further embodiment, $R_3$ is hydrogen and $R_6$ is —C(O)—$C_1$-$C_6$alkyl. In another embodiment, $R_3$ is hydrogen and $R_6$ is —C(O)$CH_3$.

In another embodiment is a compound of Formula (I) wherein $R_3$ and $R_6$ together with the nitrogen atom to which they are attached form a $C_2$-$C_8$heterocycloalkyl. In a further embodiment is a compound of Formula (I) wherein $R_3$ and $R_6$ together with the nitrogen atom to which they are attached form a $C_3$-$C_8$heterocycloalkyl wherein the $C_3$-$C_8$heterocycloalkyl contains at least one additional heteroatom selected from O, $NR_1$, and S.

In one embodiment is a compound of Formula (I) wherein $R_3$ and $R_6$ together with the nitrogen atom to which they are attached form a group selected from:

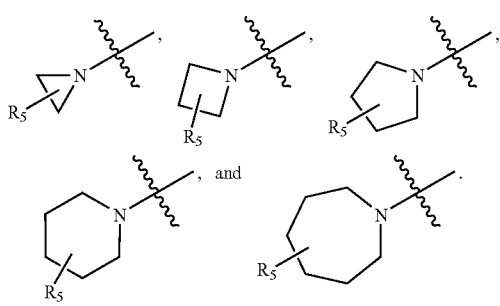

In another embodiment is a compound of Formula (I) wherein $R_3$ and $R_6$ together with the nitrogen atom to which they are attached form a group selected from:

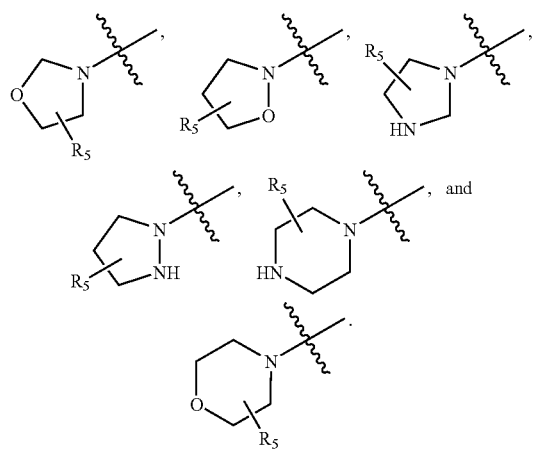

In yet another embodiment is a compound of Formula (I) wherein $R_2$ is aryl.

In a further embodiment is a compound of Formula (I) wherein aryl is a phenyl group.

In yet a further embodiment is a compound of Formula (I) wherein the phenyl group is substituted with at least one $R_5$ selected from F, Cl, Br, I, —CN, —NO$_2$, —OH, —CF$_3$, —OCF$_3$, —OR$_8$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, and optionally substituted heteroaryl.

In one embodiment is a compound of Formula (I) wherein $R_5$ is selected from F, Cl, Br, I, —CN, —NO$_2$, —OH, —CF$_3$, —OCF$_3$, —OR$_8$, C$_1$-C$_6$alkyl.

In another embodiment is a compound of Formula (I) wherein $R_5$ is Cl. In one embodiment is a compound of Formula (I) wherein $R_5$ is F. In another embodiment, $R_5$ is monosubstituted. In another embodiment, $R_5$ is di- or tri-substituted. In a further embodiment, $R_5$ is —OR$_8$ wherein $R_8$ is C$_1$-C$_6$alkyl. In another embodiment, $R_8$ is CH$_3$. In a further embodiment, $R_5$ is CN.

In yet another embodiment is a compound of Formula (I) wherein $R_4$ is aryl.

In a further embodiment is a compound of Formula (I) wherein aryl is a phenyl group.

In yet a further embodiment is a compound of Formula (I) wherein the phenyl group is substituted with at least one $R_5$ selected from F, Cl, Br, I, —CN, —NO$_2$, —OH, —CF$_3$, —OCF$_3$, —OR$_8$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, and optionally substituted heteroaryl.

In one embodiment is a compound of Formula (I) wherein $R_5$ is selected from F, Cl, Br, I, —CN, —NO$_2$, —OH, —CF$_3$, —OCF$_3$, —OR$_8$, and C$_1$-C$_6$alkyl.

In another embodiment is a compound of Formula (I) wherein $R_5$ is Br.

In yet another embodiment is a compound of Formula (I) wherein $R_5$ is Cl. In another embodiment, $R_5$ is monosubstituted. In another embodiment, $R_5$ is di- or tri-substituted. In another embodiment, $R_5$ is di-substituted with a halogen selected from F, Cl, Br, and I. In a further embodiment, $R_5$ is —OR$_8$ wherein $R_8$ is C$_1$-C$_6$alkyl. In another embodiment, $R_8$ is CH$_3$. In one embodiment, $R_8$ is phenyl. In a further embodiment, $R_5$ is CN.

In a further embodiment is a compound of Formula (I) wherein $R_2$ is heteroaryl.

In yet a further embodiment is a compound of Formula (I) wherein heteroaryl is selected from pyridine, pyrimidine, pyrazine, pyrazole, oxazole, thiazole, isoxazole, isothiazole, 1,3,4-oxadiazole, pyridazine, 1,3,5-trazine, 1,2,4-triazine, quinoxaline, benzimidazole, benzotriazole, purine, 1H-[1,2,3]triazolo[4,5-d]pyrimidine, triazole, imidazole, thiophene, benzothiophene furan, benzofuran, isobenzofuran, pyrrole, indolizine, isoindole, indole, indazole, isoquinoline, quinoline, phthalazine, naphthyridine, quinazoline, cinnoline, and pteridine.

In one embodiment is a compound of Formula (I) wherein heteroaryl is selected from pyridine, furan, and thiophene.

In another embodiment is a compound of Formula (I) wherein heteroaryl is substituted with at least one $R_5$ selected from F, Cl, Br, I, —CN, —NO$_2$, —OH, —CF$_3$, —OCF$_3$, —OR$_8$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, and optionally substituted heteroaryl.

In yet another embodiment is a compound of Formula (I) wherein $R_5$ is selected from F, Cl, Br, I, —CN, —NO$_2$, —OH, —CF$_3$, —OCF$_3$, —OR$_8$, and C$_1$-C$_6$alkyl. In one embodiment is a compound of Formula (I) wherein $R_5$ is Br. In one embodiment is a compound of Formula (I) wherein $R_5$ is Cl. In another embodiment, $R_5$ is monosubstituted. In another embodiment, $R_5$ is di- or tri-substituted. In another embodiment, $R_5$ is di-substituted with a halogen selected from F, Cl, Br, and I. In a further embodiment, $R_5$ is —OR$_8$ wherein $R_8$ is C$_1$-C$_6$alkyl. In another embodiment, $R_8$ is CH$_3$. In a further embodiment, $R_5$ is CN.

In one aspect is a compound selected from the group consisting of:

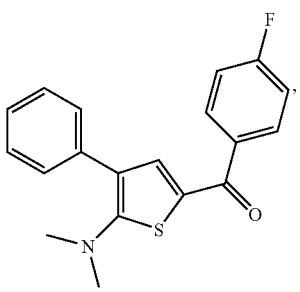

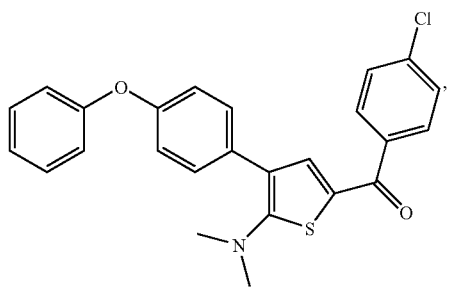
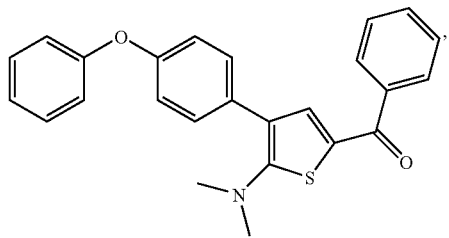
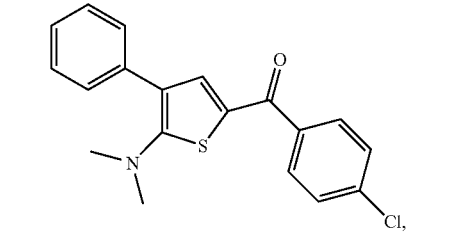
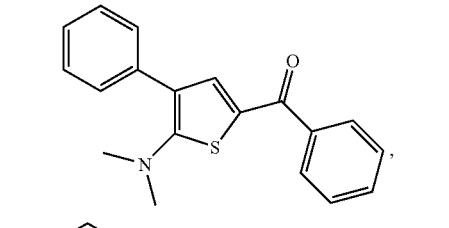
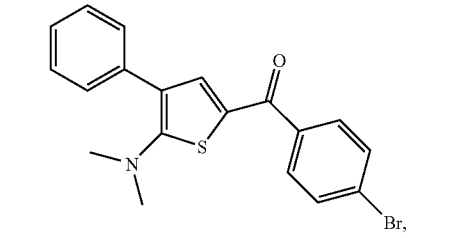
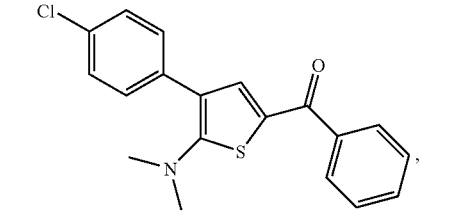
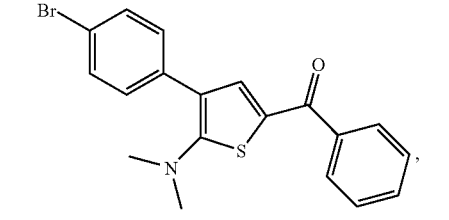
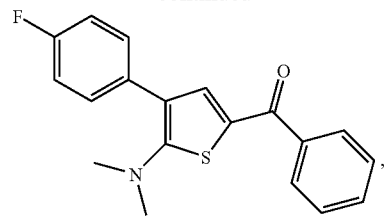
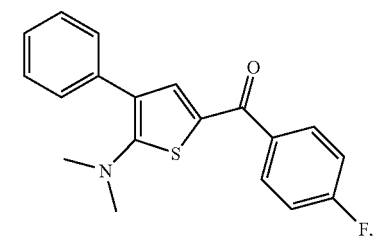
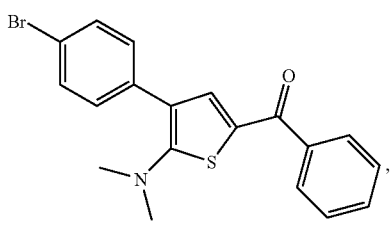
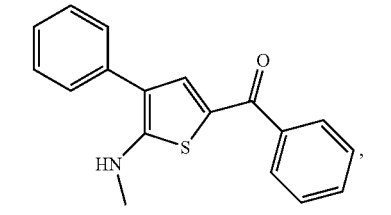
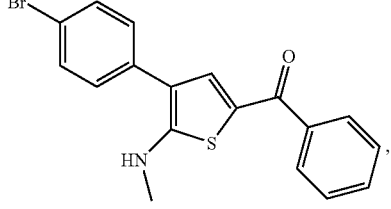
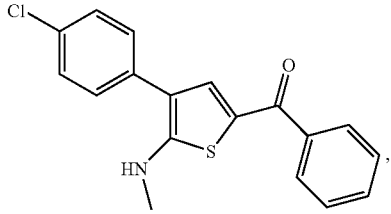
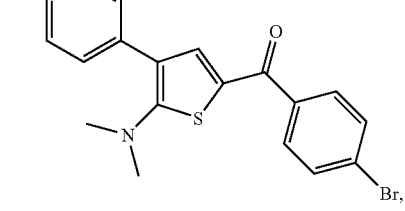

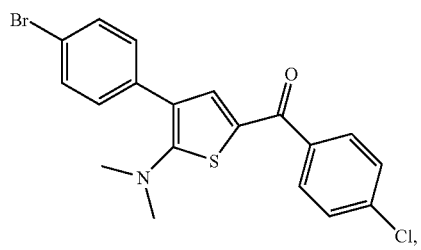
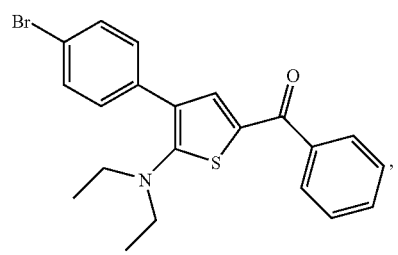
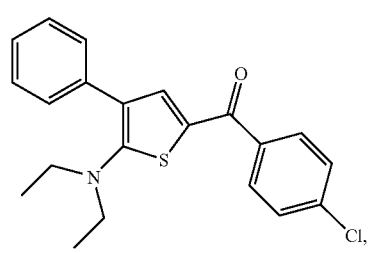
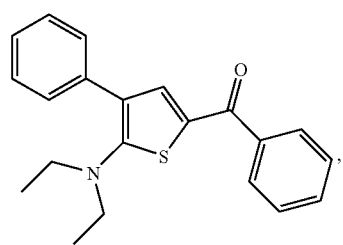
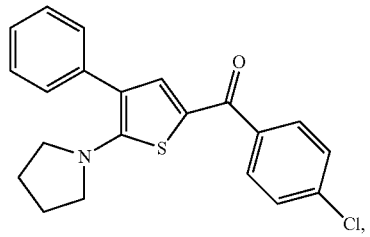
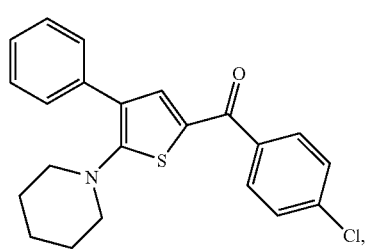
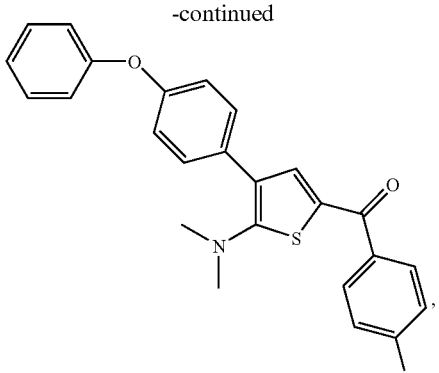
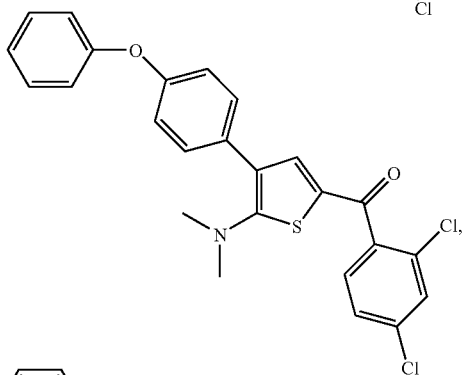
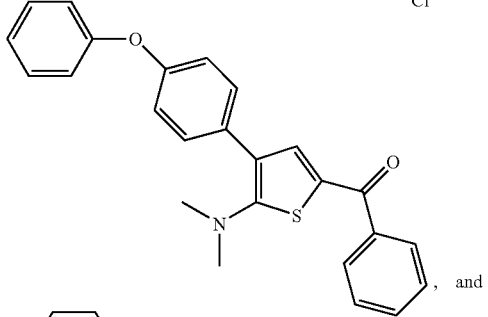
, and
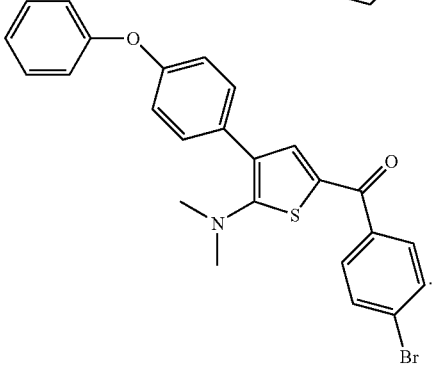
In one embodiment is a compound of Formula (I) having the structure selected from:
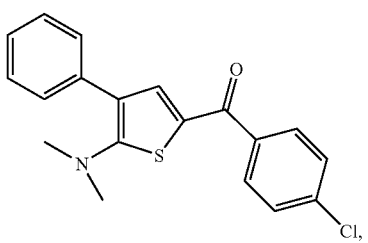

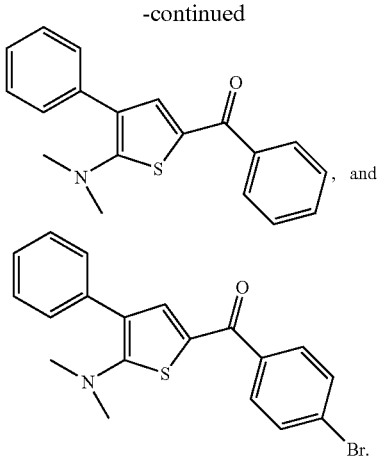

Further Forms of Compounds

In some embodiments, the compounds described herein exist as diastereomers, enantiomers, or other stereoisomerism forms. The compounds presented herein include all diastereomeric, enantiomeric, and epimeric forms as well as the appropriate mixtures thereof. Separation of stereoisomers are performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, the separation of stereoisomers as discussed in this reference is herein incorporated). In other embodiments, stereoisomers are obtained by stereoselective synthesis.

In some situations, compounds exist as tautomers. All tautomers are included within the formulas described herein.

The methods and compositions described herein include the use of amorphous forms as well as crystalline forms (also known as polymorphs). The compounds described herein are in the form of pharmaceutically acceptable salts. As well, active metabolites of these compounds having the same type of activity are included in the scope of the present disclosure. In addition, in other embodiments, the compounds described herein exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they are easier to administer than the parent drug. In some other embodiments, the prodrug is bioavailable by oral administration whereas the parent is not. In other embodiments, the prodrug also has improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. In other embodiments, the prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. In other embodiments, the prodrug is designed to alter the metabolic stability or the transport characteristics of a drug, to mask side effects or toxicity, to improve the flavor of a drug or to alter other characteristics or properties of a drug.

Prodrug forms of the herein described compounds, wherein the prodrug is metabolized in vivo to produce a compound of Formula (I) as set forth herein are included within the scope of the claims. In some cases, some of the herein-described compounds are a prodrug for another derivative or active compound.

In some embodiments are prodrugs that are designed as reversible drug derivatives, for use as modifiers to enhance drug transport to site-specific tissues. In some embodiments, the design of a prodrug increases the effective water solubility.

In some embodiments, sites on the aromatic ring portion of compounds described herein are susceptible to various metabolic reactions, therefore incorporation of appropriate substituents on the aromatic ring structures, such as, by way of example only, halogens can reduce, minimize or eliminate this metabolic pathway.

In other embodiments, the compounds described herein are labeled isotopically (e.g. with a radioisotope) or by other means, including, but not limited to, the use of chromophores or fluorescent moieties, bioluminescent labels, photoactivatable or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. In other embodiments are examples of isotopes that are incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, in some other embodiments, substitution with isotopes such as deuterium, i.e., $^{2}H$, affords certain therapeutic advantages resulting from greater metabolic stability, such as, for example, increased in vivo half-life or reduced dosage requirements.

In further embodiments, the compounds described herein are metabolized upon administration to an organism in need to produce a metabolite that is then used to produce a desired effect, including a desired therapeutic effect.

Compounds described herein are formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and in some embodiments are formed during the process of crystallization with pharmaceutically acceptable solvents such as water, ethanol, and the like. Hydrates are formed when the solvent is water, or alcoholates are formed when the solvent is alcohol. In some embodiments, solvates of compounds described herein are conveniently prepared or formed during the processes described herein. In other embodiments the compounds provided herein exist in unsolvated as well as solvated forms. In general, the solvated forms are considered equivalent to the unsolvated forms for the purposes of the compounds and methods provided herein.

In other embodiments, compounds described herein, such as compounds of Formula (I), are in various forms, including but not limited to, amorphous forms, milled forms and nanoparticulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

In further embodiments, the screening and characterization of the pharmaceutically acceptable salts, polymorphs and/or solvates are accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Synthesis of Compounds

In some embodiments, the synthesis of compounds described herein are accomplished using means described in the chemical literature, using the methods described herein, or by a combination thereof.

The starting materials and reagents used for the synthesis of the compounds described herein are synthesized or are obtained from commercial sources, such as, but not limited to, Sigma-Aldrich, FischerScientific (Fischer Chemicals), and AcrosOrganics.

The compounds described herein, and other related compounds having different substituents are synthesized using techniques and materials described herein as well as other techniques, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (the synthetic techniques described in the above publications are herein incorporated by reference). General methods for the preparation of compound as disclosed herein are derived from known reactions, and in some embodiments, the reactions are modified by the use of appropriate reagents and conditions, for the introduction of the various moieties found in the formulae as provided herein. As a guide the following synthetic methods are utilized.

Formation of Covalent Linkages by Reaction of an Electrophile with a Nucleophile In some embodiments, the compounds described herein are modified using various electrophiles and/or nucleophiles to form new functional groups or substituents. Table 2 entitled "Examples of Covalent Linkages and Precursors Thereof" lists selected non-limiting examples of covalent linkages and precursor functional groups which yield the covalent linkages. Table 2 is used as guidance toward the variety of electrophiles and nucleophiles combinations available that provide covalent linkages. Precursor functional groups are shown as electrophilic groups and nucleophilic groups.

TABLE 2

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |

TABLE 2-continued

Examples of Covalent Linkages and Precursors Thereof

| Covalent Linkage Product | Electrophile | Nucleophile |
|---|---|---|
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Alkyl amines | sulfonate esters | amines/anilines |
| Thioethers | sulfonate esters | Thiols |
| Sulfonamides | sulfonyl halides | amines/anilines |
| Sulfonate esters | sulfonyl halides | phenols/alcohols |

Use of Protecting Groups

In some embodiments, in the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments, each protective group is removable by a different means. Protective groups that are cleaved under totally disparate reaction conditions fulfill the requirement of differential removal.

In other embodiments, protective groups are removed by acid, base, reducing conditions (such as, for example, hydrogenolysis), and/or oxidative conditions. In other embodiments, groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. In further embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In yet further embodiments, carboxylic acid and hydroxy reactive moieties are blocked with hydrolytically removable protective groups such as the benzyl group, while amine groups capable of hydrogen bonding with acids are blocked with base labile groups such as Fmoc. In other embodiments, carboxylic acid reactive moieties are protected by conversion to simple ester compounds as exemplified herein, which include conversion to alkyl esters, or they are blocked with oxidatively-removable protective groups such as 2,4-dimethoxybenzyl, while co-existing amino groups are blocked with fluoride labile silyl carbamates.

In further embodiments, allyl blocking groups are useful in then presence of acid- and base-protecting groups since the former are stable and are subsequently removed by metal or pi-acid catalysts. For example, an allyl-blocked carboxylic acid is deprotected with a Pd⁰-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

Typically, in some embodiments, blocking/protecting groups are selected from:

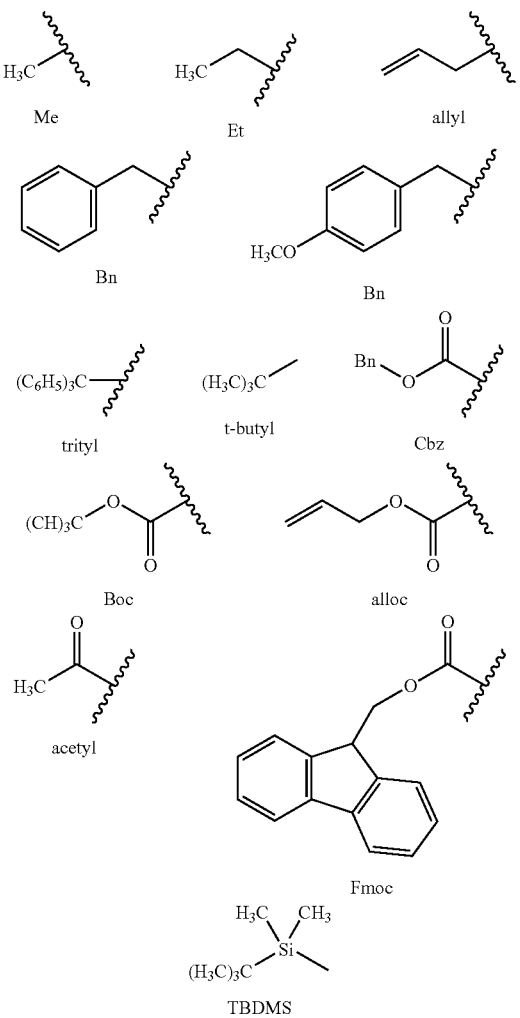

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, the discussion of protecting groups in the above publication is herein incorporated by reference for such disclosure.

Certain Terminology

Unless defined otherwise, all technical and scientific terms used herein have the same meaning as is commonly understood in the field to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information is found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms are found in reference works, including but not limited to, Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed.

Unless specific definitions are provided, the nomenclature employed in connection with, and the laboratory procedures and techniques of, analytical chemistry, synthetic organic chemistry, and medicinal and pharmaceutical chemistry described herein are those known in the art. In some embodiments, standard techniques are used for chemical syntheses, chemical analyses, pharmaceutical preparation, formulation, and delivery, and treatment of patients. In other embodiments, standard techniques are used for recombinant DNA, oligonucleotide synthesis, and tissue culture and transformation (e.g., electroporation, lipofection). In further embodiments, reactions and purification techniques are performed e.g., using kits of manufacturer's specifications or as commonly accomplished in the art or as described herein. The foregoing techniques and procedures are generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_X$ includes $C_1$-$C_2$, $C_1$-$C_3$ ... $C_1$-$C_X$. $C_1$-$C_X$ refers to the number of carbon atoms that make up the moiety to which it designates (excluding optional substituents).

An "alkyl" group refers to an aliphatic hydrocarbon group. In some embodiments, the alkyl groups include or do not include units of unsaturation. In some embodiments, the alkyl moiety is a "saturated alkyl" group, which means that it does not contain any units of unsaturation (i.e. a carbon-carbon double bond or a carbon-carbon triple bond). In further embodiments, the alkyl group also is an "unsaturated alkyl" moiety, which means that it contains at least one unit of unsaturation. In some embodiments, the alkyl moiety, whether saturated or unsaturated, is branched, straight chain, or cyclic.

In other embodiments, the "alkyl" group has 1 to 6 carbon atoms (whenever it appears herein, a numerical range such as "1 to 6" refers to each integer in the given range; e.g., "1 to 6 carbon atoms" means that the alkyl group consists of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein are designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. In some embodiments, alkyl groups are substituted or unsubstituted. In other embodiments, depending on the structure, an alkyl group is a monoradical or a diradical (i.e., an alkylene group).

An "alkoxy" refers to a "O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)═CR$_2$, wherein R refers to the remaining portions of the alkenyl group, which are the same or different. Non-limiting examples of an alkenyl group include —CH═CH$_2$, —C(CH$_3$)═CH$_2$, —CH═CHCH$_3$, —CH═C(CH$_3$)$_2$ and —C(CH$_3$)═CHCH$_3$. The alkenyl moiety are branched, straight chain, or cyclic (in which case, it would also be known as a "cycloalkenyl" group). Alkenyl groups may have 2 to 6 carbons. Alkenyl groups are substituted or unsubstituted. In some other embodiments, depending on the structure, an alkenyl group is a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. In other embodiments, the "R" portion of the alkynyl moiety is branched, straight chain, or cyclic. An alkynyl group can have 2 to 6 carbons. Alkynyl groups are substituted or unsubstituted. In some embodiments, depending on the structure, an alkynyl group is a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. In some embodiments, when x=2, the alkyl groups, taken together with the nitrogen to which they are attached, optionally form a cyclic ring system. "Dialkylamino" refers to a —N(alkyl)$_2$ group, where alkyl is as defined herein.

The term "aromatic" refers to a planar ring having a delocalized π-electron system containing 4n+2π electrons, where n is an integer. In other embodiments, aromatic rings are formed from five, six, seven, eight, nine, or more than nine atoms. In some other embodiments, aromatics are optionally substituted. The term "aromatic" includes both aryl groups (e.g., phenyl, napthalenyl) and heteroaryl groups (e.g., pyridinyl, quinolinyl).

As used herein, the term "aryl" refers to an aromatic ring wherein each of the atoms forming the ring is a carbon atom. In further embodiments, aryl rings are formed by five, six, seven, eight, nine, or more than nine carbon atoms. In some embodiments, aryl groups are optionally substituted. Examples of aryl groups include, but are not limited to phenyl, and naphthalenyl. In other embodiments, depending on the structure, an aryl group is a monoradical or a diradical (i.e., an arylene group).

The term "arylalkyl" as used herein, means an aryl group, as defined herein, appended to the parent molecular moiety through an alkyl group, as defined herein. Representative examples of arylalkyl include, but are not limited to benzyl, 2-phenylethyl, -phenylpropyl, 1-methyl-3-phenylpropyl, and 2-naphth-2-ylethyl.

"Carboxy" refers to —$CO_2H$. In some cases, carboxy moieties are replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisoteres of a carboxylic acid include, but are not limited to,

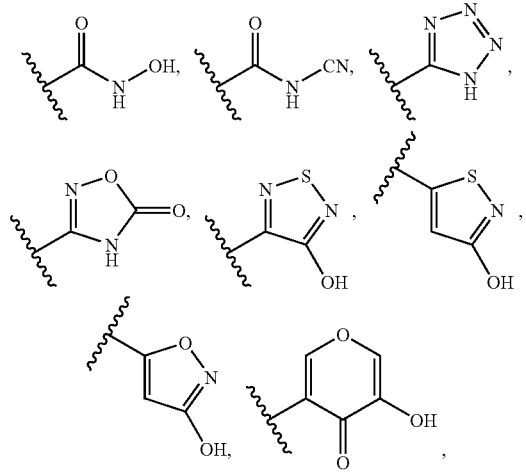

and the like.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated, or partially unsaturated. In other embodiments, cycloalkyls are fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

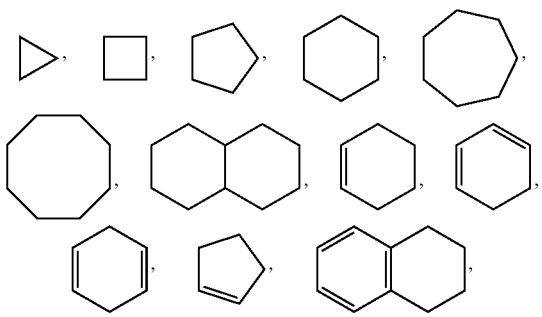

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In some embodiments, polycyclic heteroaryl groups are fused or non-fused. Illustrative examples of heteroaryl groups include the following moieties:

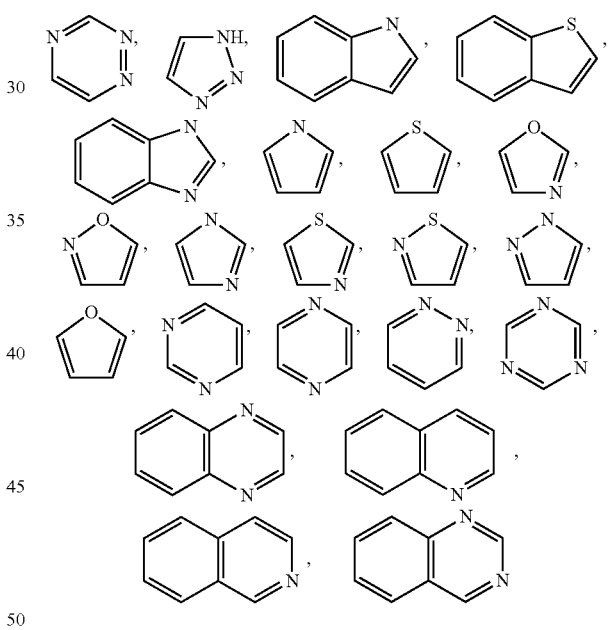

and the like.

The term "heteroarylalkyl" as used herein, means a heteroaryl, as defined herein, appended to the parent molecular moiety through an alkyl group, as defined herein. Representative examples of heteroarylalkyl include, but are not limited to, pyridinylmethyl.

The term "heteroarylalkenyl" as used herein, means a heterocycle, as defined herein, appended to the parent molecular moiety through an alkenyl group, as defined herein.

A "heterocycloalkyl" group or "heteroalicyclic" group refers to a cycloalkyl group, wherein at least one skeletal ring atom is a heteroatom selected from nitrogen, oxygen and sulfur. In some embodiments, the radicals are fused with an aryl or heteroaryl. Illustrative examples of heterocycloalkyl groups, also referred to as non-aromatic heterocycles, include:

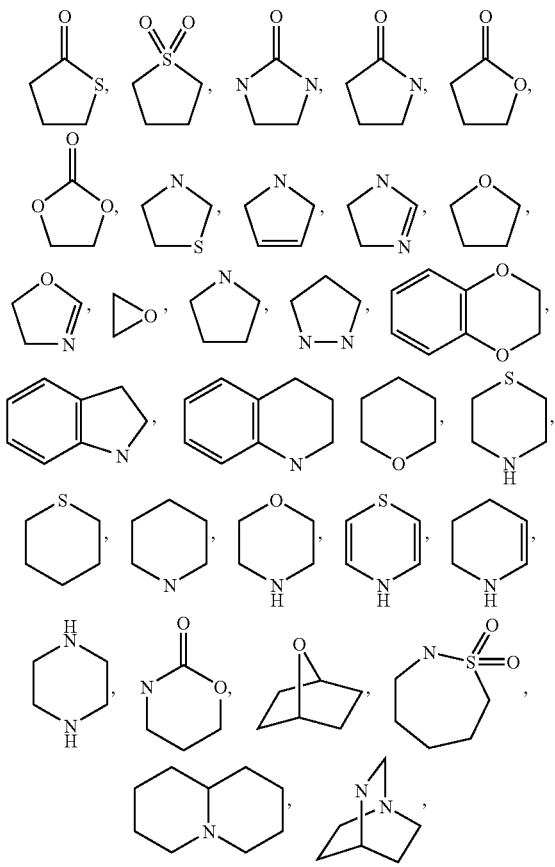

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e skeletal atoms of the heterocycloalkyl ring).

The term "heterocycloalkylalkyl" as used herein, means a heterocycle, as defined herein, appended to the parent molecular moiety through an alkyl group, as defined herein.

The term "halo" or, alternatively, "halogen" means fluoro, chloro, bromo and iodo.

The term "haloalkyl" refers to an alkyl group that is substituted with one or more halogens. In some embodiments, the halogens are the same or they are different. Non-limiting examples of haloalkyls include —$CH_2Cl$, —$CF_3$, —$CHF_2$, —$CH_2CF_3$, —$CF_2CF_3$, —$CF(CH_3)_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. In some embodiments, the heteroatom(s) are placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In some embodiments up to two heteroatoms are consecutive, such as, by way of example, —$CH_2$—NH—$OCH_3$ and —$CH_2$—O—Si ($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents is $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. In some embodiments, the protecting groups that form the protective derivatives of the above substituents are found in sources such as Greene and Wuts, above.

The methods and formulations described herein include the use of crystalline forms (also known as polymorphs), or pharmaceutically acceptable salts of compounds having the structure of Formula (I), as well as active metabolites of these compounds having the same type of activity. In some situations, compounds exist as tautomers. All tautomers are included within the scope of the compounds presented herein. In some embodiments the compounds described herein exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

As used herein, the term "target protein" refers to a protein or a portion of a protein capable of being bound by, or interacting with a compound described herein, such as a compound of Formula (I). In certain embodiments, a target protein is a STIM protein. In certain embodiments, a target protein is an Orai protein.

As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

As used herein, an "Orai protein" includes Orai1 (SEQ ID NO: 1 as described in WO 07/081,804), Orai2 (SEQ ID NO: 2 as described in WO 07/081,804), or Orai3 (SEQ ID NO: 3 as described in WO 07/081,804). Orai1 nucleic acid sequence corresponds to GenBank accession number NM_032790, Orai2 nucleic acid sequence corresponds to GenBank accession number BC069270 and Orai3 nucleic acid sequence corresponds to GenBank accession number NM_152288. As used herein, Orai refers to any one of the Orai genes, e.g., Orai1, Orai2, Orai3 (see Table I of WO 07/081,804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

The term "fragment" or "derivative" when referring to a protein (e.g. STIM, Orai) means proteins or polypeptides which retain essentially the same biological function or activity in at least one assay as the native protein(s). For example, the fragments or derivatives of the referenced protein maintains at least about 50% of the activity of the native proteins, at least about 75%, at least about 95% of the activity of the native proteins, as determined e.g. by a calcium influx assay.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that are attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, in some embodiments, a modulator causes an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, and alteration of the kinetics of calcium fluxes into, out of and within cells. In aspect, modulation refers to reduction.

The terms "inhibits", "inhibiting", or "inhibitor" of SOC channel activity or CRAC channel activity, as used herein, refer to inhibition of store operated calcium channel activity or calcium release activated calcium channel activity.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g. a compound of Formula (I), and a co-agent, are both administered to a patient simultaneously in the form of a single entity or dosage. The term "non-fixed combination" means that one active ingredient, e.g. a compound of Formula (I), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of Formula (I) described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of the composition that includes a compound of Formula (I) described herein required to provide a clinically significant decrease in disease symptoms. In some embodiments, an appropriate "effective" amount in any individual case is determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. In some embodiments, diluents are used to stabilize compounds because they provide a more stable environment. Salts dissolved in buffered solutions (which also provide pH control or maintenance) are utilized as diluents, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, in some embodiments, enzymes produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism are obtained from The Pharmacological Basis of Therapeutics, 9th Edition, McGraw-Hill (1996). Metabolites of the compounds disclosed herein are identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein (e.g. compound of Formula (I)), that is delivered into the general circulation of the animal or human being studied. The total exposure (AUC(0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound of Formula (I) disclosed herein, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein varies from subject to subject. Likewise, in some embodiments, values such as maximum plasma concentration ($C_{max}$) or time to reach maximum plasma concentration ($T_{max}$), or total area under the plasma concentration time curve (AUC(0-∞)) varies from subject to subject. Due to this variability, the amount necessary to constitute "a therapeutically effective amount" of a compound will vary from subject to subject.

As used herein, "calcium homeostasis" refers to the maintenance of an overall balance in intracellular calcium levels and movements, including calcium signaling, within a cell.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, in some embodiments, an effect on intracellular calcium is an alteration of the properties, such as, for example, the kinetics, sensitivities, rate, amplitude, and electrophysiological characteristics, of calcium flux or movement that occurs in a cell or portion thereof. In some embodiments, an effect on intracellular calcium is an alteration in any intracellular calcium-modulating process, including, store-operated calcium entry, cytosolic calcium buffering, and calcium levels in or movement of calcium into, out of or within an intracellular calcium store. Any of these aspects are assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration is any such change that is statistically significant. Thus, for example, in some embodiments, if intracellular calcium in a test cell and a control cell is said to differ, such differences are a statistically significant difference.

As used herein, "involved in" with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity can occur by virtue of an alteration of expression of a gene encoding the protein or by altering the levels of the protein. A protein involved in an aspect of intracellular calcium, such as, for example, store-operated calcium entry, thus, are one that provides for or participates in an aspect of intracellular calcium or intracellular calcium regulation. For example, a protein that provides for store-operated calcium entry are a STIM protein and/or an Orai protein.

As used herein, a protein that is a component of a calcium channel is a protein that participates in multi-protein complex that forms the channel.

As used herein, "cation entry" or "calcium entry" into a cell refers to entry of cations, such as calcium, into an intracellular location, such as the cytoplasm of a cell or into the lumen of an intracellular organelle or storage site. Thus, in some embodiments, cation entry is, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "protein that modulates intracellular calcium" refers to any cellular protein that is involved in regulating, controlling and/or altering intracellular calcium. For example, in some embodiments, such a protein is involved in altering or adjusting intracellular calcium in a number of ways, including, but not limited to, through the maintenance of resting or basal cytoplasmic calcium levels, or through involvement in a cellular response to a signal that is transmitted in a cell through a mechanism that includes a deviation in intracellular calcium from resting or basal states. In the context of a "protein that modulates intracellular calcium," a "cellular" protein is one that is associated with a cell, such as, for example, a cytoplasmic protein, a plasma membrane-associated protein or an intracellular membrane protein. Proteins that modulate intracellular calcium include, but are not limited to, ion transport proteins, calcium-binding proteins and regulatory proteins that regulate ion transport proteins.

As used herein, "amelioration" refers to an improvement in a disease or condition or at least a partial relief of symptoms associated with a disease or condition.

As used herein, "cell response" refers to any cellular response that results from ion movement into or out of a cell or within a cell. In some embodiments, the cell response is associated with any cellular activity that is dependent, at least in part, on ions such as, for example, calcium. Such activities include, for example, cellular activation, gene expression, endocytosis, exocytosis, cellular trafficking and apoptotic cell death.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" refers to small soluble proteins secreted by cells that in some embodiments, alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1$\alpha$, IL-1$\beta$, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-$\alpha$, TNF-$\beta$, LT-$\beta$, CD40 ligand, Fas ligand, CD27 ligand, CD30 ligand, 4-1BBL, Trail), and MIF.

"Store operated calcium entry" or "SOCE" refers to the mechanism by which release of calcium ions from intracellular stores is coordinated with ion influx across the plasma membrane.

"Selective inhibitor of SOC channel activity" means that the inhibitor is selective for SOC channels and does not substantially affect the activity of other types of ion channels.

"Selective inhibitor of CRAC channel activity" means that the inhibitor is selective for CRAC channels and does not substantially affect the activity of other types of ion channels and/or other SOC channels.

Examples of Pharmaceutical Compositions and Methods of Administration

Pharmaceutical compositions are formulated in a conventional manner using one or more physiologically acceptable carriers including excipients and auxiliaries which facilitate processing of the active compounds into preparations which are used pharmaceutically. Proper formulation is dependent upon the route of administration chosen. In some embodiments, any of the well-known techniques, carriers, and excipients are used as suitable. In some embodiments, a summary of pharmaceutical compositions described herein are found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), the pharmaceutical compositions described in the above publications are herein incorporated by reference for such disclosure.

A pharmaceutical composition, as used herein, refers to a mixture of a compound of Formula (I) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. In some embodiments, a therapeutically effective amount varies widely depending on the severity of the disease, the age and relative health of the subject, the potency of the compound used and other factors. In some embodiments, the compounds of Formula (I) are used singly or in combination with one or more therapeutic agents as components of mixtures (as in combination therapy).

In further embodiments, the pharmaceutical formulations described herein are administered to a subject by multiple administration routes, including but not limited to, oral, parenteral (e.g., intravenous, subcutaneous, intramuscular), intranasal, buccal, topical, rectal, or transdermal administration routes. Moreover, in some embodiments, the pharmaceutical compositions described herein, which include a compound of Formula (I) described herein, are formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, the compounds and/or compositions are administered in a local rather than systemic manner, for example, via injection of the compound directly into an organ or tissue, often in a depot preparation or sustained release formulation. In other embodiments, such long acting formulations are administered by implantation (for example subcutaneously or intramuscularly) or by intramuscular injection. Furthermore, in some embodiments, the drug is administered in a targeted drug delivery system, for example, in a liposome coated with organ-specific antibody. The liposomes will be targeted to and taken up selectively by the organ. In some embodiments, the drug is provided in the form of a rapid release formulation, in the form of an extended release formulation, or in the form of an intermediate release formulation.

In some embodiments, pharmaceutical compositions including a compound described herein is manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I) described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity.

In certain embodiments, compositions provided herein also include one or more preservatives to inhibit microbial activity. Suitable preservatives include quaternary ammonium compounds such as benzalkonium chloride, cetyltrimethylammonium bromide and cetylpyridinium chloride.

In some embodiments, pharmaceutical preparations for oral use are obtained by mixing one or more solid excipient with one or more of the compounds described herein (e.g. compounds of Formula (I)), optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In other embodiments disintegrating agents are added, such as the cross-linked croscarmellose sodium, polyvinylpyrrolidone, agar, or alginic acid or a salt thereof such as sodium alginate.

Dragee cores are provided with suitable coatings. For this purpose, in some embodiments, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs or pigments are added to the tablets or dragee coatings for identification or to characterize different combinations of active compound doses.

In further embodiments, pharmaceutical preparations that are used orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In some embodiments, are soft capsules, wherein the active compounds are dissolved or suspended in suitable liquids, such as fatty oils, liquid paraffin, or liquid polyethylene glycols. In some embodiments stabilizers are added.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein are administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula (I) described herein, with one or more pharmaceutical excipients to form a bulk blend composition. When referring to these bulk blend compositions as homogeneous, it is meant that the particles of the compound of Formula (I) described herein, are dispersed evenly throughout the composition so that the composition are readily subdivided into equally effective unit dosage forms, such as tablets, pills, and capsules. In some embodiments, the individual unit dosages also include film coatings, which disintegrate upon oral ingestion or upon contact with diluent. In further embodiments, these formulations are manufactured by conventional pharmacological techniques.

In some embodiments, the pharmaceutical solid dosage forms described herein include a compound of Formula (I) described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other embodiments, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (I) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and SolkaFloc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that in some embodiments, are filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum°, polyethylene glycol, waxes, sodium alginate, and the like.

In general, binder levels of about 20 to about 70% are used in powder-filled gelatin capsule formulations. In some embodiments, binder usage level in tablet formulations varies whether direct compression, wet granulation, roller compaction, or usage of other excipients such as fillers which itself act as moderate binder. In some embodiments, are tablet formulations comprising binder usage levels of up to about 70%.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., in some embodiments, the polyethylene glycol has a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that are included in solid dosage forms of the pharmaceutical compositions described herein.

In other embodiments, one or more layers of the pharmaceutical formulation are plasticized. Illustratively, a plasticizer is generally a high boiling point solid or liquid. In some embodiments, suitable plasticizers are added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating provides a delayed release of the compounds of Formula (I) described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

In some embodiments, a capsule is prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (I) described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another formulation, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients. Materials compatible with compounds of Formula (I) described herein are those that delay the release of the compounds of Formula (I) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocer®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of Formula (I) described herein are formulated by methods which in some embodiments, include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, in some other embodiments, several chemical techniques, e.g., complex coacervation, solvent evaporation, polymer-polymer incompatibility, interfacial polymerization in liquid media, in situ polymerization, in-liquid drying, and desolvation in liquid media are used. Furthermore, in other embodiments, other methods such as roller compaction, extrusion/spheronization, coacervation, or nanoparticle coating also are used.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide are used in place of the combination of sodium bicarbonate and citric and tartaric acids, as long as the ingredients were suitable for pharmaceutical use and result in a pH of about 6.0 or higher.

In other embodiments, the formulations described herein, which include a compound described herein, are solid dispersions. In still other embodiments, the formulations described herein are solid solutions. Solid solutions incorporate a substance together with the active agent and other excipients such that heating the mixture results in dissolution of the drug and the resulting composition is then cooled to provide a solid blend which is further formulated or directly added to a capsule or compressed into a tablet.

The pharmaceutical solid oral dosage forms including formulations described herein, which include a compound of Formula (I) described herein, are further formulated to provide a controlled release of the compound of Formula (I). Controlled release refers to the release of the compound of Formula (I) described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. In some embodiments, such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine of the gastrointestinal tract. In further embodiments, the enteric coated dosage form is a compressed or molded or extruded tablet/mold (coated or uncoated) containing granules, powder, pellets, beads or particles of the active ingredient and/or other composition components, which are themselves coated or uncoated. In other embodiments, the enteric coated oral dosage form is also a capsule (coated or uncoated) containing pellets, beads or granules of the solid carrier or the composition, which are themselves coated or uncoated.

The term "delayed release" as used herein refers to the delivery so that the release is accomplished at some generally predictable location in the intestinal tract more distal to that which would have been accomplished if there had been no delayed release alterations. In some embodiments the method for delay of release is a coating. Any coatings should be applied to a sufficient thickness such that the entire coating does not dissolve in the gastrointestinal fluids at pH below about 5, but does dissolve at pH about 5 and above. In some embodiments, coatings are made from:

Acrylic polymers. In some embodiments, the performance of acrylic polymers (primarily their solubility in biological fluids) vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. In other embodiments, the performance varies based on the degree and type of substitution. Cellulose acetate phthalate (CAP) dissolves in pH>about 6. Aquateric (FMC) is an aqueous based system and is a spray dried CAP psuedolatex with particles <1 μm. In other embodiments, other components in Aquateric include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). In further embodiments, the performance varies based on the degree and type of substitution. For example, HPMCP such as, HP-50, HP-55, HP-55S, HP-55F grades are suitable. In other embodiments, the performance varies based on the degree and type of substitution. For example, suitable grades of hydroxypropylmethylcellulose acetate succinate include, but are not limited to, AS-LG (LF), which dissolves at pH about 5, AS-MG (MF), which dissolves at pH about 5.5, and AS-HG (HF), which dissolves at higher pH. These polymers are offered as granules, or as fine powders for aqueous dispersions.

Poly Vinyl Acetate Phthalate (PVAP). PVAP dissolves in pH>about 5, and it is much less permeable to water vapor and gastric fluids.

In some embodiments, the coating contains a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In some embodiments, anionic carboxylic acrylic polymers contain about 10 to about 25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

In some embodiments, colorants, detackifiers, surfactants, antifoaming agents, lubricants (e.g., carnuba wax or PEG) are added to the coatings besides plasticizers to solubilize or disperse the coating material, and to improve coating performance and the coated product.

In other embodiments, the formulations described herein, which include a compound of Formula (I) described herein, are delivered using a pulsatile dosage form. A pulsatile dosage form is capable of providing one or more immediate release pulses at predetermined time points after a controlled lag time or at specific sites. In further embodiments, pulsatile dosage forms are administered using a variety of pulsatile formulations.

Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like.

In some embodiments, pharmaceutical formulations are provided that include particles of the compounds described herein, e.g. compounds of Formula (I), and at least one dispersing agent or suspending agent for oral administration to a subject. In some embodiments, the formulations are a powder and/or granules for suspension, and upon admixture with water, a substantially uniform suspension is obtained.

In some embodiments, liquid formulation dosage forms for oral administration are aqueous suspensions selected from the group including, but not limited to, pharmaceutically acceptable aqueous oral dispersions, emulsions, solutions, elixirs, gels, and syrups.

In other embodiments, the aqueous suspensions and dispersions described herein remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension is re-suspended into a homogenous suspension by physical agitation lasting less than about 1 minute. In another embodiment, an aqueous suspension is re-suspended into a homogenous suspension by physical agitation lasting less than about 45 seconds. In yet another embodiment, an aqueous suspension is re-suspended into a homogenous suspension by physical agitation lasting less than about 30 seconds. In still another embodiment, no agitation is necessary to maintain a homogeneous aqueous dispersion.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, in other embodiments, water or the aqueous phase is added just prior to administration, which ensures stability of an unstable or hydrophobic active ingredient. Thus, the SEDDS provides an effective delivery system for oral and parenteral delivery of hydrophobic active ingredients. In further embodiments, SEDDS provides improvements in the bio-availability of hydrophobic active ingredients.

It is to be appreciated that there is overlap between the above-listed additives used in the aqueous dispersions or suspensions described herein, since a given additive is often classified differently by different practitioners in the field, or is commonly used for any of several different functions. Thus, in other embodiments, the above-listed additives are taken as merely exemplary, and not limiting, of the types of additives that are included in formulations described herein.

In some embodiments, formulations that include a compound described herein, are prepared according to these and other techniques are prepared as solutions in saline, employing benzyl alcohol or other suitable preservatives, fluorocarbons, and/or other solubilizing or dispersing agents. In other embodiments, are compositions and formulations prepared with suitable nontoxic pharmaceutically acceptable ingredients. In further embodiments, these ingredients are found in REMINGTON: THE SCIENCE AND PRACTICE OF PHARMACY, 21st edition, 2005. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. In other embodiments, the nasal dosage form is isotonic with nasal secretions.

In some embodiments, for administration by inhalation, the compounds described herein are in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In further embodiments, are pressurized aerosols, wherein the dosage unit is determined by providing a valve to deliver a metered amount. Capsules and cartridges of, such as, by way of example only, gelatin for use in an inhaler or insufflator are formulated containing a powder mix of the compound described herein and a suitable powder base such as lactose or starch.

In other embodiments, are buccal formulations that include compounds described herein are administered using a variety of formulations. In some embodiments, the buccal dosage forms described herein further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier is used, so long as the desired drug release profile is not compromised, and the carrier is compatible with the compound of Formula (I) described herein, and any other components that are present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which are obtained from B.F. Goodrich, is one such polymer). In further embodiments are components incorporated into the buccal dosage forms described herein include, but are not limited to, disintegrants, diluents, binders, lubricants, flavoring, colorants, preservatives, and the like. In yet further embodiments, are buccal or sublingual administration, wherein the compositions take the form of tablets, lozenges, or gels formulated in a conventional manner.

In further embodiments, are transdermal formulations described herein administered using a variety of devices.

In other embodiments the transdermal dosage forms described herein incorporate certain pharmaceutically acceptable excipients. In one embodiment, the transdermal formulations described herein include at least three components: (1) a formulation of a compound of Formula (1); (2) a penetration enhancer; and (3) an aqueous adjuvant. In addition, transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintains a saturated or supersaturated state to promote diffusion into the skin.

In other embodiments, formulations suitable for transdermal administration of compounds described herein employ transdermal delivery devices and transdermal delivery patches and are lipophilic emulsions or buffered, aqueous solutions, dissolved and/or dispersed in a polymer or an adhesive. Such patches are constructed for continuous, pulsatile, or on demand delivery of pharmaceutical agents. Still further, in some embodiments, transdermal delivery of the compounds described herein are accomplished by means of iontophoretic patches and the like. Additionally, in other embodiments, transdermal patches provide controlled delivery of the compound of Formula (I) described herein.

In further embodiments, the rate of absorption is slowed by using rate-controlling membranes or by trapping the compound within a polymer matrix or gel. Conversely, in yet further embodiments, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In further embodiments, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. In some embodiments, proper fluidity is maintained, for example, by the use of a coating such as lecithin, by the maintenance of the required particle size in the case of dispersions, and by the use of surfactants. In further embodiments, formulations suitable for subcutaneous injection also contain additives such as preserving, wetting, emulsifying, and dispensing agents. Prevention of the growth of microorganisms is ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form are brought about by the use of agents delaying absorption, such as aluminum monostearate and gelatin.

In some embodiments, are intravenous injections, compounds formulated in aqueous solutions; in some embodiments, in physiologically compatible buffers such as Hank's solution, Ringer's solution, or physiological saline buffer. For transmucosal administration, penetrants appropriate to the barrier to be permeated are used in the formulation For other parenteral injections, appropriate formulations optionally include aqueous or nonaqueous solutions; in other embodiments, with physiologically compatible buffers or excipients.

In some embodiments, parenteral injections involve bolus injection or continuous infusion. In other embodiments, formulations for injection are presented in unit dosage form, e.g., in ampoules or in multi-dose containers, with an added preservative. In some embodiments, the pharmaceutical compositions described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of the active compounds in water-soluble form. Additionally, in other embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In further embodiments, aqueous injection suspensions contain substances which increase the viscosity of the suspension, such as sodium carboxymethyl cellulose, sorbitol, or dextran. In some embodiments, the suspension also contains suitable stabilizers or agents which increase the solubility of the compounds to allow for the preparation of highly concentrated solutions. In other embodiments, the active ingredient is in powder form for constitution with a suitable vehicle, e.g., sterile pyrogen-free water, before use.

In certain embodiments, delivery systems for pharmaceutical compounds are employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein are administered topically and are formulated into a variety of topically administrable compositions, such as solutions, suspensions, lotions, gels, pastes, medicated sticks, balms, creams or ointments. Such pharmaceutical compounds contain for example, solubilizers, stabilizers, tonicity enhancing agents, buffers and preservatives.

In some embodiments, the compounds described herein are also formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound of Formula (I), is administered in an amount effective for amelioration of, or prevention of the development of symptoms of, the disease, condition or disorder (i.e., a therapeutically effective amount). Thus, in some embodiments, a therapeutically effective amount is an amount that is capable of at least partially preventing or reversing a disease, condition or disorder. In other embodiments, the dose required to obtain an effective amount varies depending on the agent, formulation, disease, condition or disorder, and individual to whom the agent is administered.

In other embodiments, determination of effective amounts also involves in vitro assays in which varying doses of agent are administered to cells in culture and the concentration of agent effective for ameliorating some or all symptoms is determined in order to calculate the concentration required in vivo. Effective amounts are also based on in vivo animal studies.

In other embodiments, an agent is administered prior to, concurrently with and subsequent to the appearance of symptoms of a disease, condition or disorder. In some embodiments, an agent is administered to a subject with a family history of the disease, condition or disorder, or who has a phenotype that indicates a predisposition to a disease, condition or disorder, or who has a genotype which predisposes the subject to the disease, condition or disorder.

In some embodiments, the particular delivery system used depends on a number of factors, including, for example, the intended target and the route of administration, e.g., local or systemic. Targets for delivery are specific cells which are causing or contributing to a disease, condition or disorder, including, for example, cells that have altered intracellular calcium or calcium dysregulation or dyshomeostasis, and cells that do not have altered intracellular calcium but that in some embodiments, have some alteration, defect or deficiency that is, at least in part, compensated, counteracted, reversed or alleviated or eliminated by altering intracellular calcium of the cell. Particular cells include, for example, immune cells (e.g., lymphocytes, T cells, B cells, white blood cells), fibroblasts (or cells derived from a fibroblast), epidermal, dermal or skin cells (e.g., a keratinocytes), blood cells, kidney or renal cells (e.g., mesangial cells), muscle cells (e.g., a smooth muscle cell such as an airway (tracheal or bronchial) smooth muscle cell) and exocrine or secretory (e.g., salivary, including parotid acinar and submandibular gland) cells. For example, in some embodiments, a target cell is a resident or infiltrating cells in the lungs or airways that contribute to an asthmatic illness or disease, resident or infiltrating cells in the nervous system contributing to a neurological, neurodegenerative or demyelinating disease, condition or disorder, resident or infiltrating cells involved in rejection of a kidney graft, grafted cells that when activated lead to graft-versus-host disease, resident or infiltrating cells involved in rejection of a kidney graft, resident or infiltrating cells, activation of which contributes to inflammation, e.g., in arthritis, resident or infiltrating cells in the kidney or renal system (e.g., mesangial cells) involved in neuropathy and glomerulonephritis and resident or infiltrating cells in exocrine glands (e.g., salivary and lacrimal glands) involved in autoimmune disorders (e.g., Sjogren's disease). In some embodiments, an agent is coupled to an antibody, ligand to a cell surface receptor or a toxin, or is contained in a particle that is selectively internalized into cells, e.g., liposomes or a virus in which the viral receptor binds specifically to a certain cell type, or a viral particle lacking the viral nucleic acid, or are administered locally.

Examples of Methods of Dosing and Treatment Regimens

In some embodiments, the compounds described herein are used in the preparation of medicaments for the modulation of intracellular calcium, or for the treatment of diseases, disorders or conditions that would benefit, at least in part, from modulation of intracellular calcium. In addition, a method for treating any of the diseases, disorders or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

In other embodiments, the compositions containing the compound(s) described herein are administered for prophylactic and/or therapeutic treatments. In therapeutic applications, the compositions are administered to a patient already suffering from a disease, disorder or condition, in an amount sufficient to cure or at least partially arrest the symptoms of the disease, disorder or condition. Amounts effective for this use will depend on the severity and course of the disease, disorder or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some embodiments wherein the patient's condition does not improve, upon the doctor's discretion the administration of the compounds is administered chronically, that is, for an extended period of time, including throughout the duration of the patient's life in order to ameliorate or otherwise control or limit the symptoms of the patient's disease or condition.

In other embodiments, wherein the patient's status does improve, upon the doctor's discretion the administration of the compounds are given continuously; alternatively, the dose of drug being administered is temporarily reduced or temporarily suspended for a certain length of time (i.e., a "drug holiday"). In other embodiments, the length of the drug holiday varies between about 2 days and about 1 year, including by way of example only, about 2 days, about 3 days, about 4 days, about 5 days, about 6 days, about 7 days, about 10 days, about 12 days, about 15 days, about 20 days, about 28 days, about 35 days, about 50 days, about 70 days, about 100 days, about 120 days, about 150 days, about 180 days, about 200 days, about 250 days, about 280 days, about 300 days, about 320 days, about 350 days, or about 365 days. In some embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, in other embodiments, the dosage or the frequency of administration, or both, is reduced, as a function of the symptoms, to a level at which the improved disease, disorder or condition is retained. In other embodiments, patients, however, require intermittent treatment on a long-term basis upon any recurrence of symptoms.

In other embodiments, the amount of a given agent varies depending upon factors such as the particular compound, disease, disorder or condition and its severity, the identity (e.g., weight) of the subject or host in need of treatment, but is nevertheless determined in a manner according to the particular circumstances surrounding the case, including, e.g., the specific agent being administered, the route of administration, the condition being treated, and the subject or host being treated. In some embodiments, doses employed for adult human treatment are typically in the range of about 0.02 to about 5000 mg per day, in other embodiments, about 1 to about 1500 mg per day. In further embodiments, the desired dose is conveniently presented in a single dose or as divided doses administered simultaneously (or over a short period of time) or at appropriate intervals, for example as two, three, four or more sub-doses per day.

In other embodiments, the pharmaceutical composition described herein is in unit dosage forms suitable for single administration of precise dosages. In unit dosage form, the formulation is divided into unit doses containing appropriate quantities of one or more compound. In further embodiments, the unit dosage is in the form of a package containing discrete quantities of the formulation. Non-limiting examples are packaged tablets or capsules, and powders in vials or ampoules. In other embodiments, aqueous suspension compositions are packaged in single-dose non-reclosable containers. In further embodiments, multiple-dose reclosable containers are used, in which case it is typical to include a preservative in the composition. By way of example only, formulations for parenteral injection are presented in unit dosage form, which include, but are not limited to ampoules, or in multi-dose containers, with an added preservative.

The daily dosages appropriate for the compounds described herein described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. In some embodiments, such dosages are altered depending on a number of variables, not limited to the activity of the compound used, the disease, disorder or condition to be treated, the mode of administration, the requirements of the individual subject, the severity of the disease, disorder or condition being treated, and the judgment of the practitioner.

In further embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it are expressed as the ratio between $LD_{50}$ and $ED_{50}$. In other embodiments, are compounds exhibiting high therapeutic indices. In other embodiments, the data obtained from cell culture assays and animal studies are used in formulating a range of dosage for use in human. In some other embodiments, the dosage of such compounds lies within a range of circulating concentrations that include the $ED_{50}$ with minimal toxicity. In further embodiments, the dosage varies within this range depending upon the dosage form employed and the route of administration utilized.

Combination Treatments

In other embodiments, the compounds of Formula (I), and compositions thereof, are also used in combination with other therapeutic agents that are selected for their therapeutic value for the condition to be treated. In general, the compositions described herein and, in embodiments where combinational therapy is employed, other agents do not have to be administered in the same pharmaceutical composition, and in some embodiments, because of different physical and chemical characteristics, have to be administered by different routes.

In certain instances, it is appropriate to administer at least one compound of Formula (I) described herein in combination with another therapeutic agent. By way of example only, if one of the side effects experienced by a patient upon receiving one of the compounds herein, such as a compound of Formula (I), is nausea, then it is appropriate to administer an anti-nausea agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering one of the compounds described herein with another therapeutic agent (which also includes a therapeutic regimen) that also has therapeutic benefit. In any case, in other embodiments, regardless of the disease, disorder or condition being treated, the overall benefit experienced by the patient is simply be additive of the two therapeutic agents or the patient experiences a synergistic benefit.

In other embodiments, the particular choice of compounds used depends upon the diagnosis of the attending physicians and their judgment of the condition of the patient and the appropriate treatment protocol. In further embodiments, the compounds are administered concurrently (e.g., simultaneously, essentially simultaneously or within the same treatment protocol) or sequentially, depending upon the nature of the disease, disorder, or condition, the condition of the patient, and the actual choice of compounds used.

In some embodiments, therapeutically-effective dosages vary when the drugs are used in treatment combinations. Combination treatment further includes periodic treatments that start and stop at various times to assist with the clinical management of the patient.

In some embodiments, combination therapies described herein, dosages of the co-administered compounds vary depending on the type of co-drug employed, on the specific drug employed, on the disease, disorder or condition being treated and so forth. In addition, when co-administered with one or more biologically active agents, the compound provided herein is administered either simultaneously with the biologically active agent(s), or sequentially. In some embodiments, if administered sequentially, the attending physician decides on the appropriate sequence of administering protein in combination with the biologically active agent(s).

In some embodiments, the multiple therapeutic agents (one of which is a compound of Formula (I) described herein) are administered in any order or even simultaneously. In other embodiments, if simultaneously, the multiple therapeutic agents are provided in a single, unified form, or in multiple forms (by way of example only, either as a single pill or as two separate pills). In other embodiments, one of the therapeutic agents are given in multiple doses, or both are given as multiple doses. If not simultaneous, the timing between the multiple doses vary from more than zero weeks to less than about four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, is modified in accordance with a variety of factors. These factors include the disorder, disease or condition from which the subject suffers, as well as the age, weight, sex, diet, and medical condition of the subject. Thus, in other embodiments, the dosage regimen actually employed varies widely and therefore can deviate from the dosage regimens set forth herein.

In other embodiments, the pharmaceutical agents who make up the combination therapy disclosed herein are in a combined dosage form or in separate dosage forms intended for substantially simultaneous administration. In other embodiments, the pharmaceutical agents that make up the combination therapy are also administered sequentially, with either therapeutic compound being administered by a regimen calling for two-step administration. In yet other embodiments, the two-step administration regimen calls for sequential administration of the active agents or spaced-apart administration of the separate active agents. In further embodiments, the time period between the multiple administration steps range from, a few minutes to several hours, depending upon the properties of each pharmaceutical agent, such as potency, solubility, bioavailability, plasma half-life and kinetic profile of the pharmaceutical agent. In other embodiments, circadian variation of the target molecule concentration also determines the optimal dose interval.

In addition, the compounds described herein also are used in combination with procedures that in some embodiments, provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In further embodiments, the compounds described herein and combination therapies are administered before, during or after the occurrence of a disease, disorder or condition, and the timing of administering the composition containing a compound varies. Thus, for example, the compounds are used as a prophylactic and are administered continuously to subjects with a propensity to develop conditions, disorders or diseases in order to prevent the occurrence of the disease, disorder or condition. In other embodiments, the compounds and compositions are administered to a subject during or as soon as possible after the onset of the symptoms. In other embodiments, the administration of the compounds are initiated within the first 48 hours of the onset of the symptoms, in some embodiments, within the first 48 hours of the onset of the symptoms, in yet other embodiments within the first 6 hours of the onset of the symptoms, and in other embodiments within 3 hours of the onset of the symptoms. In further embodiments, the initial administration is via any route practical, such as, for example, an intravenous injection, a bolus injection, infusion over about 5 minutes to about 5 hours, a pill, a capsule, transdermal patch, buccal delivery, and the like, or combination thereof. In other embodiments, a compound is administered as soon as is practicable after the onset of a disease, disorder or condition is detected or suspected, and for a length of time necessary for the treatment of the disease, such as, for example, from about 1 day to about 3 months. In other embodiments, the length of treatment varies for each subject, and the length is determined using the known criteria. For example, the compound or a formulation containing the compound is administered for at least 2 weeks, in some embodiments about 1 month to about 5 years.

Inhibitors of SOCE

In one aspect, compounds of Formula (I) are administered or used in conjunction with other inhibitors of SOCE. In one embodiment, the inhibitors of SOCE are non-selective inhibitors. In one embodiment, the inhibitors of SOCE are selective inhibitors.

A variety of inhibitors of SOCE have been described. Inhibitors of SOCE include:
a) Cations, which include lanthanide cations, such as for example, $Gd^{3+}$, $La^{3+}$;
b) P-450 inhibitors, which include econazole, miconazole, clotrimazole, ketoconazole;
c) Cyclooxygenase inhibitors, which include niflumic acid, flufenamic acid, tenidap;
d) Lipoxygenase inhibitors, which include nordihydroguaiaretic acid, eicosatetraynoic acid;
e) Compounds that are channel blockers, which include SK&F 96365, SC38249, LU52396, L-651,582, tetrandrine, 2-APB;
f) Compounds that inhibit SOCE not by an action on the SOC channels themselves, which include U73122 (phospholipase C inhibitor), wortmannin (phosphatidylinositol kinase inhibitor).

Some of these inhibitors of SOCE have non-specific actions and/or multiple modes of action that contribute to the inhibition of SOCE, which include blocking the pore of the SOC channel (Channel blockers), inhibition of mitochondrial ATP synthesis that appears to support SOCE, disturbances of cytoplasmic pH (, as well as inhibiting the activation of SOC channels.

Immunosuppresants

In one embodiment, compounds of Formula (I) are administered as single agents in immunosuppressive therapy to reduce, inhibit, or prevent activity of the immune system. Immunosuppressive therapy is clinically used to: prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control).

In some embodiments, a compound of Formula (I) is administered with other immunosuppresants selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG))).

Other immunosuppresants include, but are not limited to: glucocorticoids (alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, Fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, ulobetasol), cyclophosphamide, nitrosoureas, cisplatin, carboplatin, oxaliplatin, methotrexate, azathioprine, mercaptopurine, pyrimidine analogues, protein synthesis inhibitors, methotrexate, azathioprine, mercaptopurine, dactinomycin, anthracyclines, mitomycin C, bleomycin, mithramycin, Atgam®, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), mycophenolic acid, mycophenolate mofetil, FTY720, as well as those listed in U.S. Pat. No. 7,060,697.

Agents for Treating Autoimmune Diseases, Inflammatory Diseases

In some embodiments, where the subject is suffering from or at risk of suffering from an autoimmune disease, disorder or condition, or an inflammatory disease, disorder or condition, a compound of Formula (I) is administered in any combination with one or more of the following therapeutic agents: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, etoricoxib, lumiracoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, antileukotrienes, theophylline, or anticholinergics.

In one embodiment, compounds of Formula (I) described herein, are administered in combination with inhibitors of NFAT-calcineurin pathway. In one embodiment, the inhibitors of NFAT-calcineurin pathway include, but are not limited to, Cyclosporin A (CsA) and tacrolimus (FK506).

In one embodiment, a compound of Formula (I), or compositions and medicaments that include a compound of Formula (I), are administered to a patient in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketolorac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Combinations with NSAIDs, which are selective COX-2 inhibitors, are contemplated herein. Such compounds include, but are not limited to those disclosed in U.S. Pat. No. 5,474,995; U.S. Pat. No. 5,861,419; U.S. Pat. No. 6,001,843; U.S. Pat. No. 6,020,343, U.S. Pat. No. 5,409,944; U.S. Pat. No. 5,436,265; U.S. Pat. No. 5,536,752; U.S. Pat. No. 5,550,142; U.S. Pat. No. 5,604,260; U.S. Pat. No. 5,698,584; U.S. Pat. No. 5,710,140; WO 94/15932; U.S. Pat. No. 5,344,991; U.S. Pat. No. 5,134,142; U.S. Pat. No. 5,380,738; U.S. Pat. No. 5,393,790; U.S. Pat. No. 5,466,823; U.S. Pat. No. 5,633,272; U.S. Pat. Nos. 5,932,598 and 6,313,138; the disclosure of NSAIDs which are herein incorporated by reference.

Compounds that have been described as selective COX-2 inhibitors and are therefore useful in the methods or pharmaceutical compositions described herein include, but are not limited to, celecoxib, rofecoxib, lumiracoxib, etoricoxib, valdecoxib, and parecoxib, or a pharmaceutically acceptable salt thereof.

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Other agents used as anti-imflammatories include those disclosed in U.S. patent publication 2005/0227929, the disclosure of anti-inflammatories which is herein incorporated by reference.

Some commercially available anti-inflammatories include, but are not limited to: Arthrotec® (diclofenac and misoprostol), Asacol® (5-aminosalicyclic acid), Salofalk® (5-aminosalicyclic acid), Auralgan® (antipyrine and benzocaine), Azulfidine® (sulfasalazine), Daypro® (oxaprozin), Lodine® (etodolac), Ponstan® (mefenamic acid), Solumedrol® (methylprednisolone), Bayer® (aspirin), Bufferin® (aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaren® (diclofenac), Orudis® (ketoprofen), Mobic® (meloxicam), Relafen® (nabumetone), Aleve®, Naprosyn® (naproxen), Feldene® (piroxicam).

In one embodiment, compounds of Formula (I) are administered in combination with leukotriene receptor antagonists including, but are not limited to, BAY u9773 (see EP 00791576; published 27 Aug. 1997), DUO-LT (Tsuji et al, *Org. Biomol. Chem.,* 1, 3139-3141, 2003), zafirlukast (Accolate®), montelukast (Singulair®), prankulast (Onon®), and derivatives or analogs thereof.

Kits/Articles of Manufacture

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of CRAC channel activity.

For example, in some embodiments, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

In some other embodiments, a kit includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. In other embodiments, a set of instructions is also included.

In further embodiments, is a label on or associated with the container. In other embodiments, the label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. In yet other embodiments, the label also indicates directions for use of the contents, such as in the methods described herein.

In certain embodiments, the pharmaceutical compositions are presented in a pack or dispenser device which contains one or more unit dosage forms containing a compound provided herein. In other embodiments, the pack contains metal or plastic foil, such as a blister pack. In other embodiments, the pack or dispenser device is accompanied by instructions for administration. In still other embodiments, the pack or dispenser also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. Compositions containing a compound provided herein formulated in a compatible pharmaceutical carrier are also prepared, placed in an appropriate container, and labeled for treatment of an indicated condition.

Assays

In some embodiments, several techniques are used to evaluate store operated calcium entry and calcium signaling in cells. Such techniques include, but are not limited to, patch clamp electrophysiology (measurement of calcium ions or other ions across cell membranes, such as plasma membranes), capacitance measurements (allows exocytosis to be followed at the level of single cells), calcium imaging using fluorescent dyes allows patterns of calcium movement within the cytoplasm to be tracked, fluorescence resonance energy transfer (FRET) enables protein-protein interactions to be evaluated, and molecular biology methods allow for the manipulation of the levels of expression of proteins of interest.

In other embodiments, a wide variety of assay methods are used to examine the modulation of intracellular calcium by compounds of Formula (I). Such assays include in vitro cell based assays as well as in vivo animal models. In some embodiments, are assays that detect, monitor or measure an effect on intracellular calcium, including calcium entry-mediated events. Such assays include, but are not limited to, assays monitoring, measuring and/or detecting intracellular calcium levels, modulation of calcium levels, and movement of calcium into, out of or within cells and intracellular organelles. In other embodiments are assays which also include monitoring, measuring and/or detecting calcium entry-mediated events and molecules involved in calcium entry-mediated events such as, but not limited to, signal transduction molecules, transcription factors, secreted molecules and other molecules that are affected by changes in calcium homeostasis. Assays include, but are not limited to, those described herein and those described in US patent publication no. 2007/0031814 and WO 07/081,804, herein incorporated by reference.

Cells and Cell Models

For in vitro testing of the modulation of intracellular calcium by compounds of Formula (I), a wide variety of cell types for such assays are available. In one embodiment, the cell is one in which store-operated calcium entry occurs or that is manipulated such that store-operated calcium entry occurs in the cell. In other embodiments, the cell contains one or more proteins involved in modulating intracellular calcium (and, in particular, is involved in, participates in and/or provides for store-operated calcium entry, movement of calcium into, out of or within an intracellular organelle or calcium store, modulation of calcium levels in an intracellular organelle or calcium store (e.g., endoplasmic reticulum) and/or calcium buffering), such as those provided herein. In further embodiments, the protein(s) include a STIM proteins (including STIM1, STIM2, DSTIM and CSTIM protein) and/or Orai proteins (Orai1, Orai2, Orai3). The cell optionally endogenously expresses the protein(s) or recombinantly expresses the protein(s).

In some embodiments, cells for use in the methods are of any species. In one embodiment, the cells are eukaryotic cells. In one embodiment, the cells are yeast, insect (e.g., *Drosophila* or *Anopheles*), or mammalian cells. Mammalian cells include, but are not limited to, rodent (e.g., mouse, rat and hamster), primate, monkey, dog, bovine, rabbit and human cells. A variety of cell types are used in the methods, including, for example, neuronal, nervous system, brain, immune system cells, e.g., T lymphocytes and B cells, primary cells, blood and hematopoietic cells, stromal cells, myeloid cells, lymphoid cells, and a variety of tumor and cancer cells. Particular cells include *Drosophila* Schneider 2 or S2 cells, human embryonic kidney (HEK293) cells, rat basophilic leukemia (RBL-2H3) cells, Jurkat cells, epithelial cells, rhabdomyosarcoma cells, rhabdoid cells, retinoblastoma cells, neuroepithelioma cells, neuroblastoma cells, osteosarcoma cells, fibroblasts, bone marrow stroma cells, erythroleukemia cells and lymphoblast cells. Other cell lines include HEK 293 and 293T, CHO (including CHO-K1), LTK-, N2A, H6, and HGB. Many such cells and cell lines are available through cell depositories such as, for example, the American Type Culture Collection (ATCC, Manassas, Va.). In further embodiments, primary cells are obtained by isolation from tissue sources. The generation, maintenance and use of such cells and cell lines is well known.

In other embodiments, cells from a known cell line are used, such as neuroblastoma SH-SY5Y cells, pheochromocytoma PC12 cells, neuroblastoma SK-N-BE(2)C or SK-N-SH cells, human SK-N-MC neuroepithelioma cells, SMS-KCNR cells, human LAN-5 neuroblastoma cells, human GI-CA-N neuroblastoma cells, human GOTO neuroblastoma cells, mouse Neuro 2a (N2A) neuroblastoma cells and/or human IMR 32 neuroblastoma cells, chronic myeloid leukemia cells (e.g., human K562 cells), promyelocytic leukemia cells (e.g., HL60 cells) and histiocytic lymphoma cells (e.g., U937 cells), Burkitt's lymphoma cells (e.g., CA46 cells), B-cells (e.g., NALM6), acute lymphoblastic leukemia cells (e.g., MOLT4 cells), T cells (e.g. Jurkat cells) and early T-ALL (e.g., DU528) cells.

The choice of a cell for use in an in vitro assay to test the modulation of intracellular calcium by compounds of Formula (I) involve several considerations, including, for example, a particular protein that is being used in the method and a particular aspect or activity of intracellular calcium modulation that is being monitored or assessed in the method.

In one embodiment, the modulation of intracellular calcium by a compound of Formula (I) is examined by monitoring or assessing the effect on store-operated calcium entry. Cells typically used in such methods exhibit store-operated calcium entry either naturally or through manipulation of the cells. In other embodiments, cells that endogenously exhibit store-operated calcium entry include some excitable cells and most non-excitable cells and are identified using methods described herein.

In one embodiment, it is desirable to utilize a cell that contains components of signaling and messenger systems that effects release of calcium from intracellular stores. For example, cells containing components of receptor-mediated phospholipase C(PLC) activation systems are used for physiological activation (via generation of $IP_3$) of store depletion to facilitate monitoring of store-operated calcium entry. Receptor-mediated PLC activation occurs through distinct coupling mechanisms: PLC-β activation by G protein-coupled receptors (GPCRs) and PLC-γ activation by tyrosine kinase receptors and nonreceptor tyrosine kinases. Thus, cells containing a receptor-mediated PLC-activation system are monitored or assessed for store-operated calcium entry upon agonist activation of one or more receptors known to participate in the system.

In another embodiment, an assessment of intracellular calcium after treatment with a compound of Formula (I) is made under a variety of conditions. Conditions are selected to evaluate the effect of test agent on a specific aspect of intracellular calcium. For example, reagents and conditions are known, and are used, for specifically evaluating store-operated calcium entry, resting cytosolic calcium levels, calcium buffering, and calcium levels of and calcium uptake by or release from intracellular organelles. in further embodiments, resting cytosolic calcium levels, intracellular organelle calcium levels and cation movement are assessed using any of the methods described herein. Such methods of assessing modulation in intracellular calcium include, but are not limited to, calcium-sensitive indicator-based measurements, such as fluo-3, mag-fura 2 and ER-targeted aequorin, labeled calcium (such as $^{45}Ca^{2+}$)-based measurements, and electrophysiological measurements. Particular aspects of ion flux that are assessed include, but are not limited to, a reduction (including elimination) in the amount of ion flux, altered biophysical properties of the ion current, and altered sensitivities of the flux to activators or inhibitors of calcium flux processes, such as, for example, store-operated calcium entry. Reagents and conditions for use in specifically evaluating receptor-mediated calcium movement and second messenger-operated calcium movement are also available.

Evaluation of Store-Operated Calcium Entry

In one aspect, compounds of Formula (I) are added to cells under conditions that permit store-operated calcium entry to occur in order to assess the effects of compounds of Formula (I) on store-operated calcium entry.

For example, in one method cells are treated to reduce the calcium levels of intracellular calcium stores and then analyzed for evidence of ion (e.g., calcium) influx in response thereto in the presence of a compound of Formula (I). Techniques for reducing calcium levels of intracellular stores and for analyzing cells for evidence of ion (e.g., calcium) influx are described herein.

In other methods, electrophysiological analysis of currents across a cell-detached plasma membrane patch or an outside-out membrane vesicle are used to detect or monitor store-operated channel currents (e.g., $I_{SOC}$, $I_{CRAC}$) in the presence of a compound of Formula (I).

Evaluation of Calcium Entry-Mediated Events

A number of molecules involved in calcium-regulated pathways are known. Evaluation of molecules involved in calcium-entry mediated events are used to monitor intracellular calcium, and are used, for example in screening assays described herein to monitor the effects of compounds of Formula (I). Examples of assays include but are not limited to assays which detect, or determine the presence, levels, alteration of levels, production, modification (such as phosphorylation and dephosphorylation), translocation, degradation and activity of molecules involved in calcium-entry mediated events (see for example, Trevillyan et al. (2001) *J. Biol. Chem.* 276:48118-26). In some embodiments, the assays described herein are used with cells that have been treated with or contacted with a compound of Formula (I), or that express an altered amount of a test molecule (such as a protein involved in calcium regulation, including a STIM protein, Orai protein), or with control cells. In other embodiments, the assays are also conducted in cells that have been stimulated with a physiological or non-physiological activator, or in unstimulated cells. The following are representative assays for molecules involved in calcium-entry mediated events and are meant to be exemplary only. Other assays for these molecules and assays for other molecules involved in calcium-entry mediated events are also employed in any of the screening and/or modulation methods described herein.

β-Hexosaminidase Release

In mast cells, $Ca^{2+}$ influx results in degranulation and release of inflammatory mediators such as heparin, histamine and enzymes such as β-hexosaminidase. In further embodiments, detecting and/or measuring release of such molecules is used to monitor intracellular calcium. For example, in other embodiments, media from mast cells are collected. In further embodiments, suitable substrate for β-hexosaminidase (e.g. p-nitrophenyl-acetyl-glucosamide) is then added and the absorbance of the resulting mixture assessed to measure the relative amount of β-hexosaminidase activity in the samples.

Calcium/Calmodulin-Dependent CaN Phosphatase Activity

The phosphatase calcineurin (CaN) dephosphorylates various proteins, affecting their activity and localization. In other embodiments, CaN activity is assessed by incubating purified CaN and a CaN substrate, for example a radiolabeled peptide corresponding to a sequence in the RII subunit of cAMP-dependent kinase, either with or without a compound of Formula (I) (see, Trevillyan et al. (2001) *J. Biol. Chem.* 276: 48118-26). In further embodiments, the level of radiolabeled peptide and/or the amount of free inorganic phosphate released is measured to assess CaN dephosphorylation activity.

NFAT Transcriptional Activity

The NFAT (nuclear factor of activated T cells) transcription factor regulates a number of genes in response to intracellular calcium levels. For example, NFAT proteins regulate the transcription of cytokine genes involved in the immune response. In other embodiments, promoters from NFAT-regulated genes, and/or regulatory regions and elements from these genes, are used to monitor NFAT regulated expression and thereby monitor intracellular calcium. In further embodiments, reporter gene fusions are constructed with NFAT regulated promoters or NFAT-regulated elements operably linked to a reporter gene such as luciferase, β-galactosidase, green fluorescent protein (GFP) or any other known reporter (see for example, Published U.S. Application no. 2002-0034728). The amount of reporter protein or activity is a measure of NFAT activity.

NFAT Phosphorylation

NFAT activation is regulated primarily through its phosphorylation, which in turn regulates its subcellular localization. In unstimulated cells, NFAT is a hyperphosphorylated cytosolic protein. An elevation in intracellular $Ca^{2+}$, induced by a variety of mechanisms, increases the activity of the $Ca^{2+}$-calmodulin-dependent phosphatase, calcineurin. Activated calcineurin dephosphorylates multiple serine residues within the regulatory region of the NFAT molecule. NFAT is rephosphorylated in response to decreases in $Ca^{2+}$ levels or CaN inhibition.

The phosphorylation state of NFAT is monitored for example, by expressing a detectably tagged NFAT protein in cells, such as a His6 tagged-NFAT. Tagged NFAT is purified from cells using $Ni^{2+}$ chromatography and subjected to gel electrophoresis and staining or western blotting. More highly phosphorylated forms of NFAT are distinguished by their slower migration. In further embodiments, the state of phosphorylated NFAT is used as a measure of NFAT activation (see, Trevillyan et al. (2001) *J. Biol. Chem.* 276:48118-26).

NFAT Nuclear Localization

NFAT localization between the cytoplasm and nucleus is regulated by the phosphorylation state of NFAT. Phosphorylation of NFAT prevents nuclear localization by masking the nuclear localization sequence. NFAT nuclear localization are monitored, for example, by expressing fluorescently tagged NFAT, for example, GFP-NFAT, in cells. In further embodiments, confocal microscopy is used to monitor nuclear localization of the tagged NFAT (see, Trevillyan et al. (2001) *J. Biol. Chem.* 276:48118-26).

Cytokine Secretion

In some embodiments, cytokine secretion, such as IL-2 secretion, is monitored using protein detection assays. For example, supernatant is collected from immune cells. In other embodiments, an ELISA assay or other suitable format with IL-2 antibodies is used to detect and/or measure the amount of IL-2 secreted as compared to control cells. Secretion of other cytokines, for example, TNF-α, is also detected in similar assays.

Cytokine Expression

Expression of cytokines, such as, but not limited to IL-2, are assessed either directly or indirectly in cells. For example, in indirect methods, an IL-2 promoter are operably linked to a reporter gene such as luciferase or β-galactosidase, and the reporter construct introduced into cells. In further embodiments, reporter gene expression is monitored and compared to gene expression in control cells (see, Trevillyan et al. (2001) *J. Biol. Chem.* 276:48118-26). In other embodiments, expression of endogenous or recombinant IL-2 mRNA or protein is assessed.

T Cell Proliferation

Cytokines such as IL-2 are necessary for T-cell proliferation in response to mitogen or alloantigen stimulation, and thus T-cell proliferation is altered by changes in cytokine expression or secretion. In some embodiments, T cells are induced, such as with concanavalin A or alloreactive lymphocytes and T cell proliferation measured, for example, by subjecting cells to a pulse of $^3$H-thymidine and measuring $^3$H-thymidine incorporation (see, Trevillyan et al. (2001) *J. Biol. Chem* 276:48118-26).

In further embodiments, the modulation (e.g. inhibition or reduction) of SOCE by compounds of Formula (I) is determined by evaluation of any of the following criteria:
a. there is direct inhibition of increased $[Ca^{2+}]_i$ as measured by a calcium indicator;
b. there is a direct inhibition of $I_{SOC}$ or $I_{CRAC}$ as measured by patch clamp;
c. there is inhibition of downstream signaling functions such as calcineurin activity, NFAT subcellular localization, NFAT phosphorylation, and/or cytokine, e.g., IL-2, production; or
d. there are modifications in activation-induced cell proliferation, differentiation and/or apoptotic signaling pathways.

Animal Models

Animal models that are used in embodiments of the methods further include animals, such as, but not limited to non-human animals, which have, in at least some of their cells, an alteration or defect in, or aberrant functioning of, a cellular process which relies on or is regulated by intracellular calcium. Cellular processes that rely on or are regulated by intracellular calcium include, for example, cellular activation, gene expression, cellular trafficking, and apoptosis. In some embodiments, are diseases/disorders that involve defects that are at least partially compensated for by modulation of intracellular calcium include, but are not limited to: autoimmune disorders, including rheumatoid arthritis, inflammatory bowel disease, Sjogren's syndrome (cytokines associated with lymphocyte invasion of salivary epithelial cells can reduce calcium mobilization in parotid cells; also, T-cell activation, including activation of transcription factors, cytokine gene expression and cell proliferation, depends on sustained elevation of intracellular calcium level provided by store-operated calcium influx), asthma (store-operated calcium entry also plays an important role in mediating bronchial chonstriction and bronchial smooth muscle cell proliferation), glomerulonephritis and glomerular inflammation (changes in intracellular calcium, such as by store-operated calcium entry, signal monocyte adhesion in a co-culture model of glomerular inflammation).

Types of animal models include, but are not limited to, non-human animals, such as non-human invertebrates and vertebrates and non-human mammals, rodents (e.g., mice, rat and hamster), cows, chickens, pigs, goats, dogs, sheep, insects, *Drosophila*, nematodes, worms, *C. elegans*, monkeys, gorillas, and other primates.

Animal models include transgenic and non-transgenic animals. One example of such an animal model that are used in particular embodiments of the methods is a rodent model of airway hyperresponsiveness (AHR), a characteristic of asthma. This model are generated, for example, by sensitization through immunization with ovalbumin followed by exposure to aerosolized ovalbumin and challenge by cholinergic stimulation (e.g., via administration of methacholine or acetylcholine) (see, e.g., Xu et al. (2002) *J. Appl. Physiol.* 93:1833-1840; Humbles et al (2002) *Proc. Natl. Acad. Sci.* 99:1479-1484). Airway hyperresponsiveness (which in some embodiments are evaluated using methods such as, for e.g., using barometric plethysmography to record respiratory pressure curves and through measurement of pulmonary parameters such as pulmonary conductance and pulmonary compliance) are assessed and compared in animals treated and not treated with a compound of Formula (I). A further example of an animal model that is used in embodiments of the methods is a rodent model of mesangial proliferative glomerulonephritis, which is generated, for example, by administration of anti-Thy1.1 antibody (see, e.g., Jefferson and Johnson (1999) *J. Nephrol.* 12:297-307). Any number of parameters indicative of glomerulonephritis or renal dysfunction (e.g., mesangial cell proliferation, blood pressure, urinary protein excretion, creatinine clearance, glomerulosclerosis index and other parameters) are in some embodiments, evaluated and compared in animals treated with and not treated with test agent. The non-obese diabetic (NOD) mouse, an inbred mouse strain that spontaneously develops an autoimmune diabetes that shares many immunogenetic features with Type 1 diabetes mellitus, is another example of an animal model that is used in one embodiment of the methods. These mice also manifest many characteristics of autoimmune exocrinopathy (such as Sjorgen's syndrome) including declining exocrine tissue secretory function (see, e.g., Humphreys-Beher and Peck (1999) *Arch. Oral Biol.* 44 Suppl 1:S21-25 and Brayer et al. (2000) *J Rheumatol.* 27:1896-1904). Characteristics relevant to Sjorgen's syndrome (e.g., lymphocytic infiltrates in exocrine glands (e.g., salivary and lacrimal glands), presence of dendritic cells and macrophages in submandibular glands, integrity of the lacrimal gland by measurement of basal and stimulated tear secretion, saliva flow rates and amylase activity) are evaluated and compared in animals treated with and not treated with a compound of Formula (I). In further embodiments, an animal (e.g., rodent) model of autoimmune disease is also used in particular embodiments of the methods. Such animals include rat models available through the National Institutes of Health (NIH) Autoimmune Rat Model Repository and Development Center (Bethesda, Md.; accessible at www.ors.od.nih.gov/dirs/vrp/ratcenter). One rat model of rheumatoid arthritis (RA) and related chronic/inflammatory autoimmune diseases is the collagen-induced arthritis (CIA) model (see, e.g., Griffiths and Remmers (2001) *Immunol. Rev.* 184:172-183). Characteristic phenotypes of autoimmune disease (e.g. altered levels of immune reactivity to self-antigens, chronic inflammation of autoantigen-expressing target organs, and activation and participation of invading mononuclear cells and tissue fibroblasts in organ damage) are in some embodiments, evaluated and compared in animals treated with and not treated with a compound of Formula (I). In other embodiments, an animal (e.g., rodent) model of neuropathic or inflammatory pain is also used in one embodiment of the methods. For example, one rat model of neuropathic pain involves development of tactile allodynia (exaggerated response to otherwise innocuous stimuli) after ligation of lumbar spinal nerves (see, e.g., Chaplan et al. (1994) *J. Neurosci. Methods* 53:55-63 and Luo et al. (2001) *J. Neurosci.* 21:1868-1875). Tactile allodynia, one characteristic feature of neuropathic pain, are evaluated (e.g., by evaluating paw withdrawal threshold in response to application of pressure) and compared in animals treated and not treated with a compound of Formula (I).

EXAMPLES

These examples are provided for illustrative purposes only and not to limit the scope of the claims provided herein. The starting materials and reagents used for the synthesis of the compounds described herein are synthesized or are obtained from commercial sources, such as, but not limited to, Sigma-Aldrich, Acros Organics, Fluka, and Fischer Scientific. In some embodiments, the compounds described herein are synthesized by techniques and methods known to a person of ordinary skill in the art.

Biological Examples

In Vitro Examples

Example 1

In Vitro Screening for Agents that Modulate Intracellular Calcium Levels

Fluorescence-based assays are used for screening the compounds described herein, such as compounds of Formula (I) which modulate intracellular calcium.

A. Fluorescence-Based Assay of Store-Operated Calcium Entry in Orai1/STIM1 Stable Cells.
Cells:
Cells stably expressing recombinant human STIM1 and Orai1 were generated by transfecting a human Orai1 expression plasmid (pcDNA3.1-Orai1-cmyc) into HEK-293 cells stably overexpressing human STIM1 (Roos et al. 2005 JCB 169(3): 435-445). Colonies of cells stably expressing both STIM1 and Orai1 proteins were selected and then subcloned by limiting dilution. Cells were cultured at 37° C./6% $CO_2$ in complete medium with 10% FBS and appropriate selection markers.
Assay
The day prior to performing the assay Orai1/STIM1 stable cells are plated in 50 μL of complete medium at 90-95% confluence in a 384 well plate. Cells are grown at 37° C./6% $CO_2$ overnight. On the day of the assay, 1.5 μM fluo-4-AM (Invitrogen) in complete medium is added to the cells, which are then incubated for 1 hour at RT. Cells are washed once in $Ca^{2+}$-free HBSS (Hank's buffered saline solution) and 35 μl of $Ca^{2+}$-free HBSS is added to each well. Test compounds are added to wells in a 10 μL $Ca^{2+}$-free HBSS solution, prepared at 4.5× the desired final concentration, and incubated for 30 minutes at RT. The initial baseline fluorescence signal is then measured with a FLIPR[384] (Molecular Devices) plate reader. Calcium entry is initiated by adding 5 μl of 10×$CaCl_2$ (10 mM) in HBSS, and changes in cellular fluorescence are measured with the FLIPR[384] plate reader. In each well, the magnitude of the fluorescence signal as a result of calcium entry into the cell is determined by calculating the difference between the peak fluorescence signal measured after calcium addition and the initial baseline fluorescence signal (designated Peak-Basal). $IC_{50}$ values are typically calculated as the concentration that inhibited 50% of the Peak-Basal signal.

B. Fluorescence-based Assay of Store-Operated Calcium Entry in RBL-2H3Cells.
Cells:
RBL-2H3 cells are obtained from ATCC and maintained in complete medium with 10% FBS at 37° C./6% $CO_2$.
Assay:
The day prior to performing the assay, RBL-2H3 cells are plated in 50 μL of complete medium in a 384 well plate. Cells are grown at 37° C./6% $CO_2$ overnight and grow to 50-60% confluence by the next day. On the assay day, 1.5 μM Fluo-4-AM dye (Invitrogen) in complete medium is added and incubated for 1 hour at RT. Cells are washed twice in $Ca^{2+}$-free HBSS buffer and 35 μL $Ca^{2+}$-free HBSS buffer is added to each well. 10 μL of a test compound prepared in a $Ca^{2+}$-free HBSS solution at 4.5× of the desired concentration is added to a well and incubated for 5 minutes at RT. 10 μL of thapsigargin prepared in a $Ca^{2+}$-free HBSS solution at 5.5× of the desired concentration (5.5 uM) is added to each well and incubated for an additional 25 minutes. The initial baseline fluorescence signal is measured with a FLIPR[384] (Molecular Devices) plate reader. 5 μL of 12× calcium in HBSS (12 mM) is added and changes in cellular fluorescence are measured with the FLIPR[384] plate reader. In each well, the change in the fluorescent signal as a function of time due to calcium entry into the cell is determined by calculating the difference between the fluorescent signal measured 7 seconds after calcium addition and the initial baseline fluorescence signal at time zero (t=0). This parameter is designated Upslope. The $IC_{50}$ value is calculated as the concentration at which 50% of the Upslope is inhibited.

C. Fluorescence-based Assay of Store-Operated Calcium Entry in Jurkat Cells.
Cells:
Jurkat E6-1 cells were obtained from ATCC and maintained in complete medium with 10% FBS at 37° C./6% $CO_2$.
Assay:
The day prior to performing the assay, Jurkat E6-1 cells are seeded at a density of 2 million cells/mL in complete medium in a T-175 flask. Cells are grown at 37° C./6% $CO_2$ overnight. On the following day, 1.5 μM Fluo-4-AM dye (Invitrogen) in complete medium is added and incubated for 1 hour at RT. Cells are harvested, washed twice in $Ca^{2+}$-free HBSS buffer and plated in 35 μL $Ca^{2+}$-free HBSS buffer in a 384 well plate. 10 μL of a test compound prepared in a $Ca^{2+}$-free HBSS solution at 4.5× of the desired concentration is added to a well and incubated for 5 minutes at RT. 10 μL of thapsigargin prepared in a $Ca^{2+}$-free HBSS solution at 5.5× of the desired concentration (5.5 uM) is added to each well and incubated for an additional 25 minutes. The initial baseline fluorescence signal is measured with a FLIPR[384] (Molecular Devices)

plate reader. 5 μL of 12× calcium in HBSS (12 mM) is added and changes in cellular fluorescence are measured with the FLIPR[384] plate reader. In each well, the change in the fluorescent signal as a function of time due to calcium entry into the cell is determined by calculating the difference between the fluorescent signal measured 7 seconds after calcium addition and the initial baseline fluorescence signal at time zero (t=0). This parameter is designated Upslope. The $IC_{50}$ value is calculated as the concentration at which 50% of the Upslope is inhibited.

Example 2

In Vitro $I_{CRAC}$ Patch Clamp Assay

Objective

The objective of this assay is to examine the in vitro effects of test compounds on cloned CRAC channels (Orai1 and STIM1 genes stably expressed in HEK293 cells), responsible for $I_{CRAC}$, the calcium release activated calcium channel current.

Test and Control Articles

Formulation: Test article stock solutions are prepared in dimethyl sulfoxide (DMSO) and stored frozen. Test article concentrations are prepared fresh daily by diluting stock solutions into an appropriate external recording buffer. If necessary, test article formulations are sonicated (Model 2510, Branson Ultrasonics, Danbury, Conn.), at ambient room temperature to facilitate dissolution. In certain instances, the test solutions contain up to 0.1% DMSO and the presence of 0.1% DMSO does not affect channel current.

Test Article Concentrations and Quantity

Typically, the effects of three (3) concentrations of each test article are evaluated (0.1, 1, and 10 μM). Test articles are weighed and prepared as 30 mM or 10 mM stock solutions in DMSO. The DMSO stock is diluted in external recording buffer to prepare a 10 μM test solution (final DMSO 0.03% or 0.1%). The 10 μM test solution is diluted in external recording buffer to prepare 1 μM and 0.1 μM test solutions. Test solutions contain up to 0.1% DMSO at the highest concentration which are diluted in test solutions at lower concentrations.

Positive Control Article

Stock solutions of the positive control article are prepared in batches, aliquoted for individual use, stored frozen and used within six months. The positive control concentration is prepared fresh daily by diluting stock solutions into external recording buffer. The final DMSO concentration in the test positive control article is up to 0.1% of the solution.

Negative Control Article

The negative control article is 0.1% DMSO in external recording buffer.

Cloned Ion Channel Test Systems

Cells are maintained in tissue culture incubators per CalciMedica standard protocols. Stocks are maintained in cryogenic storage. Cells used for electrophysiology are plated in plastic tissue culture dishes.

HEK293 Cells

HEK293 cells are stably transfected with the appropriate ion channel cDNAs (Orai1/STIM1). Cells are cultured in DMEM (Gibco 11960) supplemented with 10% fetal bovine serum (Gibco 10082), 100 U/mL penicillin G sodium, 1 mM Na pyruvate (Gibco 11360), 100 μg/mL streptomycin sulfate (Gibco 10378), 0.5 mg/ml geneticin (Gibco 10131-035) and 50 μg/ml zeocin (Invitrogen 45-0430). Cells should be maintained at ≦80% confluence. The day before testing, cells in culture dishes are washed once with calcium/magnesium-free D-PBS, treated with trypsin/EDTA and re-suspended in the culture media and counted. Cells are then diluted in culture medium with 1% fetal bovine serum and plated at low density (5-10K) onto poly-D-lysine coated glass coverslips in 24-well tissue culture dishes and placed in a tissue culture incubator set at 37° C. in a humidified 95% air, 6% $CO_2$ atmosphere.

Test Methods

Recording Chamber and Perfusion of Test Articles

Glass coverslips containing cells are transferred to a recording chamber (Warner Instruments) with continuous perfusion of external recording buffer. During recordings of $I_{CRAC}$, all treatments are delivered by gravity-fed bath perfusion from disposable syringe reservoirs via disposable polyethylene tubing feeding into a Teflon manifold. The flow rate is set between 1.2-1.5 ml/min assuring complete solution exchange in ~1 min. All experiments are performed at ambient temperature.

Test Article Treatment Groups

For experiments where the test article is applied for 10 minutes the treatment paradigm is summarized in Table 1. Control recording buffer is perfused for five (5) minutes while $I_{CRAC}$ develops and a stable baseline is established; each cell is used as its own control. Each test article is applied to naïve cells (n≧2, where n=the number cells/concentration; at 1 concentration/cell) for a duration of ten (10) minutes (Table 1). The test article is washed off for ten (10) minutes to look for reversibility of the effect. External recording saline with no calcium is perfused for two (2) minutes to determine the background current in the absence of $I_{CRAC}$. Control saline containing calcium is reapplied for three (3) minutes.

For experiments where the test article is applied for 30 minutes prior to recording of $I_{CRAC}$, the treatment paradigm is summarized in Table 2. Prior to the start of each experiment, cells are incubated with compound for 30 minutes at room temperature, and compound remains present throughout $I_{CRAC}$ recordings. Control cells are exposed to vehicle only. After break-in and establishment of the whole-cell patch clamp configuration, recording buffer±compound is perfused for ten (10) minutes. At the end of the 10 min period the amplitude of $I_{CRAC}$ is measured. The effects of compounds are determined by comparing the $I_{CRAC}$ signal in cells pretreated with compound to the signal in cells pretreated with vehicle.

TABLE 1

Test Article Schedule for 10-minute Application Studies

| Epoch | Solution | Exposure time |
|---|---|---|
| 1 | Baseline control/stabilization | 5 minutes |
| 2 | Test article | 10 minutes |
| 3 | Wash | 10 minutes |
| 4 | 0 calcium | 2 minutes |
| 5 | control | 3 minutes |

TABLE 2

Test Article Schedule for 40-minute Application Studies

| Epoch | Solution | Exposure time |
|---|---|---|
|   | Test article | 30 minutes |
| 1 | Test article | 10 minutes |
| 2 | Wash | 10 minutes |
| 3 | 0 calcium | 2 minutes |
| 4 | control | 3 minutes |

Control Treatment Groups

As a negative control, 0.1% DMSO is applied to naïve cells (n≧2, where n=the number cells. This is used to monitor the magnitude of rundown of $I_{CRAC}$. As a positive control, 1 μM of 4-(4-bromophenyl)-2-(3-fluorobenzamido)thiophene-3-carboxylic acid is routinely applied to naïve cells (n 2, where n=the number cells).

Whole Cell Patch Clamp Procedures

Standard whole cell patch clamp procedures are used. The compositions of the extracellular and intracellular solutions are shown in Tables 3 and 4. Cells are visualized on an inverted microscope (Olympus IX71) and voltage clamped using a Multiclamp 700B amplifier and PClamp software (Axon Instruments). Briefly, borosilicate patch pipettes filled with intracellular solution (Appendix 1) are positioned onto the cell membrane. Once a GΩ seal is formed, suction is applied until the patch ruptures and the whole cell configuration is established. The quality of the configuration will be evaluated with the "membrane test" in Clampex to determine cell capacitance (Cm), input resistance (Rm), access resistance (Ra), and holding current at −50 mV (Ih). Data are stored on the CalciMedica computer network (and backed-up nightly) for off-line analysis.

TABLE 3

| Extracellular Solution Composition (concentration in mM) | |
|---|---|
| NaCl | 120 |
| TEA-Cl | 10 |
| HEPES | 10 |
| CaCl$_2$ | 10 (and 0) |
| MgCl$_2$ | 2 (and 12) |
| glucose | 10 |

The pH is adjusted to 7.2 with NaOH and the final osmolarity is adjusted to 325 with sucrose. Solutions are prepared daily. Chemicals used in solution preparation are purchased from Sigma-Aldrich (St. Louis, Mo.), unless otherwise noted, and are of ACS reagent grade purity or higher.

TABLE 4

| Intracellular Solution Composition (concentration in mM) | |
|---|---|
| Cs-glutamate | 120 |
| HEPES | 10 |
| BAPTA | 20 |
| MgCl$_2$ | 3 |

The pH is adjusted to 7.2 with CsOH. Solutions are prepared in batches, aliquoted, and refrigerated until use. A fresh aliquot is used each day and stored on ice throughout the day. Chemicals used in solution preparation are purchased from Sigma-Aldrich (St. Louis, Mo.), unless otherwise noted, and are of ACS reagent grade.

Figure 2:
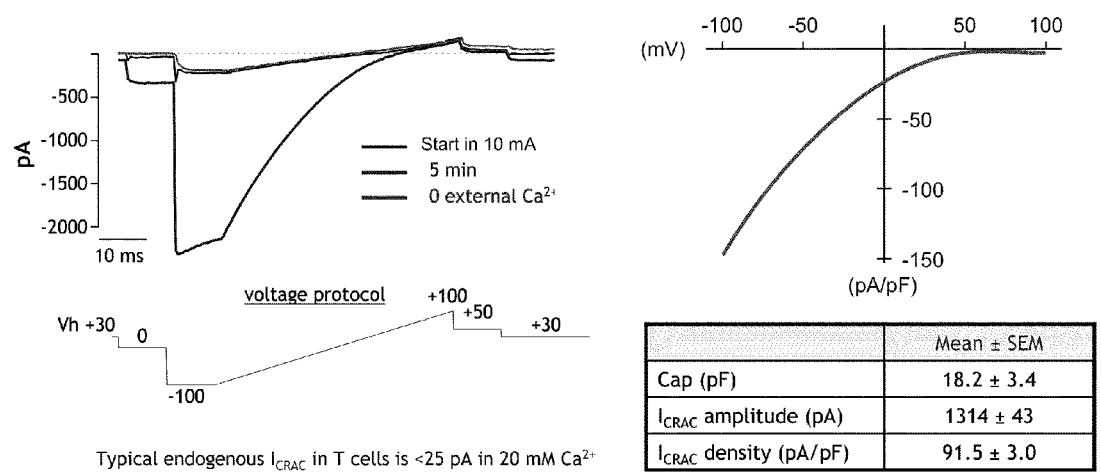
FIG. 2 shows the typical $I_{CRAC}$ traces in cells stably overexpressing human Orai 1 and STIM 1 in response to the voltage stimulus immediately after break-in, before $I_{CRAC}$ is activated, and at 5 min after $I_{CRAC}$ is fully activated by depletion of intracellular calcium stores.

$I_{CRAC}$ Test Procedures $I_{CRAC}$ from the Orai1/STIM1 channel complex is activated by passive depletion of intracellular calcium stores using 20 mM BAPTA in the intracellular solution. Voltage clamp data is acquired using Clampex software to elicit a stimulus voltage protocol (shown in Table 5) applied every six (6) seconds. Currents are digitized at 10 kHz and filtered at 2 kHz. Whole cell capacitive compensation is employed. Representative $I_{CRAC}$ traces are shown in FIG. 2.

TABLE 5

| Voltage Clamp Protocol | |
|---|---|
| Voltage | Description |
| Vh +30 mV | to minimize calcium entry in-between sweeps |
| Vstep to 0 mV for 10 ms | to evaluate "zero" current |
| Vstep to −100 mV for 10 ms | to measure $I_{CRAC}$ at high driving force |
| Vramp to +100 mV over 50 ms | to monitor inwardly rectifying profile of $I_{CRAC}$ |
| Vstep to +50 mV for 10 ms | to estimate leak current |

Data Analysis

Data analysis is performed using Clampfit software. $I_{CRAC}$ is measured at −100 mV and the current measured after 5 min is used as the baseline control. For 10-minute application studies, the current measured after 10 min application of the test article is normalized to the baseline current and expressed as % control. For 40-min application studies, the current measured at the end of 10 minutes of $I_{CRAC}$ recording time is used as the comparator. The current measured in "0 calcium" buffer is used to subtract background leak current. Data points for each test article concentration (n≧2) are fitted to a sigmoid function (SigmaPlot) to determine the IC$_{50}$ and Hill slope.

In Vivo Examples

Example 3

In Vitro Assay of Mast Cell Degranulation

Cells:
RBL-2H3 cells were obtained from ATCC and maintained in complete medium with 10% FBS at 37° C./6% CO$_2$.

Assay:
a) Stimulation with 1 μM thapsigargin/20 nM TPA

The day prior to performing the assay, RBL-2H3 cells are plated in a 96 well plate. Cells are grown at 37° C./6% CO$_2$ overnight. On the following day, cells are washed twice in HBSS Buffer with 1.8 mM CaCl$_2$ and 1.75% fetal bovine serum (FBS). 70 μL of a test compound prepared in HBSS Buffer with 1.8 mM CaCl$_2$+1.75% FBS is added and incubated for 10 minutes at 37° C./6% CO$_2$. Cells are stimulated by the addition of 7 μL of 11× thapsigargin/TPA (11 μM thapsigargin/220 nM TPA) and incubated at 37° C./6% CO$_2$ for 120 minutes. Media is collected and cell lysates are prepared by the addition of 70 μL of 0.05% Triton X-100 in HBSS with 1.8 mM CaCl$_2$. Levels of β-hexosaminidase are measured in both the media and the cell lysates. The β-hexosaminidase assay is performed by adding 40 μL of 1 mM p-nitrophenyl-acetyl-glucosamide substrate in 0.05M sodium citrate (pH 4.5) to 10 μL of sample (conditioned medium or cell lysate), incubating 60 minutes at 37° C., then adding 100 μL 0.05M sodium carbonate/0.05M sodium bicarbonate (pH 10.5), mixing thoroughly and reading the absorbance at 405 nm. The percentage of β-hexosaminidase released is calculated as follows: A405 (media)/[A405 (media)+A405 (lysate)]. The IC$_{50}$ value is calculated as the concentration at which 50% of the β-hexosaminidase released in vehicle treated cells is inhibited.

b) Stimulation with IgE-DNP

The day prior to performing the assay, RBL-2H3 cells are plated in 200 μL of complete medium in a 96 well plate for 1 hour. 20 μL of 11×DNP-IgE are added and cells are grown at 37° C./6% CO$_2$ overnight. On the following day, cells are washed twice in HBSS Buffer with 1.8 mM CaCl$_2$ and 1.75% fetal bovine serum (FBS). 70 µL of a test compound prepared in HBSS Buffer with 1.8 mM $CaCl_2$ and 1.75% is added and incubated for 10 minutes at 37° C./6% $CO_2$. Cells are stimulated by the addition of 7 µL of 11×DNP-BSA and incubated at 37° C./6% $CO_2$ for 30 minutes. Media is collected and cell lysates are prepared by the addition of 70 ul of 0.05% Triton X-100 in HBSS with 1.8 mM $CaCl_2$. Levels of β-hexosaminidase are measured in both the media and the cell lysates. The β-hexosaminidase assay is performed by adding 40 µL of 1 mM p-nitrophenyl-acetyl-glucosamide substrate in 0.05M sodium citrate (pH 4.5) to 10 µL of sample (conditioned medium or cell lysate), incubating 60 minutes at 37° C., then adding 100 µL 0.05M sodium carbonate/0.05M sodium bicarbonate (pH 10.5), mixing thoroughly and reading the absorbance at 405 nm. The percentage of β-hexosaminidase released is calculated as follows: A405 (media)/[A405 (media)+A405 (lysate)]. The $IC_{50}$ value is calculated as the concentration at which 50% of the β-hexosaminidase released in vehicle treated cells is inhibited.

Example 4

In Vitro Assay of Cytokine Release from T Cells

Cells:
Jurkat E6-1 cells are obtained from ATCC and maintained in complete medium with 10% FBS at 37° C./6% $CO_2$.
Assay:
The day prior to performing the assay, Jurkat T cells are plated in 90 µL of HBSS Buffer with 1.8 mM $CaCl_2$ and 1.75% fetal bovine serum (FBS) in a 96 well plate at a density of 1.5×105 cells/well for 3 hours. 10 µL of 10× test compound prepared in HBSS is added and incubated for 10 minutes at 37° C./6% $CO_2$. Cells are stimulated by the addition of 10 µL of 11×PHA/TPA (27.5 µg/mL PHA/880 nM TPA) and incubated at 37° C./6% $CO_2$ for 20 hours. On the following day, the supernatants are collected and assayed for IL-2 levels by ELISA according to the manufacturer's protocols. The $IC_{50}$ value is calculated as the concentration at which 50% of secreted IL-2 in vehicle treated cells is inhibited.

Example 5

Dose-Response Effects of a Compound of Formula (I), CSA or Rapamycin in Mouse Footpad DTH Purpose: Determine dose-response effects of Test Compound on mBSA induced DTH response in foot pads when dosing is done during the sensitization as well as induction phase.
Animals: Male Swiss Webster Mice approx. 20-25 grams at start of study.
Materials: Methylated BSA (Sigma) Freund's complete adjuvant (Difco) plus supplemental *M. tuberculosis* H37 RA (Difco).
General Study Design:
Mice are anesthetized with Isoflurane and given intradermal antigen injections of 0.1 ml at the base of the tail (D0, D07). Antigen is prepared by making a 4 mg/ml solution in sterile water. Equal volumes of antigen and Freund's complete adjuvant to which 4 mg/ml MTB are added (sonicate for 5 minutes after adding MTB to oil), are emulsified by hand mixing until a bead of this material holds its form when placed in water. Treatment with test compound is initiated on day 0, qd (24 hr intervals) and continued through day 10 when challenge is done.

On day 10 animals are injected into the right hind footpad with 20 µl of 10 mg/ml mBSA. Five unsensitized males are injected with mBSA into the footpad. Twenty-four hours later (day 11) the right and left hind paws are transected at the medial and lateral malleolus and weighed and the weight difference induced by injection of antigen is determined.

Statistical Analysis. Paw weights (mean±SE) for each group are analyzed for differences using a Student's t test or ANOVA with Dunnett's post test. Statistical significance is set at $p \leq 0.05$.

TABLE 5

Treatment Groups Males

| Group | N | Treatment 10 ml/kg qd, po |
|---|---|---|
| 1 | 5 | Normal controls (no sensitization) Inject mBSA into right only |
| 2 | 8 | DTH + Vehicle (70% PEG400/30% Water) |
| 3 | 8 | DTH + Test Compound (50 mg/kg, po, qd) |
| 4 | 8 | DTH + Test Compound (100 mg/kg, po, qd) |
| 5 | 8 | DTH + Test Compound (200 mg/kg, po, qd) |
| 6 | 8 | DTH + Test Compound (300 mg/kg, po, qd) |
| 7 | 8 | DTH + CSA (100 mg/kg qd, ip) |
| 8 | 8 | DTH + Rapamycin (5 mg/kg qd, ip) |

Example 5A

Pharmacokinetic Data of a Compound of Formula (I) in Rats

The bioavailability and plasma pharmacokinetic properties in rats of Compound of Formula (I) administered orally in 25% PEG400/20% ethanol/55% $H_2O$ vehicle. Two treatment groups, 1) an i.v. dose group at 2 mg/kg; and 2) an oral dose group at 10 mg/kg are administered to Male Sprague-Dawley rats (3 rats per group), weighing approximately 250-300 gm. Up to 10 time points are collected for each group. Typical time points are: predose, 15, 30 minutes, 1, 2, 4, 6, 8, 12 and 24 hrs. Up to 300 µL of whole blood are collected via jugular vein cannula at each time point. Whole blood is collected into anticoagulant containing microcentrifuge tubes and centrifuged at 5000 rpm in a microcentrifuge for 5 minutes before plasma is transferred to a clean microcentrifuge tube. The plasma samples undergo bioanalytical analysis.

Example 6

Effect of Test Compound in Rat Collagen Induced Arthritis (CIA) Model

Purpose: Determine efficacy of Test Compound administered by oral dosing qd, in inhibiting the inflammation, cartilage destruction and bone resorption of developing type II collagen arthritis in rats.
Animals:
Female Lewis rats (Charles River#7246950), weighing 125-150 g at the start of the study. 40 rats are injected with collagen to get solid responders on days 10 and 11. Four nonimmunized animals serve as normal controls.
Materials:
Test Compound, Type II collagen, Freund's incomplete adjuvant, acetic acid. Test Compound is prepared at a concentration of 10 mg/ml in 50% PEG400/50% water. Collagen is prepared by making a 4 mg/ml solution in 0.01N Acetic acid. Equal volumes of collagen and Freund's incomplete adjuvant, are emulsified by hand mixing until a bead of this material holds its form when placed in water.

General Study Design:

Animals (10 rats/group for arthritis, 4 rats/group for normal control).

Animals in the arthritis groups are anesthetized with isoflurane and given collagen injections (D0); each animal gets 300 µl of the mixture spread over 3 subcutaneous sites on the back. On Day 6 (D6) the animals are anesthetized again and given a second collagen injection, as before.

Oral dosing of Test Compound at 24 hour intervals (qd) is initiated on Day 0 using a dose volume of 5 ml/kg for oral solutions. Rats are weighed on Days 0, 3, 6, and 9-17 of arthritis, and caliper measurements of ankles taken every day beginning on Day 9. Final body weights are taken on Day 17 of arthritis. On Day 17, all animals are anesthetized for terminal blood draw and then euthanized. Subsequently, hind paws and knees are removed, the hind paws are weighed and then (with knees) placed in formalin for processing for microscopy. Livers, spleen and thymus and kidneys are also removed, trimmed of extraneous tissue and weighed. Kidneys are retained in formalin for histopathology.

Sampling will occur over 1 day and involves groups 2-5 with samples retained from all groups. This results in all animals being treated similarly and is important for clinical parameters and final liver weights.

Example 7

Effect of Compounds of Formula (I) on DNBS-Induced Colitis in Rats

Procedure: Male Wistar rats weighing 200±20 g are fasted for 24 hours prior to use. Distal colitis is induced by intracolonic instillation of DNBS (2,4-dinotrobenzene sulfonic acid, 20 mg in 0.5 ml ethanol 30%) with a catheter of 12 cm in length, followed by gentle injection of air (2 ml) through the catheter to ensure that the solution remain in the colon. The animals are divided into groups of 5 each. Test substance and vehicle are administered either daily or twice daily by appropriate route of administration 24 hour and 1 hour before DNBS instillation and then for 6 consecutive days thereafter. One normal control group is treated with 0.9% NaCl alone without DNBS challenge. The animals are sacrificed 12 hours after the final bid dose and 24 hours after the final daily dose and the colon is removed and weighed. During the experiment, body weight, fecal occult blood and stool consistency are monitored daily. Furthermore, when the abdominal cavity is opened before removal of the colon, adhesions between the colon and other organs are noted as is the presence of colonic ulceration after removal and weighing of each colon (a macroscopic damage score is recorded according to established score criteria). The colon-to-body weight ratio is calculated according to the formula: Colon (g)/BW×100. The "Net" increase in ratio of Vehicle-control+DNBS group relative to Vehicle-control group is used as a base for comparison with individual treated groups and expressed as "Dec. (%)" (percent decrease). A 30% or more ($\geq$30%) reduction in colon-to-body weight ratio, relative to the vehicle treated control group, is considered significant.

Sulfasalazine is used as the standard test agent. (Hogaboam C M, et al., An orally active non-selective endothelin receptor antagonist, bosentan, markedly reduces injury in a rat model of colitis. *Eur J Pharmacol*. 309: 261-269, 1996; Yue G, et al., In some embodiments, the 21-aminosteroid tirilazad mesylate ameliorates inflammatory bowel disease in rats. *J Pharmacol Exp Ther.* 276: 265-270, 1996.)

Example 8

Effect of Compounds of Formula (I) on Rejection of Skin Transplants in Rats

Procedure. Specific pathogen free Lewis and Brown Norway rats 10 weeks of age are purchased from Charles River and housed under clean conventional conditions. The animals are handled and allowed to acclimatize for a period of two weeks. Skin donors: female Brown Norway rats, 10 weeks of age. Skin recipients: female Lewis rats, 10 weeks of age.

The donor Brown Norway rats are killed to serve as donors of 5 to 8 skin transplants. Directly after killing the Brown Norway rats, the abdominal skin of the rats is shaved and skin transplants of 20 mm in diameter in size are taken. After removal of connective tissue, these grafts are transplanted onto Lewis rats. This is performed by shaving the upper dorsal skin of the Lewis rat under isoflurane anesthesia, removing a piece of skin of 15 mm in diameter by punching and replacement with a skin transplant derived from the Brown Norway rat.

During the study each graft is fixated by 4-6 stitches using Safil 6/0 violet (B Braun, Aesculap) and covered by Paraffin Gauze Dressing BP (3×3 cm, Smith & Nephew), a piece of gauze and surgical tape. This adaptation minimizes the chance of loosing a transplant for reasons different from rejection.

In all cases, transplants are protected with a bandage; these are removed after six days to enable daily inspection of the transplant.

Rejection is monitored by evaluating first signs of inflammation (redness) and necrosis (hardening and blackening of the graft).

Phase II Clinical Trial of the Safety and Efficacy of Compounds of Formula (I) in Patients with Active Rheumatoid Arthritis.

The purpose of this phase II trial is to investigate the safety, tolerability, PK, PD, and efficacy of single and repeat intravenous infusions of a compound of Formula (I) in patients with active rheumatoid arthritis.

Patients: Eligible subjects will be men and women between the ages of 18 and 75

Criteria:

Inclusion Criteria:

All subjects must use acceptable contraception to ensure that no pregnancies occur during the course of the study and for at least 12 weeks after dosing for males and for 32 weeks after dosing for females;

Body mass index within the range 18.5-35 kg/m$^2$ inclusive, in addition to a weight range of 55-95 kg;

The subject must be capable of giving informed consent and can comply with the study requirements and timetable;

The subject must have a diagnosis of RA according to the revised 1987 criteria of the American College of Rheumatology (ACR);

The subject must have a DAS28 disease activity score of greater than 4.2 at screening and pre-dose;

The subject must have a CRP serum level of >/0.5 mg/dl or an ESR level 28 mm/hour at screening and pre-dose;

The subject has NOT received any biological therapy in the past, including biologicals for the treatment of rheumatoid arthritis;

The subject must have liver function tests including alanine transaminase (ALT) and aspartate transaminase (AST) within 1.5 times the upper limit of normal (ULN) and alkaline phosphatase (ALP) within 3 times ULN at screening. The patient must also have total bilirubin within the ULN at screening;

The subject must have received at least 3 months of methotrexate and must be on a stable dose of methotrexate (up to 25 mg/week) for at least 8 weeks prior to screening and be willing to remain on this dose throughout the study;

If sulfasalazine is being taken in addition to methotrexate, the subject must be on a stable dose for at least 4 weeks prior to screening and be willing to remain on this dose throughout the study;

If hydroxychloroquine or chloroquine is being taken in addition to methotrexate, the subject must be on a stable dose for at least 3 months prior to screening and be willing to remain on this dose throughout the study;

Those subjects on other oral anti-rheumatic therapies, which may include Non Steroidal Anti Inflammatory Drugs (NSAIDs), COX-2 inhibitors, oral glucocorticoids e.g. prednisolone (~10 mg/day) must be on stable dosing regimens for at least 4 weeks prior to screening and be willing to remain on this regime throughout the study. Subjects receiving intramuscular glucocorticoids e.g methylprednisolone (~120 mg/month) must be on a stable dosing regimen for at least 3 months prior to screening and be willing to remain on this regimen throughout the study;

The subject must be on a stable dose of folate supplements (5 mg/week) for at least 4 weeks prior.

Exclusion Criteria:

Any clinically relevant abnormality identified on the screening medical assessment, laboratory examination (e.g. haematology parameter outside the normal limits), or ECG (12 Lead or Holter);

The subject has a positive Hepatitis B surface antigen or Hepatitis C antibody result at screening;

The subject has a history of elevated liver function tests on more than one occasion (ALT, AST and ALP>3× Upper Limit of Normal (ULN); total bilirubin>1.5×ULN) in the past 6 months;

Previous exposure or past infection caused by *Mycobacterium tuberculosis*;

The subject has an acute infection;

The subject has a history of repeated, chronic or opportunistic infections that, in the opinion of the investigator and/or GSK medical monitor, places the subject at an unacceptable risk as a participant in this trial;

The subject has a history of malignancy, except for surgically cured basal cell carcinoma or females with cured cervical carcinoma (>2 yrs prior);

The subject has a history of human immunodeficiency virus (HIV) or other immunodeficiency disease;

The subject whose calculated creatinine clearance is less than 50 ml/min;

The subject has significant cardiac, pulmonary, metabolic, renal, hepatic or gastrointestinal conditions that, in the opinion of the investigator and/or GSK medical monitor, places the subject at an unacceptable risk as a participant in this trial;

The subject has taken cyclosporine, leflonomide, cyclophophamide or azathioprine within 1 month of screening. Subjects that have taken cyclosporine, leflonomide, cyclophophamide or azathioprine in the past must have recovered from all drug related adverse events;

The subject has taken gold salts or d-penicillamine within 1 month prior to screening. Subjects that have taken gold salts or d-penicillamine in the past must have recovered from all drug related adverse events;

The subject has received intra-articular glucocorticoids within 1 month of screening;

Recent history of bleeding disorders, anaemia, peptic ulcer disease, haematemesis or gastrointestinal bleeding;

Subjects with a history of haematological disease or acquired platelet disorders, including drug-induced thrombocytopaenia, acute idiopathic thrombocytopaenia or von Willebrand's disease;

Subjects with a known risk of intra-cranial haemorrhage including Central Nervous System (CNS) surgery within the last 12 months, arterial vascular malformations, aneurysms, significant closed head trauma within 6 months or any other incident the investigator and/or medical monitor considers to be relevant;

The subject has Hb<10 g/deciliter (dL) and platelet count<150×109/Liter (L);

Donation of blood in excess of 500 ml within a 56 day period prior to dosing;

An unwillingness of male subjects to abstain from sexual intercourse with pregnant or lactating women; or an unwillingness of the male subject to use a condom with spermicide in addition to having their female partner use another form of contraception such as an interuterine device (IUD), diaphragm with spermicide, oral contraceptives, injectable progesterone, subdermal implants of levonorgestrel or a tubal ligation if the woman could become pregnant for at least 12 weeks after dosing;

An unwillingness of female subject of child bearing potential to use adequate contraception, as defined in the study restriction section. If necessary, women of non-child bearing potential (i.e. post-menopausal or surgically sterile e.g. tubal ligation or hysterectomy or bilateral oophorectomy) will be confirmed. Postmenopausal status will be confirmed by serum follicle stimulating hormone (FSH) and oestradiol concentrations at screening. Surgical sterility will be defined as females who have had a documented hysterectomy, tubal ligation or bilateral oophorectomy;

The subject has a history of use of drugs of abuse within 12 months prior to screening;

History of regular alcohol consumption exceeding average weekly intake of greater than 21 units or an average daily intake of greater than 3 units (males) or an average weekly intake of greater than 14 units or an average daily intake of greater than 2 units (females). Subjects who regularly consume more than 12 units of alcohol in a 24 h period will also be excluded. 1 unit is equivalent to a half-pint (220 ml) of beer/lager or 1 (25 ml) measure of spirits or 1 glass (125 ml) of wine;

Positive pregnancy test or lactating at screening;

Participation in a trial with any investigational drug within 3 months or 5 half-lives (whichever is longer) before.

Study Design:

This is a randomized, double-blinded, placebo-controlled adaptive, dose finding study to investigate the safety, tolerability, PK, PD and efficacy of single and repeat intravenous infusions of a compound of Formula (I) in patients with active rheumatoid arthritis. The study is divided into 2 parts: Part A is an adaptive, dose finding phase which will provide safety, tolerability, PK and PD on single intravenous infusions. Part B is a repeat dose phase which will provide safety, tolerability, PK, PD and efficacy following repeat intravenous infusions of a selected dose level.

Primary Outcome Measures:
Safety and Tolerability following single ascending doses of a compound of Formula (I) at 1 month and following 3 repeat doses of a compound of Formula (I) at 3 months. Clinical Efficacy (DAS28 score) of a compound of Formula (I) at 1 month Secondary Outcome Measures:
Weighted mean DAS28 after single and repeat intravenous doses
Plasma PK parameters of a compound of Formula (I) after single and repeat intravenous doses including free, and bound a compound of Formula (I) (serum) concentrations, $AUC_{(0-\infty)}$, $C_{max}$, clearance, volume of distribution and accumulation ratio
DAS28 and EULAR response criteria after single and repeat intravenous doses
ACR20/ACR50/ACR70 response after single and repeat intravenous doses
Number of swollen joints assessed using 28-joint counts
Number of tender/painful joints assessed using 28-joint counts
Subject's pain assessment
Physician's global assessment of arthritis condition
Patients' global assessment of arthritis condition
Functional disability index (Health Assessment Questionnaire)
C-reactive Protein (CRP)
ESR
Global Fatigue Index
HAQ disability index
Pharmacodynamic biomarkers after single and repeat intravenous doses
Characteristic $AUC_{50}$ and $EC_{50}$ for clinical endpoint changes with plasma exposure model, as assessed by sigmoid $E_{max}$ and indirect response PK/PD models.
Immunogenicity (Human anti-compound of Formula (I) antibodies)

Phase II Clinical Trial of the Safety and Efficacy of Compounds of Formula (I) in Patients with Severe, Recalcitrant, Plaque-type Psoriasis.

The purpose of this phase II trial is to investigate the safety, efficacy, and tolerability of a compound of Formula (I) in patients with severe, recalcitrant, plaque-type psoriasis.

Patients:
Eligible subjects will be men and women between the ages of 18 and 75.

Criteria:
Inclusion Criteria:
The patient has severe, recalcitrant, plaque-type psoriasis and has failed at least 1 systemic therapy (for the purposes of this study psoralen with ultraviolet light A is considered to be a systemic therapy);
The patient has psoriatic involvement of at least 10% of BSA;
The patient has a PSGA score of 4 or greater;
The patient, if a woman, is surgically sterile or 2 years postmenopausal, or if of childbearing potential is currently using a medically accepted method of contraception, and agrees to continue use of this method for the duration of the study (and for 30 days after participation in the study). Acceptable methods of contraception include: abstinence, steroidal contraceptive (oral, transdermal, implanted, or injected) in conjunction with a barrier method, or intrauterine device (IUD);
The patient, if a main, is surgically sterile, or if capable of producing offspring, is currently using an approved method of birth control, and agrees to continued use of this method for the duration of the study (and for 60 days after taking the last dose of a compound of Formula (I) because of the possible effects on spermatogenesis);
The patient must be willing and able to comply with study procedures and restrictions and willing to return to the clinic for the follow-up evaluation as specified in this protocol.

Exclusion Criteria:
The patient has received treatment with systemic psoriasis treatments (specifically, retinoids, methotrexate, cyclosporine A, etanercept, efalizumab, other biological agents or other immunomodulators) within 4 weeks, or UV based therapy within 2 weeks, or alefacept within 6 weeks of the planned 1st day of study treatment;
The patient has received treatment with potent CYP3A4 inhibitors including cyclosporine, clotrimazole, fluconazole, itraconazole, ketoconazole, voriconazole, erythromycin, clarithromycin, and troleandomycin, human immunodeficiency virus (HIV) protease inhibitors, or nefazodone within 1 week (7 days) of the planned 1st day of study treatment;
The patient is currently receiving warfarin;
The patient has hypersensitivity to a compound of Formula (I) or any component of a compound of Formula (I);
The patient has one or more of the following serum chemistry values as determined at the screening visit (visit 1):
bilirubin levels greater than 2 times the upper limit of normal (ULN);
ALT or AST levels greater than 2 times the ULN;
serum creatinine levels or more than 2 mg/dL;
The patient requires current treatment for HIV with protease inhibitors;
The patient is taking medication for a clinical diagnosis of gastrointestinal ulceration or has experienced melena or hematoemesis in the previous 3 weeks;
The patient is a woman who is pregnant or lactating;
The patient has received treatment with an investigation drug within 4 weeks of the planned 1st day of study treatment.

Study Design:
This is an exploratory, open-label, nonrandomized, dose-escalation study of the efficacy, safety, and tolerability of a compound of Formula (I) in patients with severe, recalcitrant, plaque-type psoriasis.

Phase II Clinical Trial of the Safety and Efficacy of Compounds of Formula (I) for Prophylaxis of Acute Rejection after Renal Transplantation The standard immunosuppressive treatment after renal transplantation is a combination of tacrolimus, mycophenolate mofetil, and prednisolone. With this regimen the incidence of acute rejection within the first six months after transplantation can drop to about 20%. The main challenge at present remains to improve long-term outcome by preventing chronic allograft nephropathy (CAN). Since acute rejection is a strong predictor of CAN, a further decrease in the incidence of acute rejection can improve the long-term graft survival. The purpose of this phase II clinical trial is to investigate the effectiveness and safety of a compound of Formula (I) for prophylaxis of acute rejection after renal transplantation.

Patients:
Eligible subjects will be men and women ages 18 and older

Criteria:
Inclusion Criteria:
Renal transplant recipients;
Signed, dated, and witnessed IRB approved informed consent;

Exclusion Criteria:
Pregnancy;
Living donor, who is HLA identical;
Hemolytic uremic syndrome as original kidney disease;
Focal segmental glomerulosclerosis that had recurred in a previous graft;
More than two previously failed grafts and/or PRA>85%;
Diabetes mellitus that is currently not treated with insulin;
Total white blood cell count<3,000/mm3 or platelet count<75,000/mm3;
Active infection with hepatitis B, hepatitis C, or HIV;
History of tuberculosis.
Study Design:
This is a randomized, double blind, placebo controlled intervention study on the efficacy and safety of the prophylactic use of a compound of Formula (I). One group will receive a single dose of a compound of Formula (I) intravenously at the time of transplantation, and the other group receives a placebo infusion.
Primary Outcome:
To determine the incidence and severity of biopsy-confirmed acute rejection within the first six months after transplantation
Secondary Outcomes:
Renal function as estimated by the endogenous creatinine clearance at 6 months
Occurrence of chronic allograft nephropathy at 6 months
Cumulative incidence of infections and malignancies at 6 months
Medical costs during the first 6 months after transplantation
Patient and graft survival Phase II Clinical Trial of the Safety and Tolerability of a compound of Formula (I) in Patients with Active Ulcerative Colitis (UC)

The purpose of this phase II trial is to investigate the safety, tolerability of a compound of Formula (I) regimen in patients with active ulcerative colitis.
Patients:
Eligible subjects will be men and women aged 18 and older
Criteria:
Inclusion Criteria:
Active UC on 5-ASA therapy and also treated with 6-MP and/or corticosteroids or who have previously been treated with AZA, 6-MP or corticosteroids and could not tolerate them;
Mayo score of 6 to 10 points with moderate to severe disease on endoscopy (Mayo score of at least 2) performed <14 days of study drug administration;
Subjects on the following medications may be enrolled into the study if the medications were according to the following schedules prior to study drug administration and if no changes are anticipated during the study;
  prednisolone ≦20 mg daily (or equivalent) (dose must be stable for at least 2 weeks prior to study drug administration);
  5-ASA (dose must be stable for at least 4 weeks prior to study drug administration);
  AZA or 6-MP (dose must be stable for at least 3 months prior to study drug administration);
  Rectal steroids or 5-ASA (must have been stable for at least 4 weeks prior to study drug);
Subjects using rectal medications must have visible disease on sigmoidoscopy at ≧20 cm;
Screening laboratory values must meet certain criteria:
Women must be postmenopausal (>12 months without menses) or surgically sterile (e.g., by hysterectomy and/or bilateral oophorectomy) or must be using effective contraception (e.g., oral contraceptives, intrauterine device (IUD), double barrier method of condom and spermicidal) for at least 4 weeks prior to study drug administration and agree to continue contraception for the duration of their participation in the study; and
Sexually active male subjects must use a barrier method of contraception during the duration of the study
Exclusion Criteria:
Anti-TNF therapy within 8 weeks before study drug administration;
Any experimental therapy more therapy ≦4 weeks before study drug administration;
Prior treatment with any monoclonal antibody or immunoglobulin-based fusion proteins ≦8 weeks prior to study treatment;
Presence of Cushing's syndrome;
Toxic megacolon or fulminant disease likely to require colectomy;
Contraindication to colonoscopy or sigmoidoscopy;
Primary or secondary immunodeficiency;
Autoimmune disease besides UC, with the exceptions of Sjogren's syndrome or hypothyroidism;
History of malignancy, excluding adequately treated and cured basal or squamous cell of the skin, or cervical carcinoma in situ;
Major psychiatric disease (subjects with stable depression receiving appropriate management will be permitted in the study);
Evidence of acute or chronic infection as evidenced by:
stool culture positive for pathogens and/or *Clostridium difficile* toxin;
findings on Screening chest radiography such as pulmonary infiltrate(s) or adenopathy;
current treatment for tuberculosis infection, clinical or radiological evidence of active TB, or for subjects in North America, a positive PPD without prior prophylaxis;
Herpes zoster ≦3 months prior to study drug administration;
active infectious disease requiring i.v. antibiotics within 4 weeks prior to study treatment or oral antibiotics at the time of enrollment;
HIV or AIDS;
positive tests for HBV, or HCV indicating active or chronic infection;
Clinically significant cardiac disease requiring medication, unstable angina, myocardial within 6 months, or congestive heart failure;
Arrhythmia requiring active therapy, with the exception of clinically insignificant or minor conduction abnormalities;
History of cerebrovascular disease requiring medication/treatment;
Anticoagulation therapy or a known bleeding disorder;
Seizure disorder requiring active therapy;
Known drug or alcohol abuse;
Pregnant or nursing;
Any underlying medical condition that in the Principal Investigator's opinion will make the study drug hazardous to the subject or would obscure the interpretation of treatment efficacy or safety; or
Inability or unwillingness to return for Follow-up visits and comply with study protocol
Primary Outcome Measures:
Change in Mayo score at Day 57 compared with Screening Secondary Outcome Measures:
Remission rate
Study Design:

This is a phase II, double-blind, placebo-controlled, randomized, multi-dose study of a compound of Formula (I) in subjects with active UC experiencing flare. All subjects will have active disease while on a 5-ASA containing medication and are either on stable doses of corticosteroids and/or azathioprine or 6-mercaptopurine, or who have previously been on these medications but could not tolerate them. Flare is defined as a Mayo score of 6 to 10 with moderate to severe disease activity on endoscopy (Mayo endoscopic subscore of at least 2) within 2 weeks of receiving study drug administration. Doses of permitted concomitant medications (corticosteroids, azathioprine (AZA), 6-mercaptopurine (6-MP), and 5-aminosalicylates (5-ASA) containing compounds) should remain constant during the course of the study. Subjects will be randomized to receive placebo or a compound of Formula (I) intravenously on Days 1, 15, 29, and 43. All subjects will be seen in the clinic at regular intervals up to Day 85 for safety, efficacy, pharmacokinetic, and/or pharmacodynamic assessments. All subjects will be contacted 70 days after the last dose of study drug. Assessment of safety will be determined by vital sign measurements, clinical laboratory tests, physical examinations, immunogenicity assessments, chest x-ray, electrocardiograms, and the incidence and severity of treatment emergent adverse events. The primary clinical assessment of activity will be determined by the change in Mayo score at Day 57 compared with Screening. Secondary endpoints include determination of remission rate by the mayo score at Day 57, evaluation of mucosal healing and change from baseline in the IBDQ score.

Phase II Clinical Trial of the Safety and Efficacy of Compounds of Formula (I) in Patients with Multiple Sclerosis The purpose of this phase II trial is to investigate the safety, efficacy and tolerability of a compound of Formula (I) in patients with Relapsing-Remitting Multiple Sclerosis.

Patients:

Eligible subjects will be men and women between the ages of 18 and 65.

Criteria:
Inclusion Criteria:
Have a definite diagnosis of Relapsing remitting Multiple Sclerosis
Have a history of at least 1 of the following: a. A minimum of 2 relapses of MS within the previous 2 years but not within the 1-month period prior to screening. b. A relapse of MS within the previous 6 months but not within the 1-monthperiod prior to screening
Exclusion Criteria:
Have a CNS disease (e.g., CNS lymphoma, systemic lupus erythematous)
Have significant bulbar involvement of MS or other neurologic deficits
Have a decubitus ulcer
Have received immunomodulatory therapies within 3 months of screening
Primary Outcome Measures:
The cumulative number of newly Gd-enhancing T1-weighted lesions on cranial MRIs through week 23
Secondary Outcome Measures:
The total number of relapses of MS through week 23; change from baseline in Expanded Disability Status Scale (EDSS) score at week 23
Study Design:
This is a phase II, double-blind, placebo-controlled, randomized, dose-ranging study of multiple subcutaneous injections of a compound of Formula (I) in patients with relapsing-remitting multiple sclerosis. Patients will receive subcutaneous injections of a compound of Formula (I) or placebo at weeks 0, 1, 2, 3, 7, 11, 15, and 19 or 100.

Pharmaceutical Compositions

Parenteral Composition

To prepare a parenteral pharmaceutical composition suitable for administration by injection, 100 mg of a compound of Formula (I) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I) | 1.2 g |
| sodium acetate buffer solution (0.4 M) | 2.0 mL |
| HCl (1 N) or NaOH (1 M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formula (I) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I) | 200 |
| lactose, spray-dried | 148 |
| magnesium stearate | 2 |

In yet another embodiment, the following ingredients are mixed to form a solution/suspension for oral administration:

| Ingredient | 1. Amount |
| --- | --- |
| 2. Compound of Formula (I) | 4. 1 g |
| 3. Anhydrous Sodium Carbonate | 5. 0.1 g |
| 6. Ethanol (200 proof), USP | 7. 10 mL |
| 8. Purified Water, USP | 9. 90 mL |
| 10. Aspartame | 11. 0.003 g |

Sublingual (Hard Lozenge) Composition

To prepare a pharmaceutical composition for buccal delivery, such as a hard lozenge, mix 100 mg of a compound of Formula (I) with 420 mg of powdered sugar mixed with 1.6 mL of light corn syrup, 2.4 mL distilled water, and 0.42 mL mint extract. The mixture is gently blended and poured into a mold to form a lozenge suitable for buccal administration.

Inhalation Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Rectal Gel Composition

To prepare a pharmaceutical composition for rectal delivery, 100 mg of a compound of Formula (I) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Suppository Formulation

A suppository of total weight 2.5 g is prepared by mixing a compound of Formula (I) with Witepsol™H-15 (triglycerides of saturated vegetable fatty acid; Riches-Nelson, Inc., New York), and has the following composition:

| Ingredient | Quantity per suppository, mg |
|---|---|
| compound of Formula (I) | 500 |
| Witepsol ® H-15 | balance |

Topical Gel Composition

To prepare a pharmaceutical topical gel composition, 100 mg of a compound of Formula (I) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical opthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and in some embodiments, various modifications or changes are to be included within the purview of disclosure and scope of the appended claims.

What is claimed is:

1. A pharmaceutical composition comprising a pharmaceutically acceptable diluent, excipient or binder, and a compound of Formula (I):

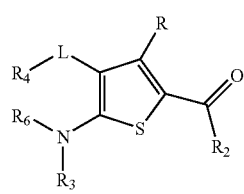

Formula (I)

wherein:
  L is a bond;
  R is hydrogen, $CO_2R_1$, an optionally substituted heteroaryl, or an optionally substituted heterocycloalkyl;
  $R_1$ is hydrogen, $C_1$-$C_6$alkyl, $C_1$-$C_6$cycloalkyl, $C_1$-$C_6$haloalkyl, phenyl or benzyl;
  $R_2$ is cycloalkyl, aryl, arylalkyl, heteroaryl, heteroarylalkyl, or heteroarylalkenyl, wherein cycloalkyl, aryl, arylalkyl, heteroaryl, heteroarylalkyl, or heteroarylalkenyl is optionally substituted with at least one $R_5$;
  $R_3$ and $R_6$ are each independently hydrogen, $C_1$-$C_6$alkyl, —C(O)—$C_1$-$C_6$alkyl, or —C(O)N$R_1$—$C_1$-$C_6$alkyl, wherein $C_1$-$C_6$alkyl is optionally substituted with at least one $R_5$;
  $R_4$ is aryl or heteroaryl; wherein aryl or heteroaryl is optionally substituted with at least one $R_5$;
  each $R_5$ is independently selected from F, Cl, Br, I, —CN, alkyne, $C_1$-$C_6$ alkylalkyne, —$NO_2$, —OH, —$CF_3$, —$OCF_3$, —$OR_8$, $C_1$-$C_6$alkyl, $C_3$-$C_8$ cycloalkyl, $C_1$-$C_6$heteroalkyl, $C_1$-$C_6$haloalkyl, tetrazolyl, $C_2$-$C_8$heterocycloalkyl, optionally substituted aryl, optionally substituted heteroaryl, —NHS(=O)$_2R_8$, —S(=O)$_2$N($R_9$)$_2$, —N($R_9$)S(=O)$_2$N($R_9$)$_2$, —C(=O)$CF_3$, —C(=O)NHS(=O)$_2R_8$, —S(=O)$_2$NHC(=O)$R_8$, —N($R_9$)$_2$, —N($R_9$)C(=O)$R_8$, —N($R_9$)C(=O)N($R_9$)$_2$, —N($R_9$)C(=O)O$R_8$, —$CO_2R_9$, —C(=O)$R_8$, —OC(=O)$R_8$, —OC(=O)N($R_9$)$_2$, —CON($R_9$)$_2$, —$SR_8$, —S(=O)$R_8$, and —S(=O)$_2R_8$;
  each $R_8$ is independently selected from $C_1$-$C_6$alkyl, $C_1$-$C_6$haloalkyl, $C_3$-$C_8$cycloalkyl, phenyl, and benzyl; and
  each $R_9$ is independently selected from H, $C_1$-$C_6$alkyl, $C_1$-$C_6$haloalkyl, $C_3$-$C_8$cycloalkyl, phenyl, and benzyl; or pharmaceutically acceptable salt thereof.

2. A pharmaceutical composition comprising a pharmaceutically acceptable diluent, excipient or binder, and a compound selected from:

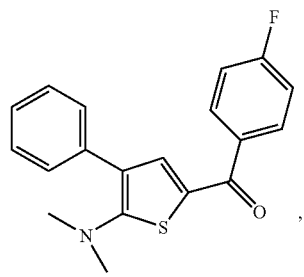

,

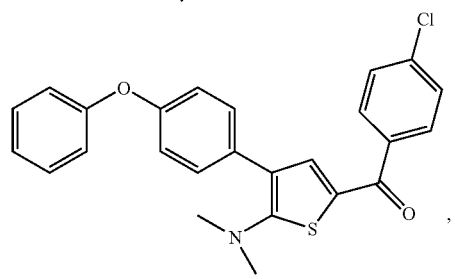

,

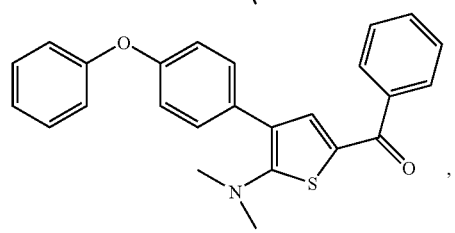

,

95
-continued
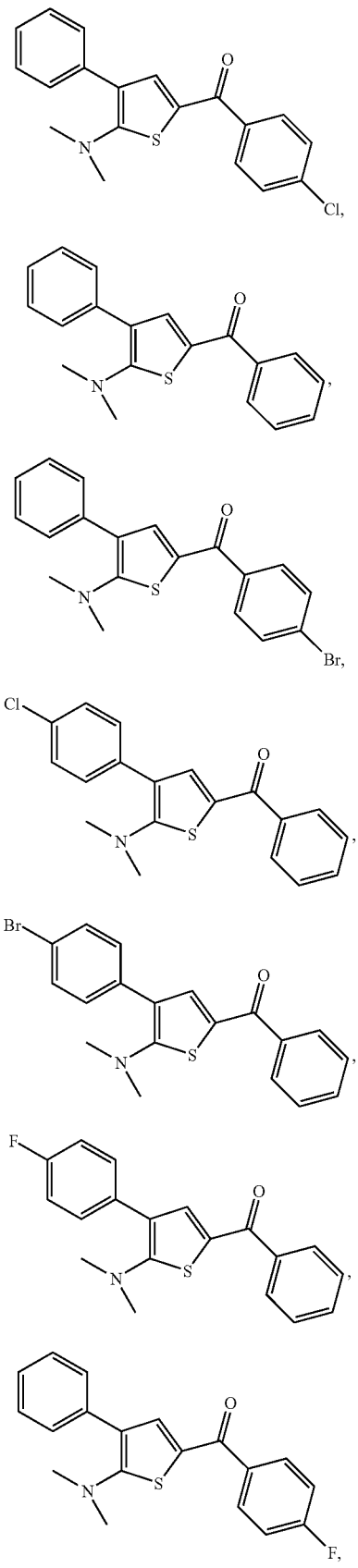
96
-continued
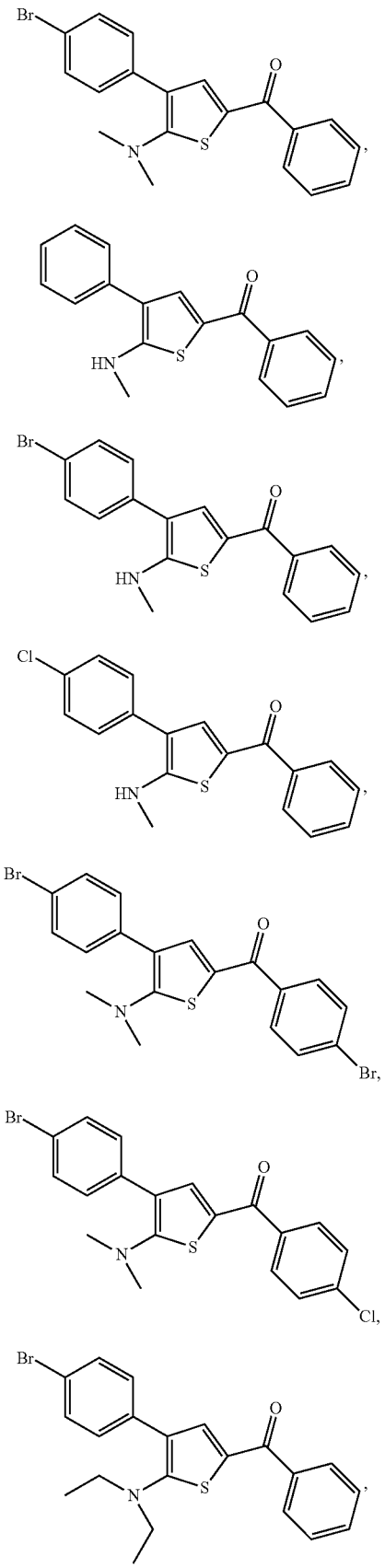

97

-continued

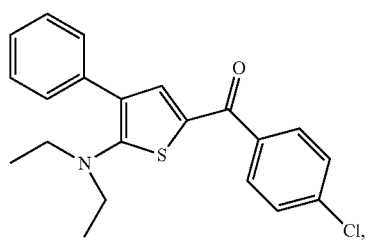

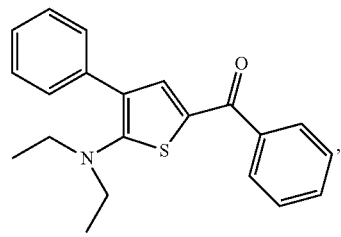

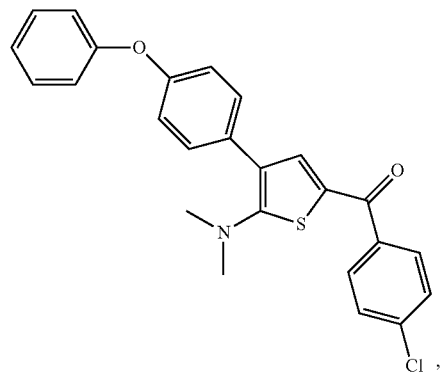

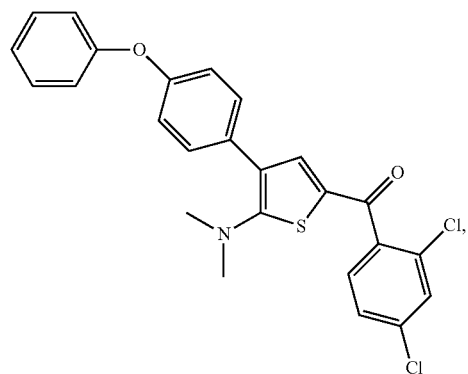

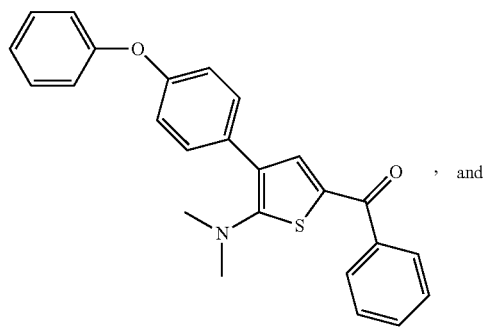

98

-continued

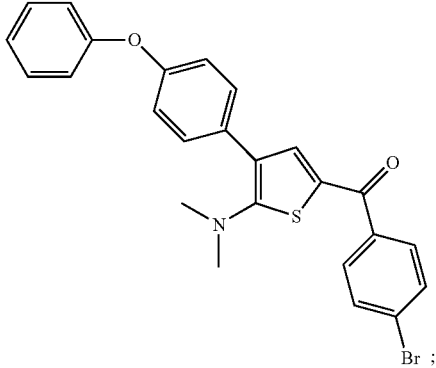

or pharmaceutically acceptable salt, pharmaceutically acceptable solvate, or pharmaceutically acceptable prodrug thereof.

3. A compound of Formula (I):

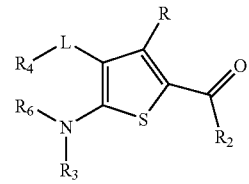

Formula (I)

wherein:
L is a bond;
R is hydrogen, $CO_2R_1$, an optionally substituted heteroaryl, or an optionally substituted heterocycloalkyl;
$R_1$ is hydrogen, $C_1$-$C_6$alkyl, $C_1$-$C_6$cycloalkyl, $C_1$-$C_6$haloalkyl, phenyl or benzyl;
$R_2$ is cycloalkyl, aryl, arylalkyl, heteroaryl, heteroarylalkyl, or heteroarylalkenyl, wherein cycloalkyl, aryl, arylalkyl, heteroaryl, heteroarylalkyl, or heteroarylalkenyl is optionally substituted with at least one $R_5$;
$R_3$ and $R_6$ are each independently hydrogen, $C_1$-$C_6$alkyl, —C(O)—$C_1$-$C_6$alkyl, or —C(O)N$R_1$—$C_1$-$C_6$alkyl, wherein $C_1$-$C_6$alkyl is optionally substituted with at least one $R_5$;
$R_4$ is aryl or heteroaryl; wherein aryl or heteroaryl is optionally substituted with at least one $R_5$;
each $R_5$ is independently selected from F, Cl, Br, I, —CN, alkyne, $C_1$-$C_6$ alkylalkyne, —$NO_2$, —OH, —$CF_3$, —$OCF_3$, —$OR_8$, $C_1$-$C_6$alkyl, $C_3$-$C_8$cycloalkyl, $C_1$-$C_6$heteroalkyl, $C_1$-$C_6$haloalkyl, tetrazolyl, $C_2$-$C_8$heterocycloalkyl, optionally substituted aryl, optionally substituted heteroaryl, —NHS(=O)$_2R_8$, —S(=O)$_2$N($R_9$)$_2$, —N($R_9$)S(=O)$_2$N($R_9$)$_2$, —C(=O)$CF_3$, —C(=O)NHS(=O)$_2R_8$, —S(=O)$_2$NHC(=O)$R_8$, —N($R_9$)$_2$, —N($R_9$)C(=O)$R_8$, —N($R_9$)C(=O)N($R_9$)$_2$, —N($R_9$)C(=O)O$R_8$, —$CO_2R_9$, —C(=O)$R_8$, —OC(=O)$R_8$, —OC(=O)N($R_9$)$_2$, —CON($R_9$)$_2$, —$SR_8$, —S(=O)$R_8$, and —S(=O)$_2R_8$;
each $R_8$ is independently selected from $C_1$-$C_6$alkyl, $C_1$-$C_6$haloalkyl, $C_3$-$C_8$cycloalkyl, phenyl, and benzyl; and
each $R_9$ is independently selected from H, $C_1$-$C_6$alkyl, $C_1$-$C_6$haloalkyl, $C_3$-$C_8$cycloalkyl, phenyl, and benzyl; or
a pharmaceutically acceptable salt thereof.

4. The compound of claim 3 wherein R is $CO_2H$.

5. The compound of claim 3 wherein R is H.

6. The compound of claim 3 wherein $R_3$ and $R_6$ are each independently $C_1$-$C_6$alkyl.

7. The compound of claim 3 wherein $R_2$ is aryl.

8. The compound of claim 3 wherein $R_4$ is aryl.

9. The compound of claim 7 wherein aryl is phenyl.

10. The compound of claim 7 wherein phenyl is substituted with F, Cl, Br, or I.

11. The compound of claim 7 wherein phenyl is substituted with —$OR_8$.

12. The compound of claim 11 wherein $R_8$ is phenyl.

13. The compound of claim 8 wherein aryl is phenyl.

\* \* \* \* \*